US008235997B2

(12) United States Patent
Hoffman et al.

(10) Patent No.: US 8,235,997 B2
(45) Date of Patent: Aug. 7, 2012

(54) ROD LOCKING INSTRUMENT

(75) Inventors: Jeffrey Hoffman, Marquette, MI (US);
Joseph Mohar, Marquette, MI (US);
Maria M. Norman, Negaunee, MI (US);
Gregory Berrevoets, Skandia, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 579 days.

(21) Appl. No.: 12/362,429

(22) Filed: Jan. 29, 2009

(65) Prior Publication Data
US 2009/0228054 A1 Sep. 10, 2009

Related U.S. Application Data

(60) Provisional application No. 61/024,465, filed on Jan. 29, 2008, provisional application No. 61/024,470, filed on Jan. 29, 2008.

(51) Int. Cl.
*A61B 17/70* (2006.01)
(52) U.S. Cl. ........................................ 606/86 A; 606/53
(58) Field of Classification Search .................. 606/53, 606/247, 267, 279, 86 A, 99
See application file for complete search history.

(56) References Cited

U.S. PATENT DOCUMENTS

| | | |
|---|---|---|
| 1,359,164 A | 11/1920 | Giudice |
| 1,832,879 A | 11/1931 | Ruskin |
| 1,863,037 A | 6/1932 | Archbold |
| 1,977,282 A | 10/1934 | Kruse |
| 1,985,108 A | 12/1934 | Rush |
| 2,370,308 A | 2/1945 | Hanson |
| 2,523,385 A | 9/1950 | Mead |
| 2,594,102 A | 4/1952 | Vollmer |
| 2,598,650 A | 5/1952 | Smith et al. |
| 2,655,953 A | 10/1953 | Miloche |
| 2,664,774 A | 1/1954 | Harvie |
| 2,669,145 A | 2/1954 | Mead |
| 2,814,222 A | 11/1957 | Sanders |
| 3,181,181 A | 5/1965 | Buckley et al. |
| 3,477,429 A | 11/1969 | Sampson |
| 3,486,505 A | 12/1969 | Morrison |
| 3,618,612 A | 11/1971 | Ahn |
| 3,641,652 A | 2/1972 | Arnold et al. |
| 3,981,308 A | 9/1976 | Schlein |

(Continued)

FOREIGN PATENT DOCUMENTS
WO 9311715 6/1993
(Continued)

OTHER PUBLICATIONS

Brochure, "Spiral Radium 90D™ Surgical Technique," Tyco Healthcare/Surgical Dynamics, 11 pages.

(Continued)

*Primary Examiner* — Eduardo C Robert
*Assistant Examiner* — Lynnsy Schneider
(74) *Attorney, Agent, or Firm* — Fitch, Even, Tabin & Flannery, LLP

(57) ABSTRACT

Instruments and methods are provided for securing a spinal rod in one or more coupling devices secured to the spine by one or more anchor members. The instruments include members for grasping the coupling device and members for shifting one or more elements along a linear path to fix the position of an anchor member and/or fix the position of the rod with respect to the vertebra.

14 Claims, 59 Drawing Sheets

U.S. PATENT DOCUMENTS

| | | | |
|---|---|---|---|
| 4,050,464 A | 9/1977 | Hall | |
| 4,111,206 A | 9/1978 | Vishnevsky et al. | |
| 4,147,167 A | 4/1979 | Hickmann et al. | |
| 4,153,321 A | 5/1979 | Pombrol | |
| 4,271,836 A | 6/1981 | Bacal et al. | |
| 4,316,468 A | 2/1982 | Klieman et al. | |
| 4,318,316 A | 3/1982 | Guilliams | |
| 4,325,376 A | 4/1982 | Klieman et al. | |
| 4,409,968 A | 10/1983 | Drummond | |
| 4,411,259 A | 10/1983 | Drummond | |
| 4,445,513 A | 5/1984 | Ulrich et al. | |
| D291,729 S | 9/1987 | Greig | |
| 4,793,225 A | 12/1988 | Berkich | |
| 4,809,695 A | 3/1989 | Gwathmey et al. | |
| 4,870,965 A | 10/1989 | Jahanger | |
| 4,896,661 A | 1/1990 | Bogert et al. | |
| 4,898,161 A | 2/1990 | Grundei | |
| 4,911,154 A | 3/1990 | Vickers | |
| 4,927,425 A | 5/1990 | Lozier | |
| 4,950,273 A | 8/1990 | Briggs | |
| 4,966,600 A | 10/1990 | Songer et al. | |
| 5,020,519 A | 6/1991 | Hayes et al. | |
| D331,625 S | 12/1992 | Price et al. | |
| 5,167,662 A | 12/1992 | Hayes et al. | |
| D346,217 S | 4/1994 | Sparker et al. | |
| 5,364,397 A | 11/1994 | Hayes et al. | |
| 5,368,596 A | 11/1994 | Burkhart | |
| 5,616,143 A | 4/1997 | Schlapfer et al. | |
| 5,704,937 A | 1/1998 | Martin | |
| 5,720,751 A * | 2/1998 | Jackson | 606/86 R |
| 5,782,831 A | 7/1998 | Sherman et al. | |
| 5,885,299 A | 3/1999 | Winslow et al. | |
| 5,899,901 A | 5/1999 | Middleton | |
| 5,910,141 A | 6/1999 | Morrison et al. | |
| 5,951,564 A | 9/1999 | Schroder et al. | |
| 6,017,342 A | 1/2000 | Rinner | |
| 6,036,692 A | 3/2000 | Burel et al. | |
| 6,083,225 A | 7/2000 | Winslow et al. | |
| 6,139,549 A | 10/2000 | Keller | |
| 6,251,111 B1 | 6/2001 | Barker et al. | |
| 6,261,296 B1 | 7/2001 | Aebi et al. | |
| 6,440,133 B1 * | 8/2002 | Beale et al. | 606/86 A |
| 6,478,801 B1 | 11/2002 | Ralph et al. | |
| 6,648,888 B1 | 11/2003 | Shluzas | |
| 6,660,006 B2 * | 12/2003 | Markworth et al. | 606/86 A |
| 7,481,813 B1 * | 1/2009 | Purcell | 606/86 R |
| 7,572,281 B2 * | 8/2009 | Runco et al. | 606/279 |
| 7,771,430 B2 * | 8/2010 | Jones et al. | 606/86 A |
| 7,887,541 B2 * | 2/2011 | Runco et al. | 606/86 A |
| 2001/0027318 A1 | 10/2001 | Oribe et al. | |
| 2002/0026197 A1 | 2/2002 | Foley et al. | |
| 2002/0072753 A1 | 6/2002 | Cohen | |
| 2002/0095153 A1 | 7/2002 | Jones et al. | |
| 2002/0123754 A1 | 9/2002 | Holmes et al. | |
| 2002/0133157 A1 | 9/2002 | Sterett et al. | |
| 2003/0009168 A1 | 1/2003 | Beale et al. | |
| 2003/0199872 A1 | 10/2003 | Markworth et al. | |
| 2003/0225408 A1 | 12/2003 | Nichols et al. | |
| 2004/0049191 A1 | 3/2004 | Markworth et al. | |
| 2004/0147937 A1 | 7/2004 | Dunbar, Jr. et al. | |
| 2004/0267275 A1 * | 12/2004 | Cournoyer et al. | 606/99 |
| 2006/0025768 A1 | 2/2006 | Lott et al. | |
| 2006/0089651 A1 | 4/2006 | Trudeau et al. | |
| 2007/0213722 A1 | 9/2007 | Jones et al. | |
| 2008/0154277 A1 | 6/2008 | Machalk et al. | |
| 2009/0157125 A1 | 6/2009 | Hoffman et al. | |

FOREIGN PATENT DOCUMENTS

WO         2006047659         5/2006

OTHER PUBLICATIONS

Brochure, "Universal Instrumentation (CD) for Spinal Surgery," Dr. Cotrel et al., Stuart, 1985, 20 pages.

* cited by examiner

ROD LOCKING INSTRUMENT

CROSS REFERENCE TO RELATED APPLICATIONS

This application claims the benefit of U.S. provisional patent applications 61/024,465, filed Jan. 29, 2008, and 61/024,470, filed Jan. 29, 2008, both of which are hereby incorporated fully by reference as if set forth herein.

FIELD OF THE INVENTION

The present systems and methods relate to instruments for manipulating bone fixation devices. More particularly, the present systems and methods provide for instruments for locking components of a coupling device configured to facilitate the fixation of vertebral bodies, such as a low profile screw assembly.

BACKGROUND OF THE INVENTION

Various devices for internal fixation of bone segments in the human or animal body are known in the art. One type of system is a pedicle screw system, which is sometimes used as an adjunct to spinal fusion surgery, and which provides a means of anchoring an implantable member to a spinal segment. A conventional pedicle screw system comprises a pedicle screw and a rod-receiving device (also referred to herein as a coupling device or coupling assembly, since it couples a spinal rod to the pedicle screw or other bone anchor). The pedicle screw usually includes an externally threaded body or shank and an enlarged head portion, although the head portion may be eliminated by providing an integral shank portion extending from the rod-receiving device. The rod-receiving device often includes a top portion having a U-shaped channel to receive the spinal rod and a lower portion having a seat for receiving the head portion of the pedicle screw. Multiple screw assemblies may be implanted along the spine and connected by a rod to fix the vertebrae in a desired orientation and stabilize the spinal column. The goal of such a system may be, for instance, to substantially reduce and/or prevent relative motion between spinal segments that are being fused or to de-rotate an abnormal spine.

Some pedicle screw systems lack features that enhance and/or benefit newer, minimally invasive surgery (MIS) techniques that are more commonly being used for spinal surgeries. For instance, installation and locking of coupling assemblies often involves complex manipulation of a plurality of components of the screw system, and sometimes also requires a screw or other anchor to be assembled with a rod-receiving device prior to implantation. The assembly may obstruct the working space, making it more difficult to insert the anchor into a vertebra and manipulate the coupling device during surgery. Furthermore, assemblies with polyaxial fixation devices in the prior art ordinarily rely on downward force of the rod against the head of the bone anchor to secure the bone anchor against pivoting, so that the assembly, and specifically the rod receiving portion thereof, is provided with little support or stability prior to full locking of the rod. Some pedicle screw systems also include rather large and bulky assemblies to secure a rod, thus increasing opportunities for tissue damage in and around the surgical site during installation. Many of these systems also include set-screw type locking mechanisms or multi-part cap structures that require rotation or complex manipulation of small components and/or require a significant portion of the assembly to be located above the rod, increasing the height (profile) of the implants extending radially away from the spinal column, which may cause patient discomfort after implantation. Systems with set screws for securing the rod within the coupling assembly also lack a predetermined locking position, requiring a surgeon to turn the set screw a number of revolutions in order to secure the rod. When locking the rod in place with a set screw or other similar structure, the surgeon must also determine when the assembly "feels" locked, often resulting in overtorquing of the locking mechanism or false locking of the assembly. Cross-threading is also often a problem in such systems, and can result in damage to the assembly or a failure to fully lock the cap.

Due to the limited working space at the site of implantation and the number of components to be assembled, instruments have been developed to stabilize the coupling assembly, shift spinal rods into coupling assemblies, and lock rods in place by securing a locking cap to the coupling assembly. For instance, U.S. Patent Application No. 2006/0089651 discloses an instrument for advancing a spinal rod into a coupling member or yoke of a pedicle screw assembly. After a clamp device is used to secure the instrument to the coupling member, a drive assembly advances a locking cap and spinal rod into the coupling member in response to rotation of a first member, and then rotates the locking cap to secure the cap and rod to the coupling member in response to rotation of a second member.

Other such devices are disclosed in U.S. Patent Application No. 2003/0225408 and U.S. Pat. No. 6,648,888. These systems, however, require manipulation of a plurality of actuators to secure the rod-receiving device, shift the spinal rod, and lock the cap to the rod-receiving device. For instance, a first actuator may secure the instrument to the assembly while a second actuator drives the locking cap into the coupling assembly and a third actuator locks the locking cap to the assembly via rotation. Furthermore, the actuators in those systems often rely on threaded drive members to cause shifting of components, so that a member must be rotated a great number of revolutions in order to effect any significant amount of linear shifting.

Some such systems also have deficiencies such as an inability to fully stabilize the rod during linear shifting, failure to provide indication of when full locking of the cap and rod-receiving device has been achieved, and failure to provide mechanisms to allow multiple predetermined stages of locking for the assembly (i.e. a first "provisional" locking stage that prevents the rod from escaping the rod-receiving device but allows for rod adjustment, followed by a "full" locking stage that immobilizes the rod with respect to the coupling device). Furthermore, many of these systems are designed specifically for use with set screws or rotating cap members, and therefore may not be compatible with other types of coupling assemblies. There remains a need, therefore, for improved instruments for locking pedicle screw assemblies that are easy to use and allow a surgeon to quickly secure a spinal rod in place.

SUMMARY OF THE INVENTION

Instruments for assembling and/or locking low profile coupling devices for coupling an elongate member, such as a spinal rod, to one or more anchor members attached to vertebrae are provided herein. The instruments are designed for systems in which a cap member is linearly shifted into locking engagement with the coupling device, such as in co-pending application Ser. Nos. 11/726,868, filed Mar. 22, 2007, and 12/257,285, filed Oct. 23, 2008, the full disclosures of which are hereby incorporated by reference as if fully set forth herein. The coupling devices disclosed therein, sometimes referred to as tulip assemblies, include an outer member or body, an insert member or core for being axially received in the outer member and attaching to a bone anchor, and a cap member for securing the rod within the assembly. The assembly is locked by axial shifting of the outer member and cap member with respect to the insert member. Axial shifting of these components compresses the insert member and exerts a locking force upon the head of the bone anchor and upon the rod, both of which are disposed in the insert member in the illustrated embodiments of application Ser. Nos. 11/726,868 and 12/257,285. These locking forces are exerted upon the bone anchor and rod in directions transverse to the direction in which the outer member and cap are shifted. The anchor member in such an assembly may include a screw, hook, or other bone fixation device for securing implants to bone. It should be noted that locking of the anchor is not necessary if an anchor portion is formed integrally with other components of the assembly, which may also eliminate the need for separate inner and outer members. Although the anchor member may be formed integrally with the insert member, outer member, or a unitary member combining the functions of the insert member and outer member, so that no locking force is required to fix it in place with respect to the coupling assembly, it is preferably provided as a separate structure to be pivotably received in an insert member and/or outer member to allow the inner and outer members to be fixed at various angles with respect to the anchor.

An instrument for locking an elongate member such as a spinal rod within this type of coupling assembly or tulip assembly includes a grasping device for engaging the coupling assembly (preferably the outer member of the assembly) and maintaining it in a desired relationship and orientation with respect to the instrument. The grasping device may be formed by an integral component, or may be a subassembly made up of two or more members. In one form, the grasping device includes a plurality of axially-extending projections having clamp portions disposed thereon, the clamp portions effective for engaging and clamping to surface features on the tulip assembly. In one form, the axially-extending projections are resiliently flexible, allowing the projections of the grasping device to flex outward to receive the outer tulip member and thereafter flex inward to secure the tulip assembly. Alternatively, the grasping member may form a split sleeve capable of radially expanding at the split end to receive the outer tulip member. In another form, the grasping member may include one or more pivotable jaw members that pivot to an open position to receive the coupling assembly and pivot to a closed position to clamp the coupling assembly in position.

The instrument further includes a moveable drive member configured to linearly advance the cap member into locking engagement with the outer member and/or insert member of the coupling assembly. In one form, the drive member is an elongate drive rod disposed within the grasping device and configured for axial travel therethrough, although alternative configurations also are contemplated. The drive member may be equipped with flexible protrusions at one end for releasably engaging the cap member. Preferably, the flexible protrusions grip the cap with an amount of force sufficient to hold the cap to the drive member in a desired orientation with respect to the tulip assembly, but with less force than the locking force between the cap and the tulip assembly. In this manner the cap is automatically released from the drive member as the drive member retracts after shifting the cap into locking engagement with the tulip assembly. Alternatively, the drive member may be configured to drive the cap into position without gripping the cap at all.

An actuator mechanism is also provided for shifting the drive member toward and away from the tulip assembly. In one form, the actuator mechanism comprises an actuator lever operatively coupled to the drive member. The actuator lever may be, for instance, connected to the drive member by one or more pivot points so that shifting or pivoting the actuator lever is translated to linear travel of the drive member. In one form, a spring or other biasing device may be provided to bias the actuator member toward an open position corresponding to a retracted position of the drive member. A ratchet mechanism may also be included so that the actuator mechanism may be shifted to a predetermined position or shifted a predetermined number of times to carry out a desired function without that function being reversed when the actuator is released.

The instrument may also comprise one or more structures for shifting the grasping device from an open position to a clamped position. For instance, the grasping device may include a slit or other gap having a wide portion and a narrow portion, so that a moveable structure that travels through the gap, such as a deflection member extending transversely through the gap, deflects clamping portions of the grasping device and widens the gap when the deflection member is disposed in the narrow portion of the passage and allows the clamping portions to shift toward one another when the deflection member is disposed in the wide portion of the gap. Alternatively, an outer sleeve may be provided to translate along the exterior of the grasping device, forcing clamping portions of the grasping device toward one another during travel of the sleeve.

In one aspect the deflection member or deflection sleeve for manipulating the grasping device may be coupled to the drive member so that clamping is achieved during a portion of the linear travel of the drive member. In this manner, a single actuator may be used to clamp the clamp portions of the grasping device and linearly shift the drive member.

A reducing member may also be provided to assist in shifting the spinal rod into seated engagement within the coupling assembly. The reducing member may, for instance, exert a shifting force upon the rod at spaced locations along the rod axis on either side of the area contacted by the drive rod, providing greater rod stability during operation of the instrument. Such a configuration also allows the rod to be reduced prior to introduction of the cap and held in place while the cap is secured to the coupling assembly without interfering with locking of the cap to the coupling assembly and without requiring the reducing member to be moved out of the way prior to locking of the cap. In one form, shifting of the reducing member may be coupled to shifting of the drive member so that a single actuator shifts the reducing member and the drive member.

If the drive member, grasping device, and reducing member are all coupled together, a single actuator may be effective for causing clamping of the grasping device, shifting of the reducing member, and/or shifting of the drive rod at various orientations of the actuator or upon activating the actuator a predetermined number of times.

In one form, the grasping device, drive member, and reducing member may be concentrically disposed about a single axis, so that the drive member is axially disposed in a sleeve forming the grasping device, which is in turn axially disposed in a sleeve forming the reducing member. Advantageously, a drive coupler having shiftable elements may be used to releasably couple the reducing member to the drive member, with the shiftable elements shifting from an engaged position to a disengaged position in order to decouple the reducing member and drive member at a predetermined position or predetermined load. In this manner, shifting of the drive member may be coupled to shifting of the reducing member through a first portion of the drive member's travel, while being independent of the reducing member in a second portion of the drive member's travel, allowing the drive member to continue to drive the cap into place even after the reducing member has fully reduced the spinal rod within the coupling assembly.

In another form, instruments may be provided that have only some of the above components to perform one or more of securing an anchor member to a coupling assembly, fixing the position of an anchor, positioning a spinal rod, and securing a spinal rod within a coupling assembly.

BRIEF DESCRIPTION OF THE DRAWINGS

The accompanying drawings illustrate various exemplary embodiments of the present systems and methods. The illustrated embodiments are examples of the present systems and methods and do not limit the scope thereof.

FIG. 16a is a front view of a second exemplary instrument.

FIG. 16b is an isometric view of the instrument of FIG. 16a.

Throughout the drawings, identical reference numbers designate similar but not necessarily identical elements.

DETAILED DESCRIPTION

Figure 1:
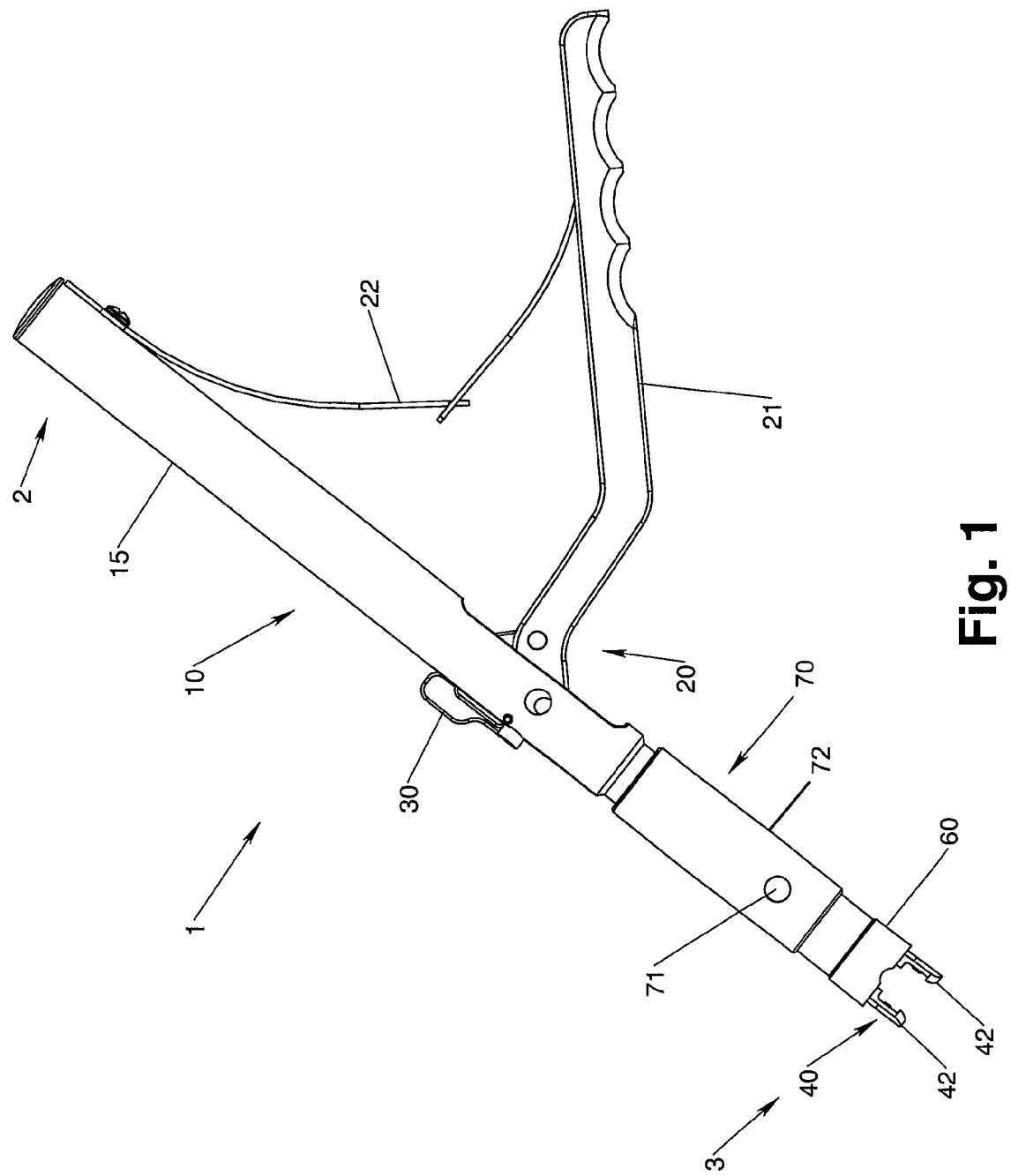
FIG. 1 is a front view of an exemplary instrument.
Figure 2:
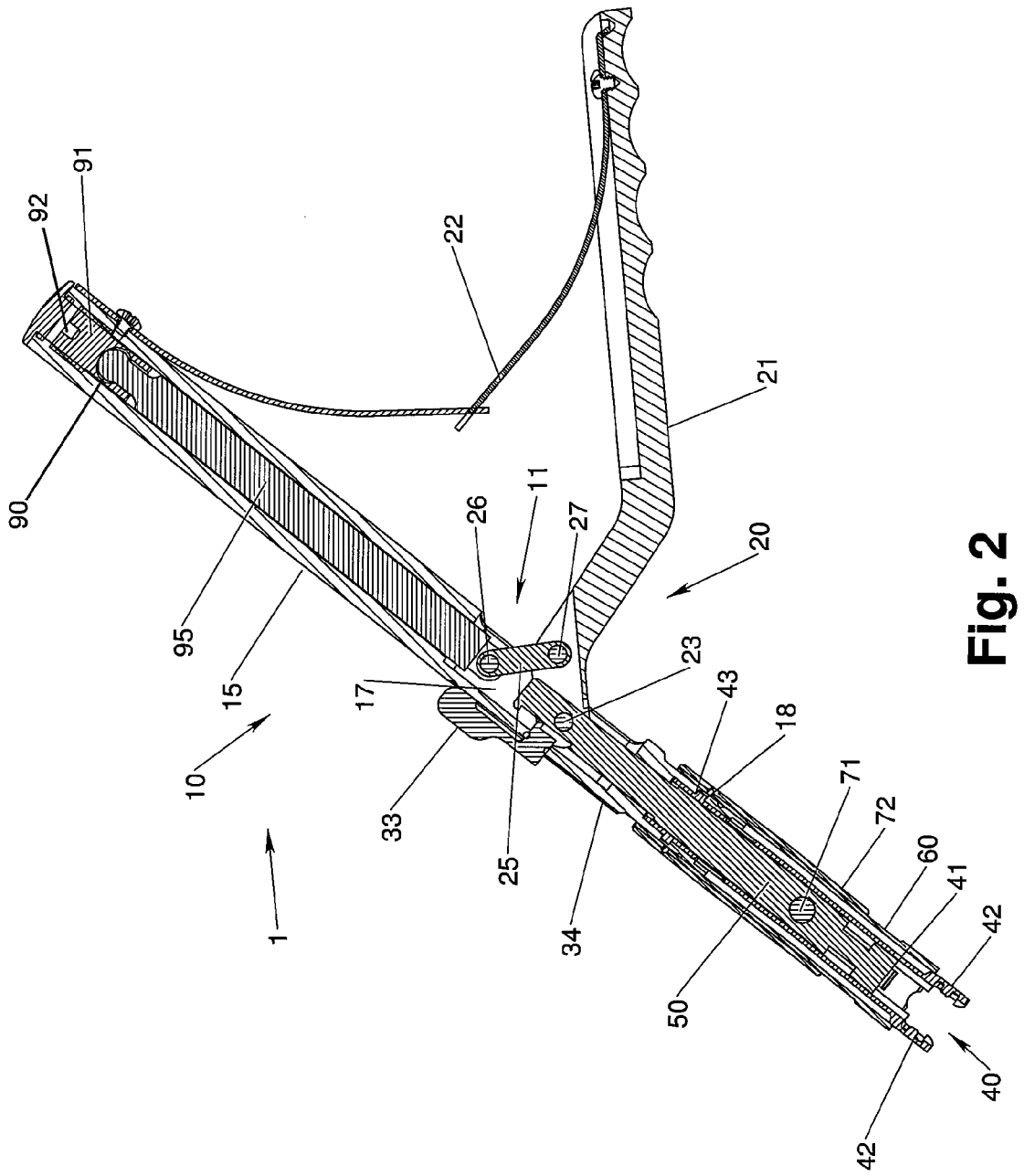
FIG. 2 is a first cross-sectional view of the instrument in FIG. 1.
Figure 3:
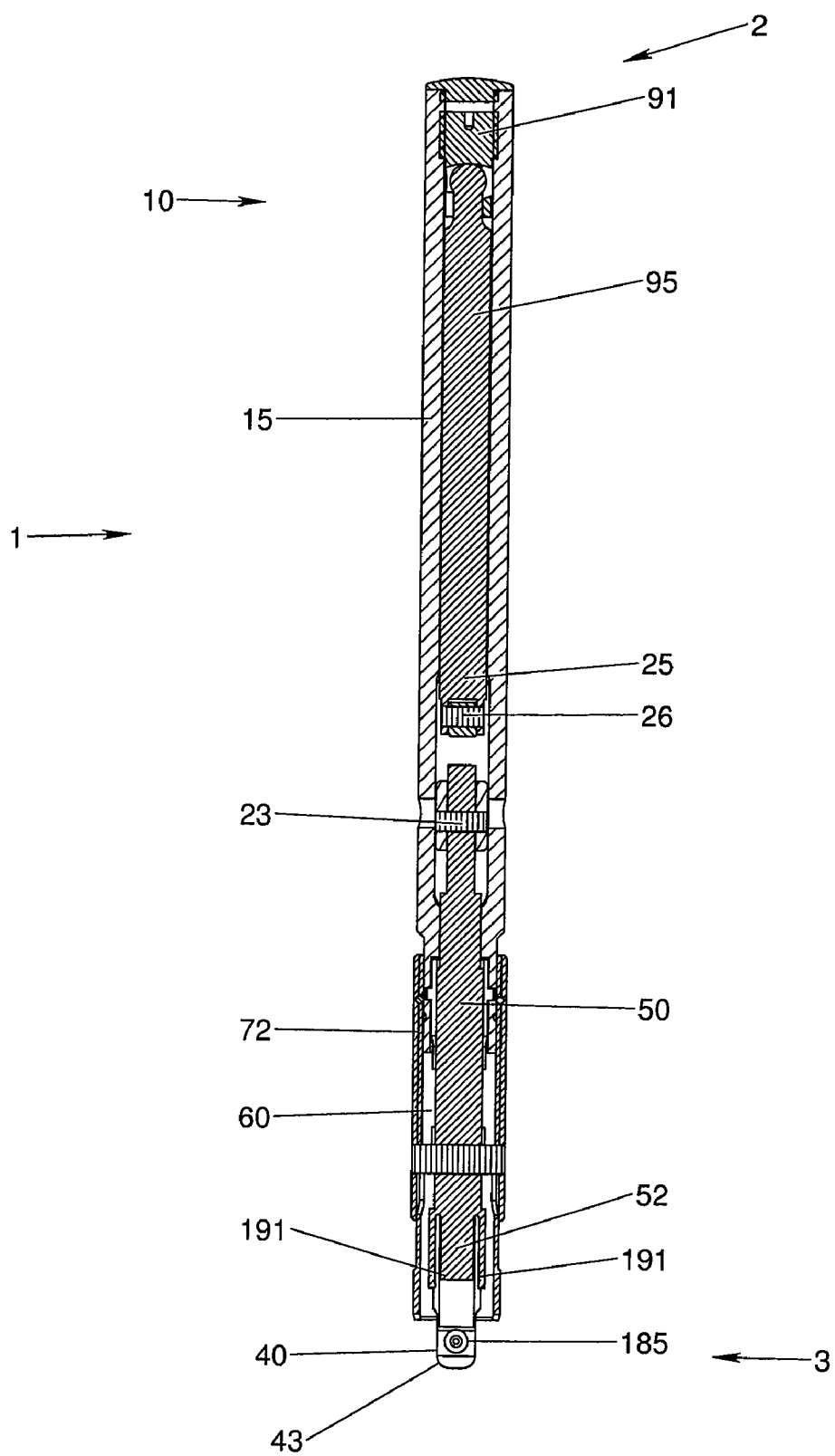
FIG. 3 is a second cross-sectional view transverse to the cross-section of FIG. 2.

One exemplary instrument for securing a rod and an anchor member within a coupling assembly is shown in FIGS. 1 and 2. The illustrated embodiment comprises an instrument body 10 having a handle 15, an actuator assembly 20 having an actuator in the form of a lever 21, a radially expandable grasping device 40 extending axially from the instrument body, an axially shiftable drive member 50 extending from the instrument body and disposed within the grasping device, a reducing member in the form of a reducing sleeve 60 surrounding the grasping device and axially moveable with respect thereto, and a drive coupler 70 having a coupling sleeve 72 and a coupling pin 71. The coupling of the drive member 50 to the reducing member 60 and drive coupler subassembly 70 is illustrated by the side cross-sectional view of FIG. 3. The components of the instrument 1 are shown disassembled in FIG. 4 for reference in the following discussion.

Figure 4:
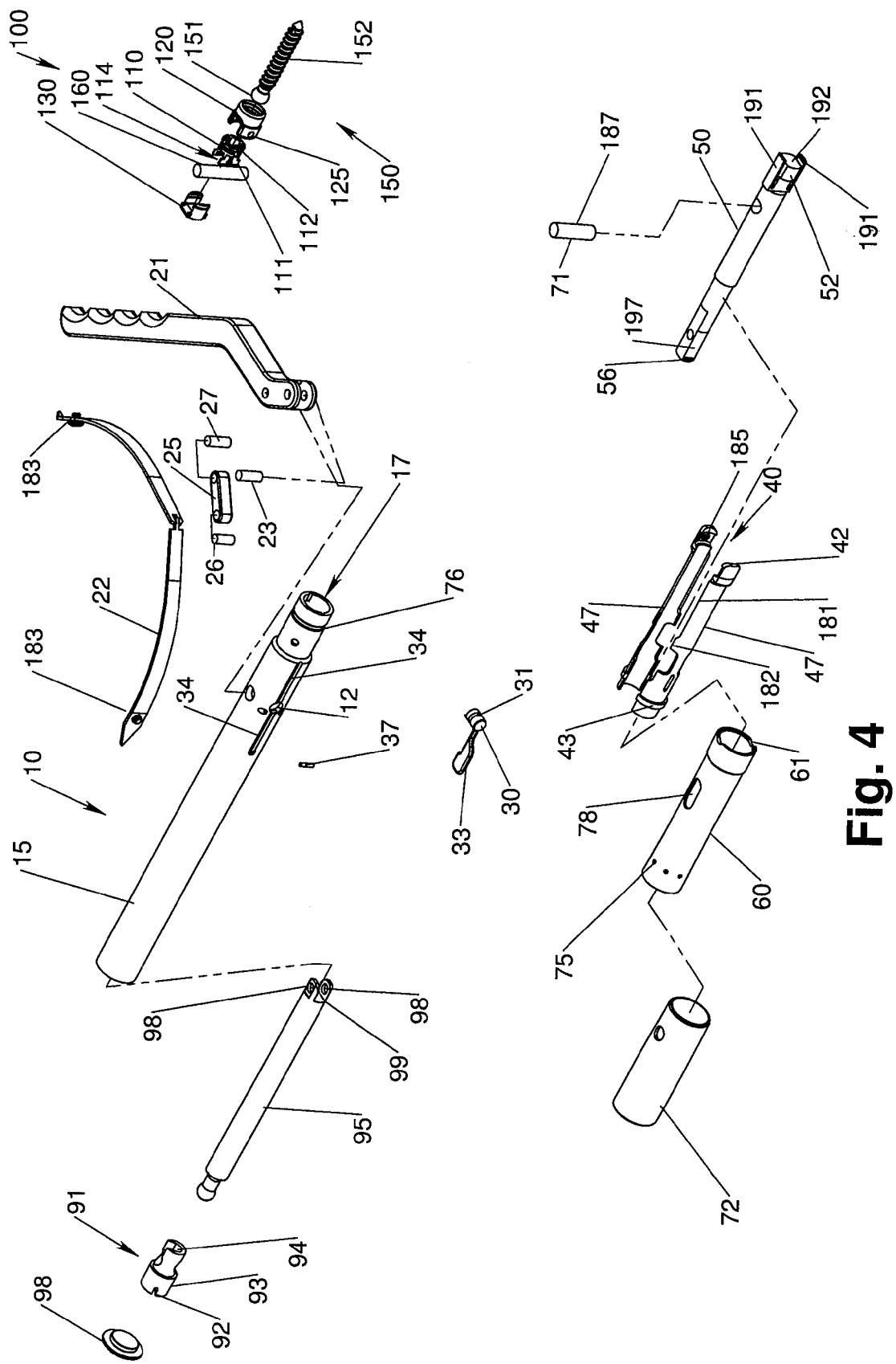
FIG. 4 is an exploded view showing the instrument from FIG. 2 in a disassembled state.

An exemplary coupling assembly of the type that may be used with the instrument is also shown in FIG. 4 in the form of a tulip assembly 100. The tulip assembly includes an insert member 110 and an outer body member 120. The tulip assembly 100 serves to couple a fixation device, such as a pedicle screw 150, to an elongate member, such as spinal rod 160. Locking of the fixation device to the assembly is accomplished by axial movement of the insert member 110 with respect to the body member 120, which causes radial compression of a lower portion 112 of the insert member 110 about the head 151 of the pedicle screw 150. More specifically, the lower portion 112 of the insert member 110 contains a socket 117 for receiving the head 151 of the screw 150, and slits 118 in the lower insert portion 112 allow the lower portion 112 to be compressed as the exterior of the insert 110 engages inwardly-directed radial protrusions 123 in the interior of the outer tulip member 120. Additional details regarding exemplary coupling assemblies may be found by referring to co-pending application Ser. Nos. 11/726,868 and 12/257,285, both of which are hereby incorporated by reference.

Referring to FIGS. 1-4, the instrument 1 has an elongate structure with a proximal end 2 to be held by a surgeon and a distal end 3 for manipulating the coupling device 100. The instrument body 10 has a portion forming a handle 15 to be gripped by the surgeon, and includes an axial bore 17 running therethrough in which a drive member 50 is disposed. An actuator opening 11 opens to the bore 17 and allows an actuator assembly 20 to connect to the drive rod 50 disposed in the bore 17.

Figure 5:
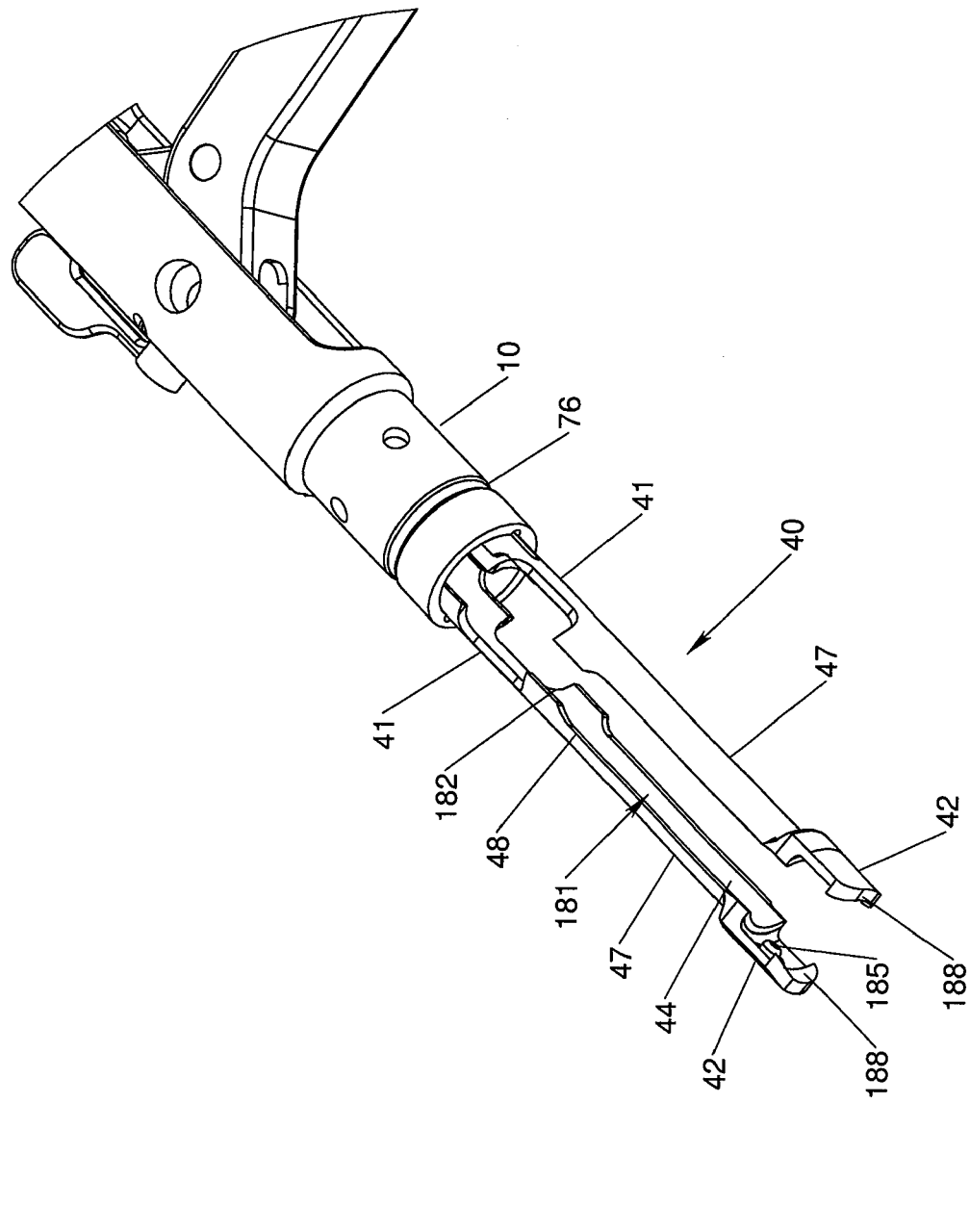
FIG. 5 is a magnified view of the internally-disposed grasping device of the instrument in FIG. 1.

A grasping device 40 is located at the distal end 3 of the instrument body 10. An attachment member may be provided to fix the grasping device to the instrument body, such as the illustrated flange 43 extending along the circumference of the grasping device 40 and configured to be received in an annular recess 18 in the interior of the body member 10. Alternatively, the grasping device may be formed as an integral portion of the instrument body. The grasping device 40 engages the outer tulip body 120 of the tulip assembly 100 and maintains it in a desired relationship and orientation with respect to the instrument 1. The grasping device 40 is made up of projections 41 extending from the instrument body 10 and configured to receive the tulip assembly 100. In one embodiment, as shown in FIG. 5, the grasping device 40 includes separate first and second elongate parallel grasping members 47 that extend from the instrument body 10 along the axis thereof. The grasping members 47 are arranged parallel to one another, and together form a sleeve having a passage 44 through which the drive member 50 may pass. Instead of multiple members, the grasping device may be formed as a single sleeve with a slit therein. In addition, the grasping device may be integral to the instrument body, or may be formed as a separate component or components as shown.

Each of the grasping members 47 has a contoured edge 48 disposed along the gap 45 between the members. Each grasping member 47 also has a clamp portion 42 at the distal end thereof. The clamp portions are configured to engage the outer member 120 of the coupling device 100, and are shown having pegs 185 for receipt in side apertures 129 of the outer member 120 of the coupling assembly (FIG. 4).

Figure 6:
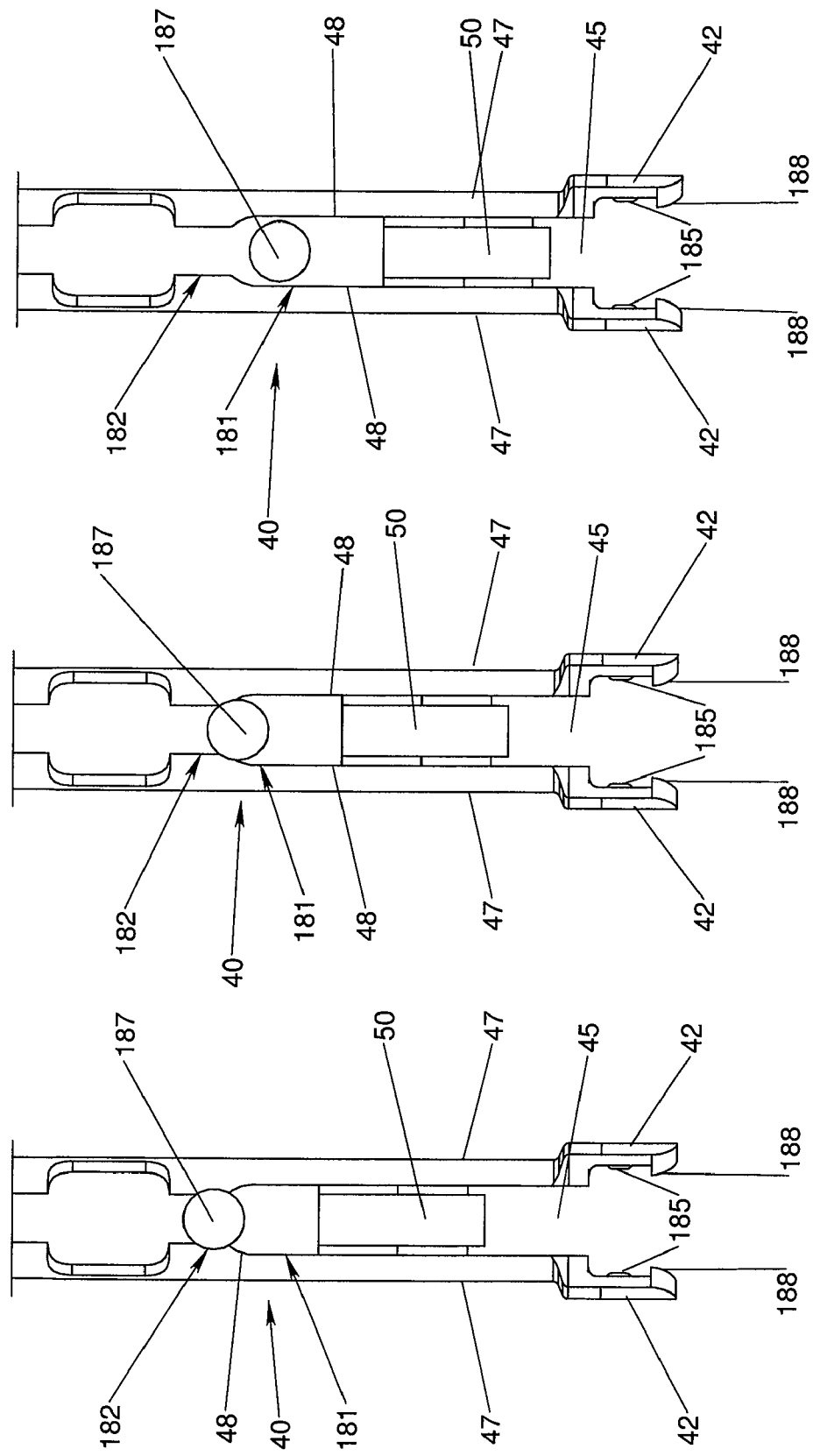
FIGS. 6a-6c are sequential views demonstrating operation of the grasping device.

An actuator may be provided to assist the grasping device 40 in capturing the coupling assembly outer member 120. For instance, as shown in FIGS. 6a-c, a protrusion or deflection member 187 may pass through the gap 45 in the grasping device so that the grasping members 47 are shifted in a direction A away from one another to an open position (FIG. 6a) when the protrusion is in a narrow portion 182 of the gap 45 and are allowed to flex back to their normal clamped positions when the protrusion is in the wide portion 181 of the gap 45. As shown, the deflection member 187 is a pin 71 coupled to the drive member 50, with the pin interacting with contoured edges 48 to shift the grasping members 47 between open and clamped positions, although other configurations are possible. In this case, the pin 71 also provides other functions and couples the drive member 50 to other components of the instrument, although a separate deflection member and separate coupling structure could alternatively be provided.

Other actuating systems may also be used to clamp the coupling device 100. For instance, the grasping device may be initially positioned in an open position with an actuator configured to shift members of the grasping device toward one another to capture the tulip body 120. For instance, the arms 47 of the grasping device may be biased outward, such as by forming the protrusions that form the device so that they are bent and naturally splayed slightly outward, so that a sleeve member such as reducer member 60 or other structure that slides axially along the exterior of the grasping device 40 shifts the clamp portions 42 inward to grasp a coupling device 100 received therebetween.

Other configurations for grasping the coupling assembly outer member 120, including configurations for grasping the coupling assembly without an actuator mechanism, are also possible. For instance, the clamp portions may include distal wedge surfaces allowing the coupling assembly outer member 120 to snap-lock between the clamp portions of the grasping device, allowing the linear insertion of the coupling assembly outer member 120 between grasping members to flex the grasping members outward to accept the coupling assembly, with the members thereafter resiliently flexing back to their original positions to capture the tulip body.

Clamping and unclamping may be designed to take place in one or a few simple steps. For instance, the actuator may be configured so that it springs open once released, immediately releasing the coupling assembly from the clamp portion of the grasping member to allow the surgeon to quickly disengage the instrument and proceed with the locking of the next coupling assembly.

Figure 7:
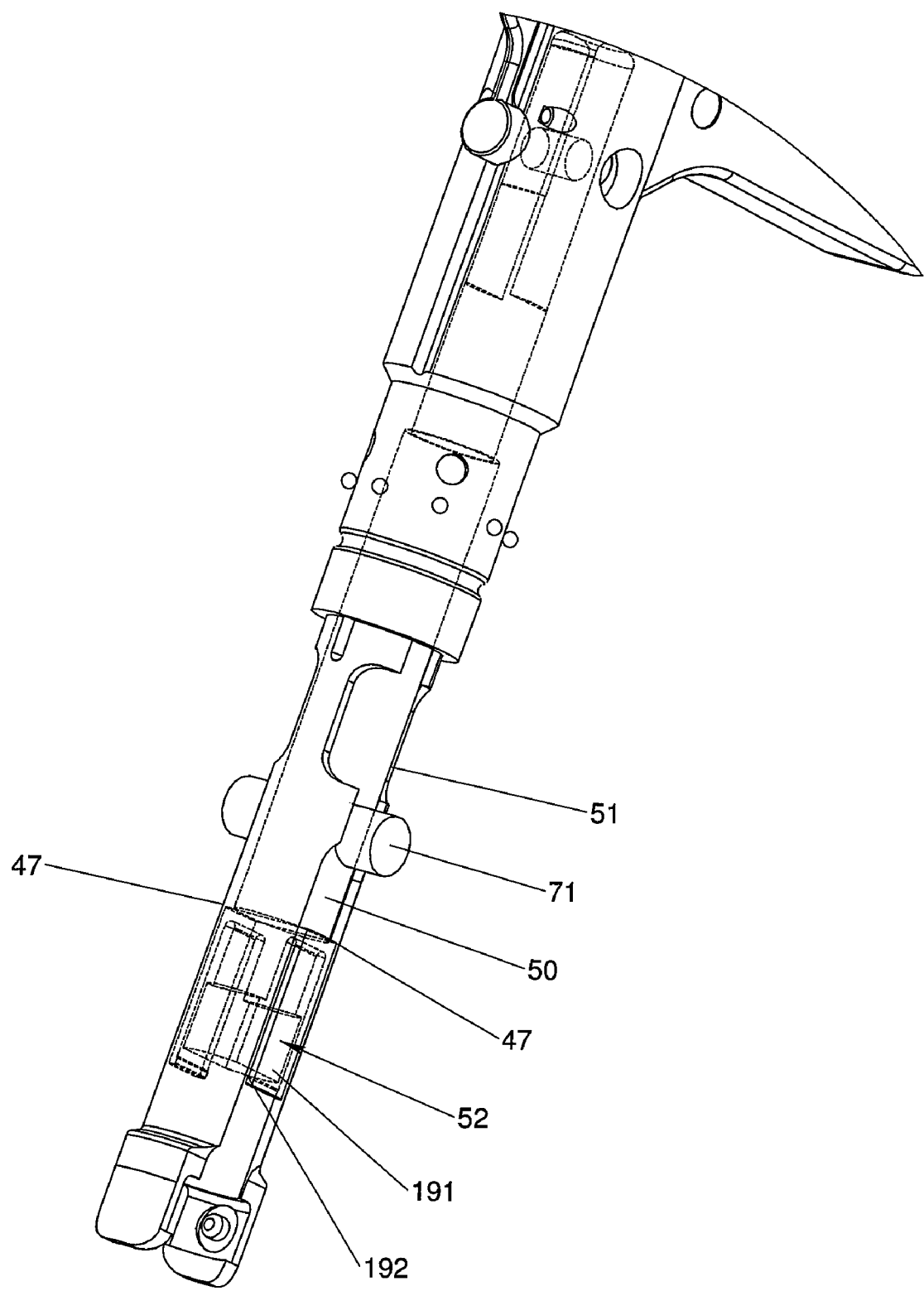
FIG. 7 is a detailed view of a drive member and grasping device.

Also extending from the instrument body 10 is a moveable drive member disposed within the bore 17 of the instrument body 10 as well as within the axial passage 44 through the grasping device, as shown in FIG. 7. The drive member 50 includes a shaft 51 and a head portion 52 that is configured to receive the cap member 130 of the coupling device 100. The drive member is capable of linearly advancing the cap member without rotation toward the clamp portions 42 of the grasping device 40 and into locking engagement with the outer member 120 and/or insert member 110 of the coupling device 100 when the coupling assembly is held in place by the grasping device 40.

Figure 8:
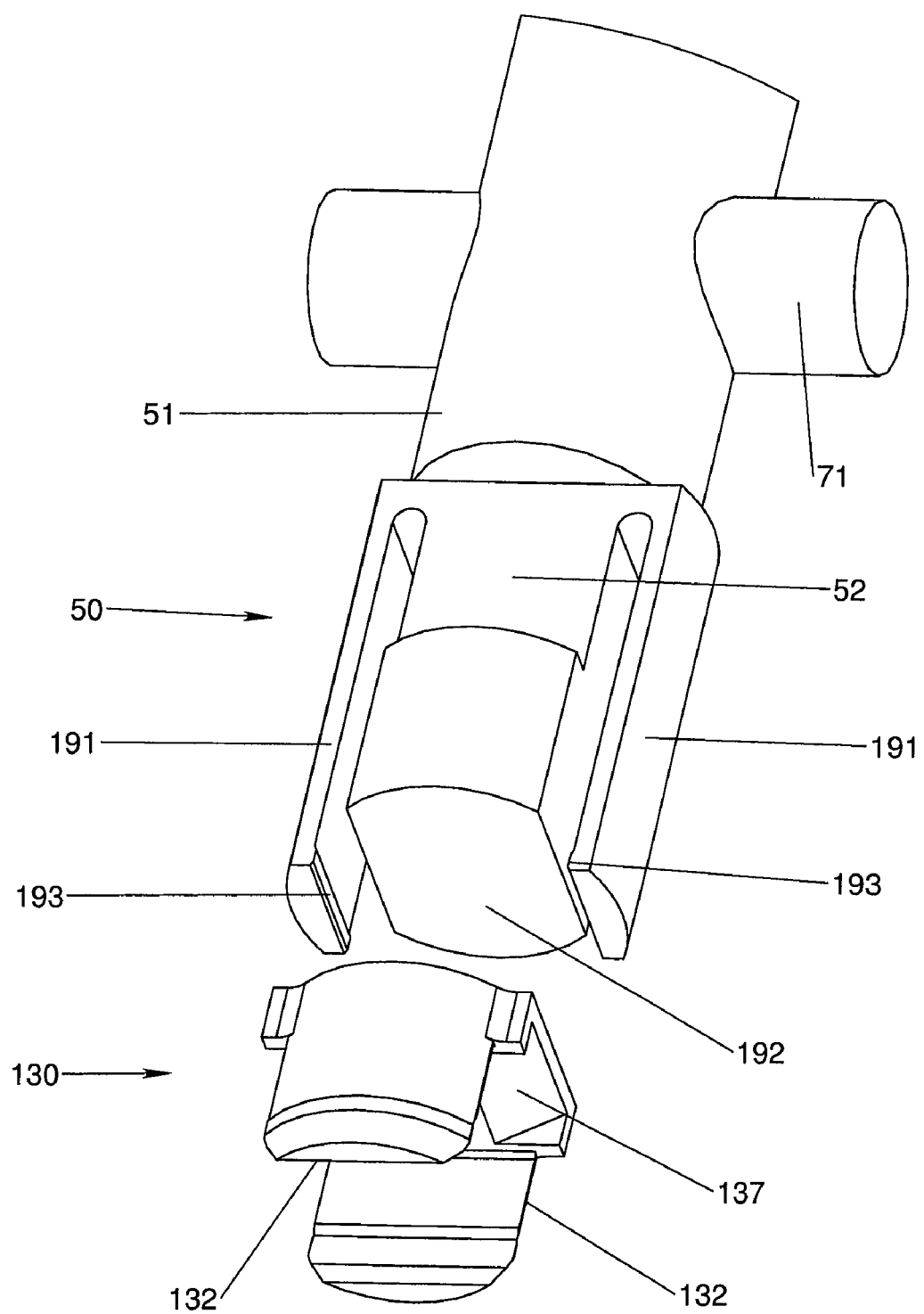
FIG. 8 shows a magnified view of the drive member head coupled to a cap member of the coupling assembly.

Although numerous methods of advancing the cap into the coupling member are possible, the head portion 52 of the drive member 50 may include flexible protrusions at one end for releasably engaging and holding the cap member 130. For instance, as best shown in FIG. 8, one embodiment has a head portion 52 that contains flexible arms 191 to grip the outer edge of the cap 130 and hold the cap to a downwardly-facing driving face 192. The cap 130 is held by the arms 191 with an amount of force sufficient to temporarily hold the cap to the driving face 192 with legs 132 of the cap member extending axially from the drive member 50 and toward the coupling assembly outer member 120 held in the grasping device 40. However, the holding force of the drive member arms 191 is less than the locking force between the cap and the tulip assembly so that the cap automatically disengages from the drive member head 52 upon retraction of the drive member 50 after insertion of the cap into engagement with the coupling assembly.

An actuator assembly 20 is provided for shifting the drive member 50 toward and away from the clamp portion 42 of the grasping device 40. The actuator assembly connects to the instrument body 10 and the drive member 50 to cause shifting of the drive member with respect to the instrument body. The illustrated form of actuator assembly 20 includes an actuator lever 21 extending from an actuator opening 11 in the instrument body 10 and pivotably coupled to the drive member 50 by a drive pin 23. A pivot link 25 connects the lever 21 to the instrument body 10 through a first pivot pin 26 coupled to the instrument body 10 and a second pivot pin 27 coupled to the lever 21. The fixed length of the pivot link 25 holds the second pivot pin 27 disposed in the lever 21 at a fixed distance from the first pivot pin 26 in the body as the lever shifts toward the instrument handle 15. Therefore, as the lever 21 pivots about drive pin 23 toward the handle 15, pivot link 25 pivots in an arcuate path about the first pivot pin 26, maintaining the second pivot pin 27 in the lever 21 at a fixed distance from the first pivot pin 26 and causing the lever's drive end 22 to shift downward, transmitting a downward driving force to the drive member 50 through the drive pin 23 linking the lever 21 to the drive shaft 51 and forcing the drive member 50 to shift linearly toward the distal end of the instrument. A biasing member in the form of a wishbone spring 19 is fixed to the lever 21 and instrument body 10 by screws 183 and biases the lever 21 away from the instrument body 10 so that releasing the actuator lever 21 automatically retracts the drive member 50 to a starting position.

A limiting element, such as inhibitor switch 30, optionally may be provided to selectively limit the motion of the drive member 50 at one or more predetermined points to enable movement of the drive member 50 to a plurality of predetermined positions during operation of the actuator depending on the position of the inhibitor switch. Inhibitor switch 30 passes through an aperture 39 in a side of the instrument body 10 and opening into the bore 17 therein. The switch 30 is held in the aperture 39 by a pin 37 inserted into the aperture 39 and disposed in an annular recess 31 in the body of the switch 30. The pin 37 prevents axial movement of the switch 30 with respect to the aperture 39, but permits rotation of the switch. The position or orientation of the switch may be maintained with a detent mechanism. A detent mechanism is shown in FIG. 4 in the form of a switch lever 33 and a corresponding axial detent groove 34 along the instrument body.

The inserted end of the inhibitor switch 30 is disposed in an axial recess 55 of the drive member 50. The axial recess 55 ends in an abutment flange 56 located at the proximal end of the drive member 50. The drive member abutment flange 56 abuts an off-center inhibitor flange 32 of the inhibitor switch 30 to limit movement of the drive member. Since the inhibitor flange 32 of the switch 30 is off-center, rotation of the switch 30 to a first position shifts the inhibitor flange 32 toward the proximal end of the instrument and closer to the drive member abutment flange 56, limiting axial shifting of the drive member 50 to a first distance. Rotation of the switch 30 to a second position shifts the inhibitor flange 32 toward the distal end of the instrument, allowing the drive member 50 to shift a second distance greater than the first distance. Of course, different configurations of limiting elements are possible, and additional predetermined inhibiting positions are possible.

It is also possible to limit motion of the actuator and/or drive member using other limiting elements, such as a ratchet mechanism that allows for sequentially increasing movement of the drive member upon shifting the actuator a predetermined number of times. An example of such a ratchet mechanism is discussed below in more detail in connection with other embodiments of instruments.

Figure 9:
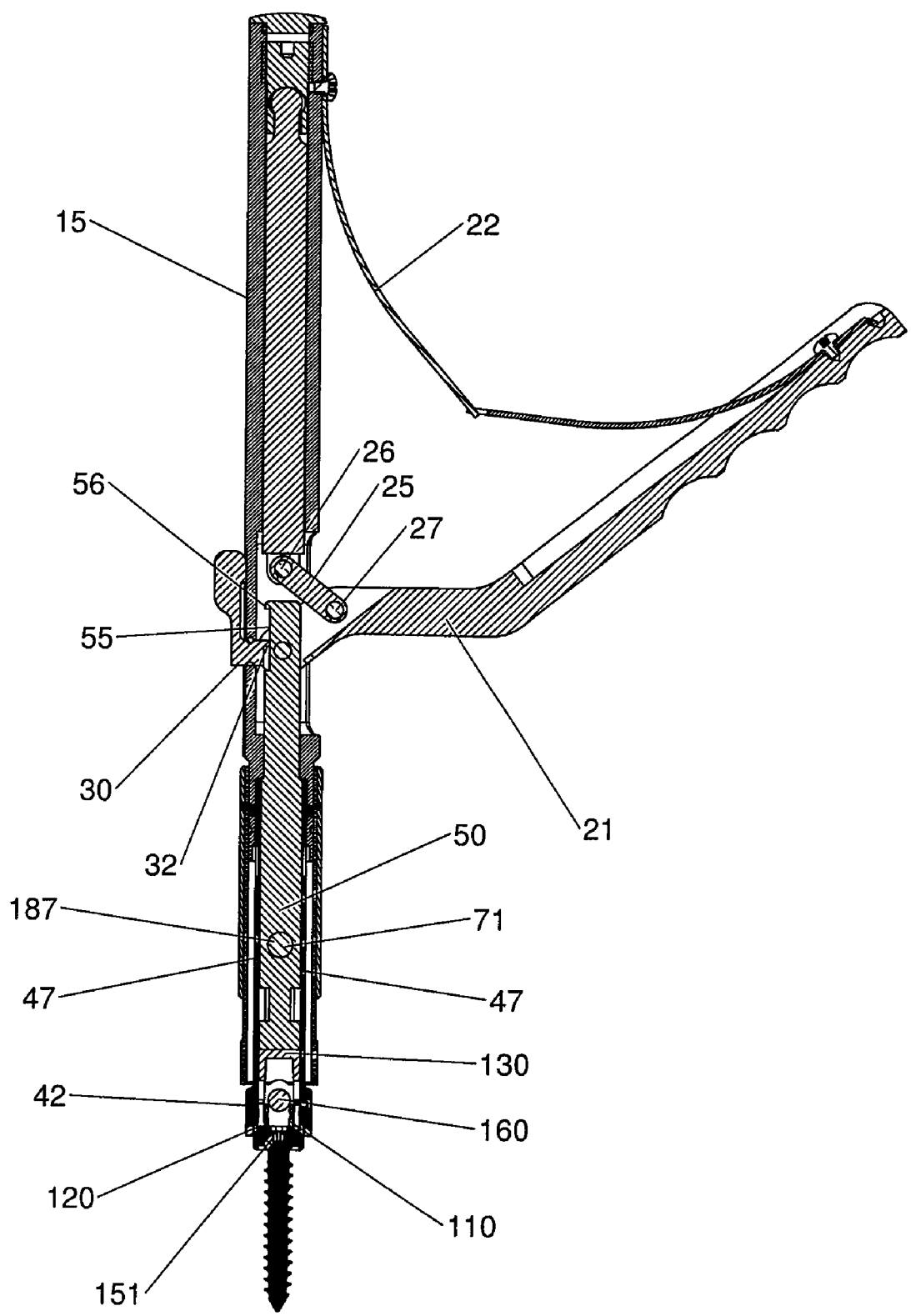
FIGS. 9a-9c are sequential cross-sectional views demonstrating operation of the drive member to advance the cap member into the coupling assembly.
Figure 9:
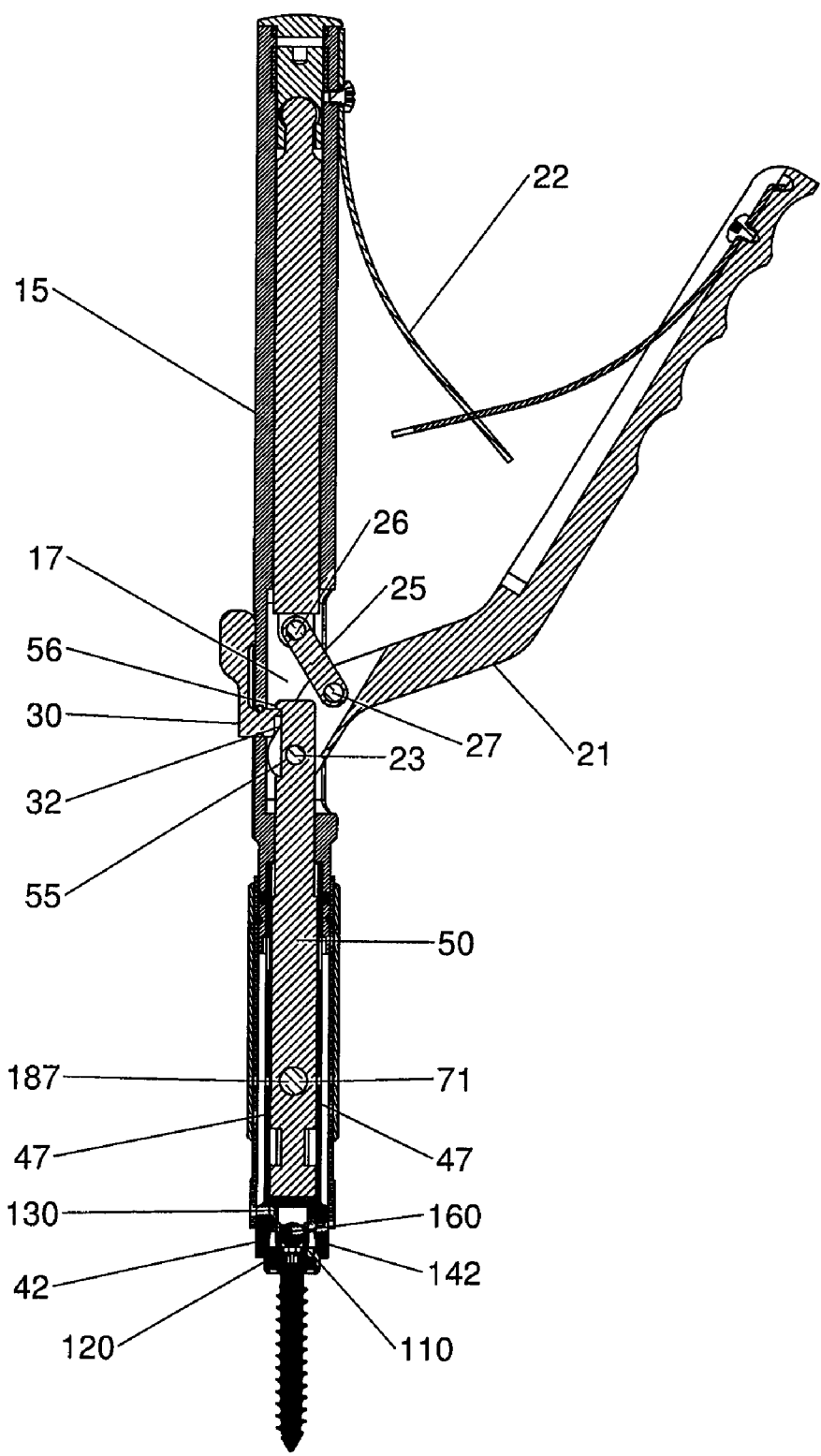
Figure 9:
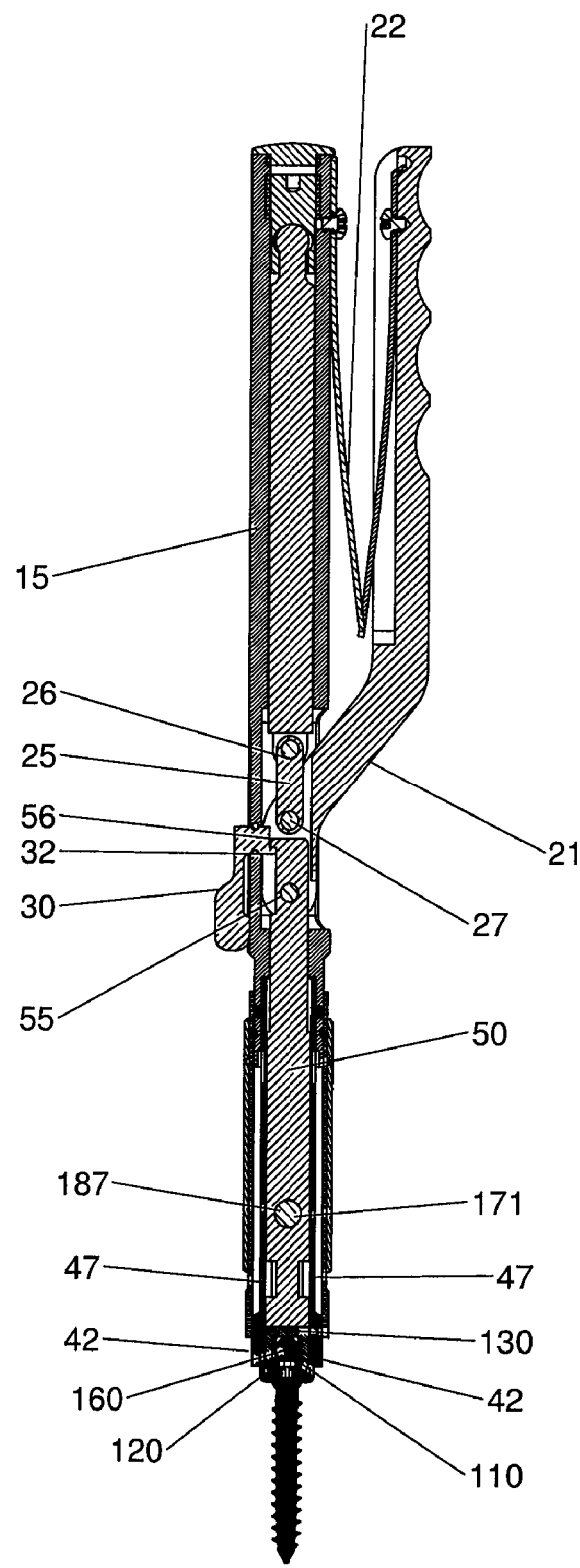

In order to secure the rod 160 in a coupling device 100, the rod is arranged in or above the rod-receiving channel 119 of the assembly as illustrated in FIG. 9a. The rod-receiving channel is formed by upstanding arms 113 of the insert member 110. The instrument 1 is loaded with a cap member 130 held by the head 52 of the drive member 50. The instrument 1 is then clamped to the coupling device 100 with the rod 160 received therein so that the drive member 50 axis is aligned with the assembly 100 and rod 160. The drive member 50 and the grasping device 40 cooperate to secure the coupling device 100, advance the cap member 130 into the assembly, and lock the rod 160 in place within the assembly.

Figure 10:
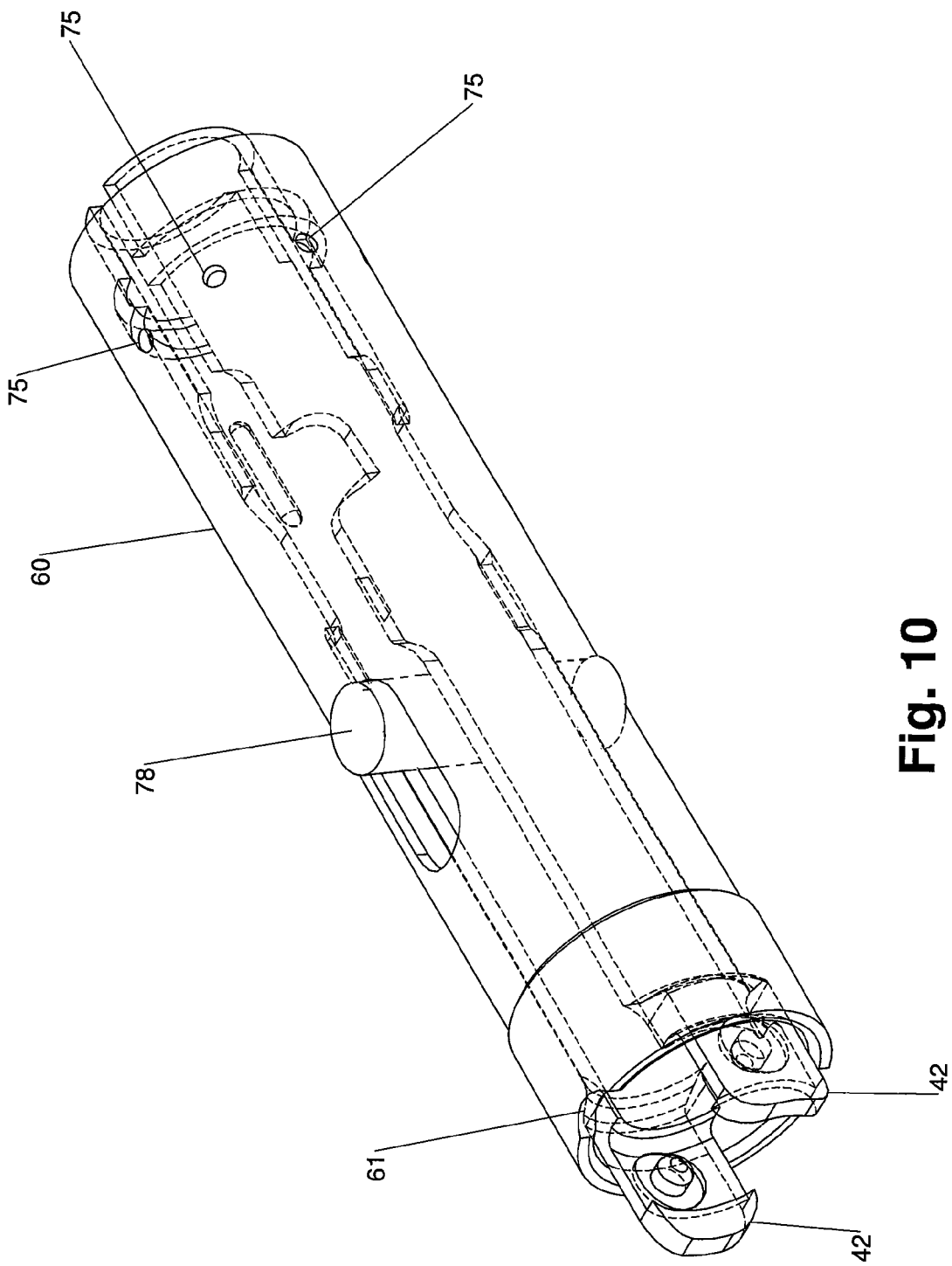
FIG. 10 shows a reducing sleeve portion of the instrument of FIGS. 1-4.
Figure 11:
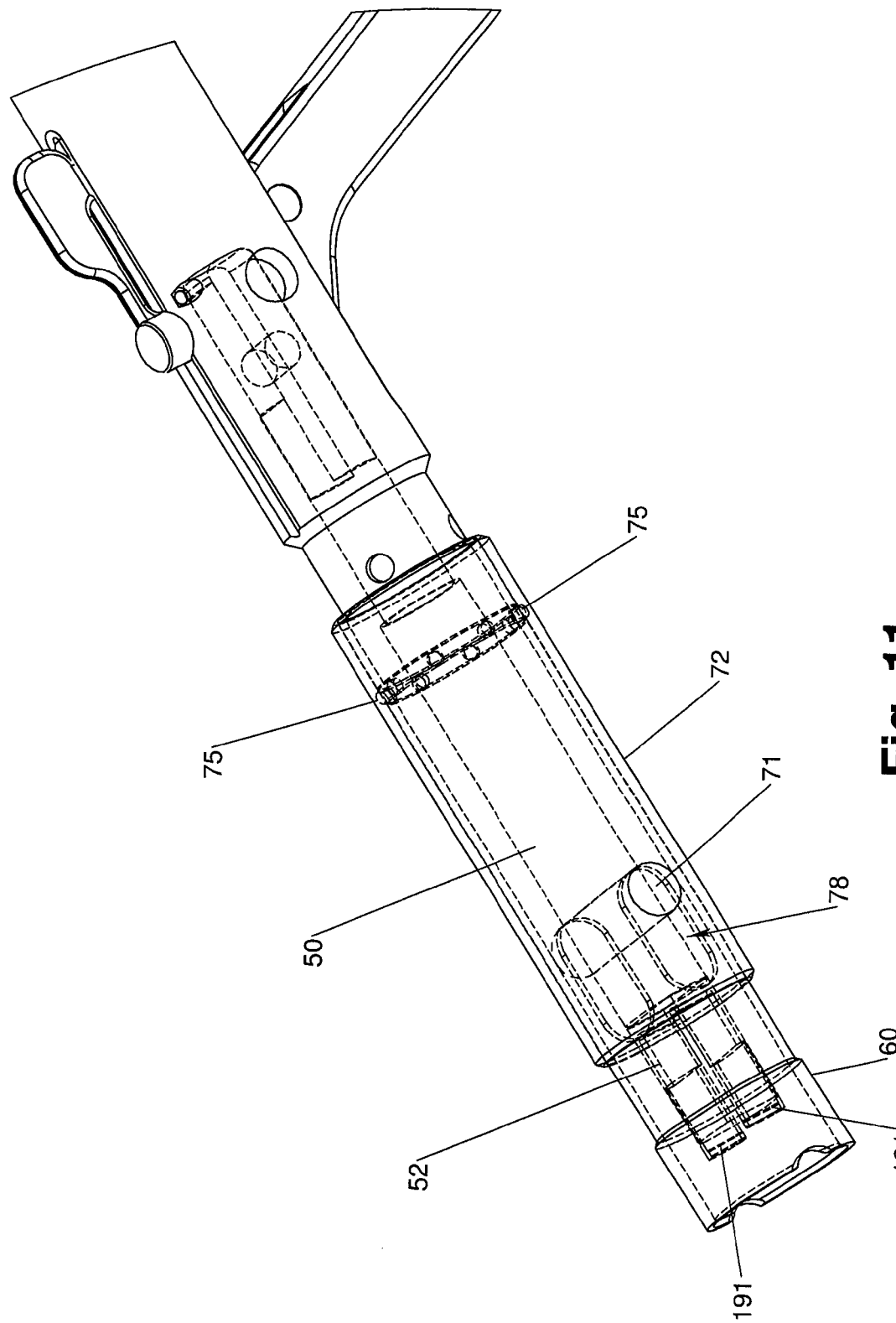
FIG. 11 shows a drive coupler for coupling movement of the drive member to movement of a reducing sleeve in FIG. 10.

Since the rod is locked into place by axial insertion of the cap 130 into the coupling assembly, the rod 160 is preferably properly seated in the coupling device 100 prior to insertion of the cap. Therefore, a separate reducing member may be provided to apply downward force upon the rod at spaced positions along the rod's length, outside the area in which the rod 160 is contacted by the cap 137, in order to aid in fully seating the rod 160 in the rod-receiving channel 119 (often referred to as "reducing" the rod) before and during cap insertion without obstructing the cap insertion path. Such a reducing member also serves to stabilize the rod during reduction. For instance, FIG. 10 shows a reducing member 60 in the form of a sleeve disposed about the grasping member 40. The reducing sleeve 60 may have arcuate rod engaging recesses 61 at radially-opposed positions on its distal end, with the recesses 61 contoured to mate with the surface of the rod 160.

After securing the coupling device 100 within the grasping device 40, the cap member 130 and rod 160 are advanced toward the assembly as shown in FIG. 9b. As the drive member 50 travels downward through the bore 17 toward the coupling device 100, a bottom face 137 of the cap member 130 is driven into contact with the rod 160, forcing the rod to a fully seated position within the rod-receiving channel 114 of the assembly. As the legs 132 of the cap 130 are inserted into the outer body 120 of the assembly, wedge shaped insertion portions 133 of the cap having outwardly-directed retention flanges 135 slide past provisional locking flanges 125 in the outer body member 120. The mating of the retention flanges 135 and the provisional locking flanges 125 allows the cap to be further inserted into the body member 120 but prevents backward movement of the cap member 130. In this provisional locking position (FIG. 9b) the rod 160 may be manipulated to shift and rotate in the rod-receiving channel 119, but is prevented from fully escaping the assembly in a direction transverse to its axis.

Further travel of the drive member 50 forces the legs 132 of the cap 130 fully into the assembly to achieve a full locking position as shown in FIG. 9c. In the full locking position, widened locking portions 134 of the legs are wedged between the upstanding arms 113 of the insert member 110 and the inner surface of the body member 120, laterally shifting the insert member arms 113 slightly toward one another, forcing the insert member arms 113 against the spinal rod 160 and providing a friction lock that secures the outer body member 120, cap member 130, insert member 110, and rod 160 together. The instrument may be disengaged from the assembly 100 after provisional locking, or may be used to immediately fully lock the rod 160.

In order to allow a single actuator system to achieve the discrete provisional locking and full locking positions, the inhibitor switch 30 described above in connection with the actuator subassembly may be configured to allow the cap member 130 to be driven only into the provisional locking position when the switch 30 is in a first position, and to allow the cap member 130 to be driven into the full locking position when the switch 30 is in a second position. Alternatively, the inhibitor switch may be omitted altogether.

Figure 12:
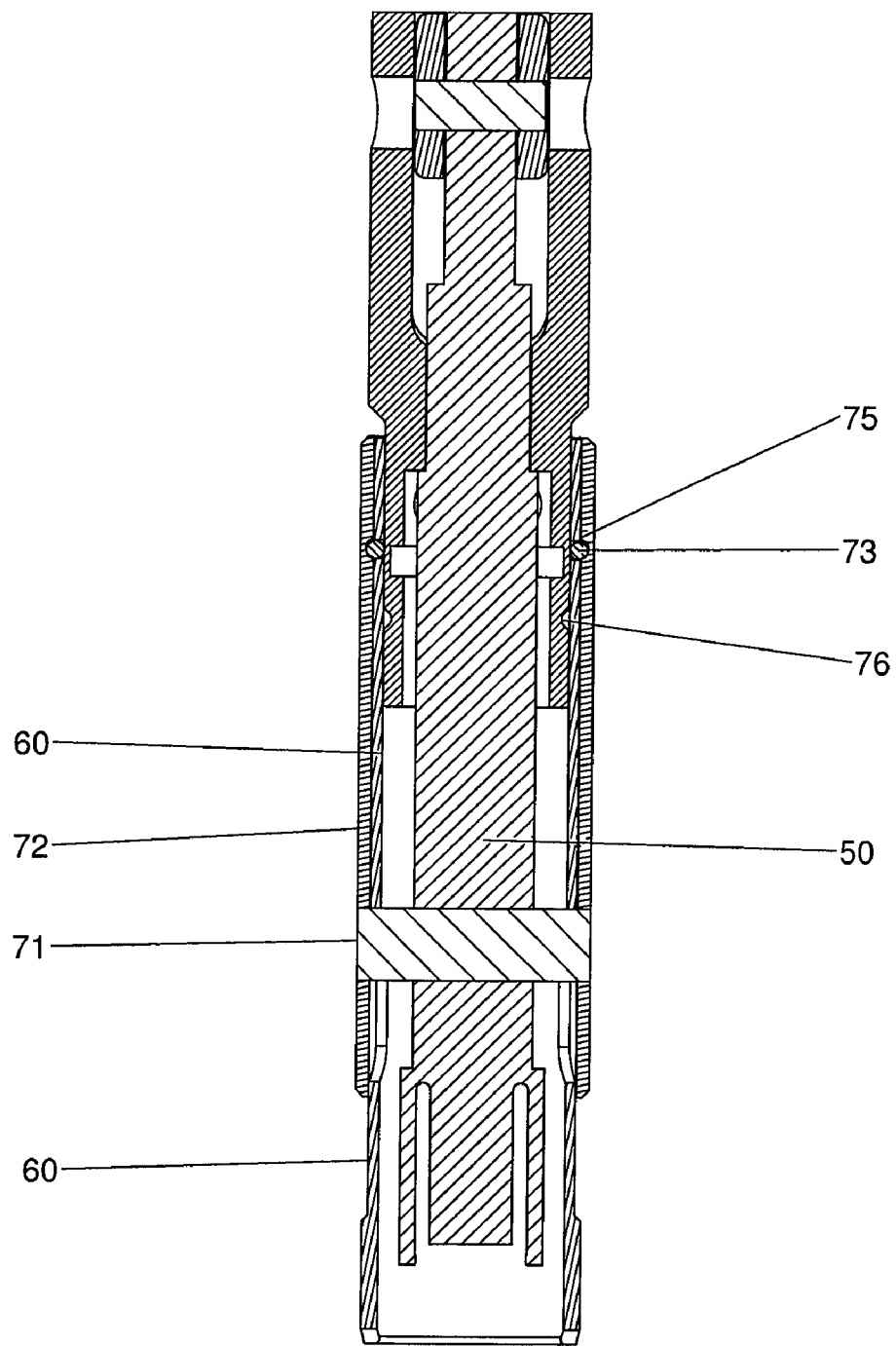
FIGS. 12a-12d are sequential cross-sectional views demonstrating coupling and decoupling of a drive member and reducing sleeve.
Figure 12:
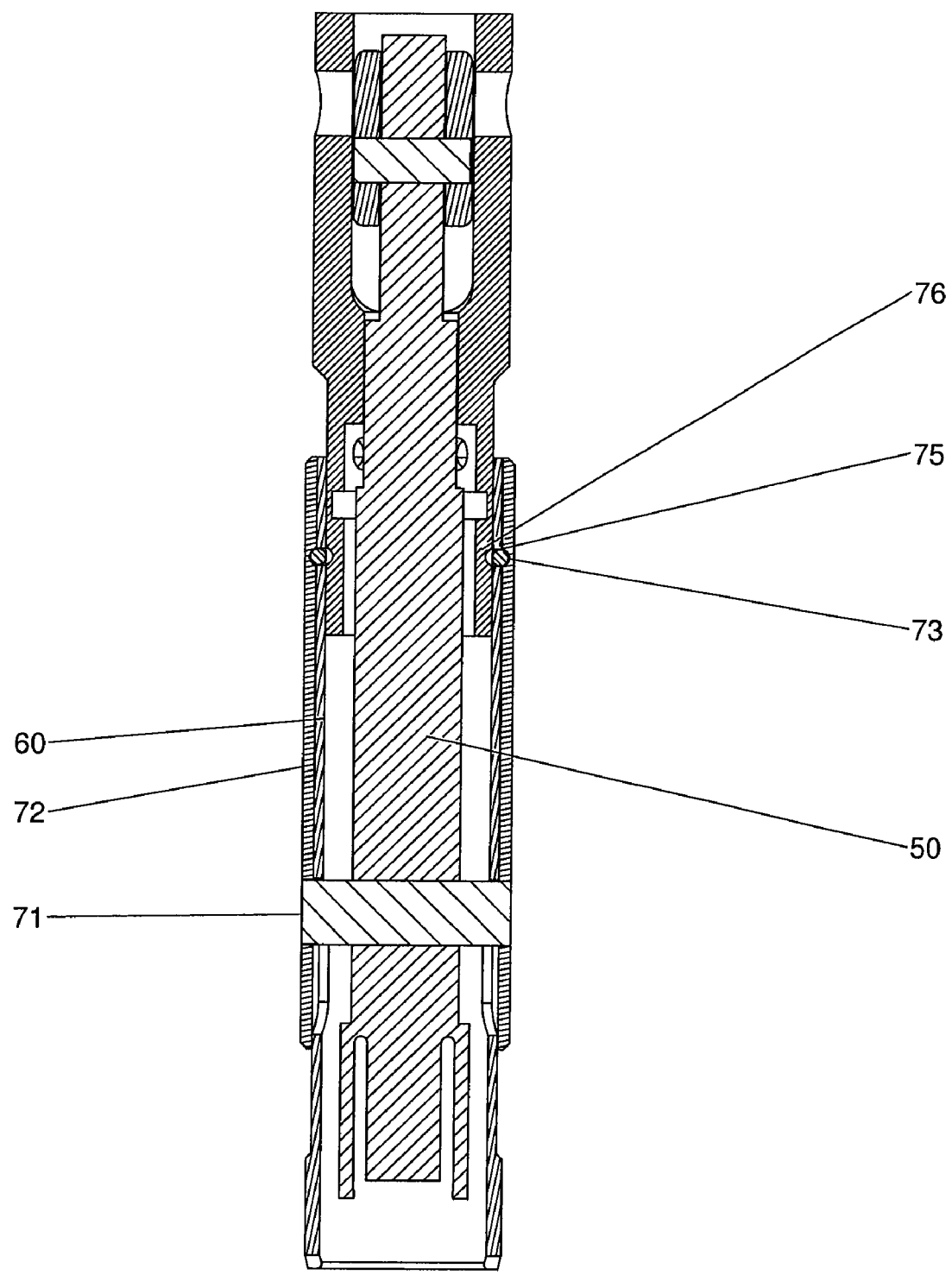
Figure 12:
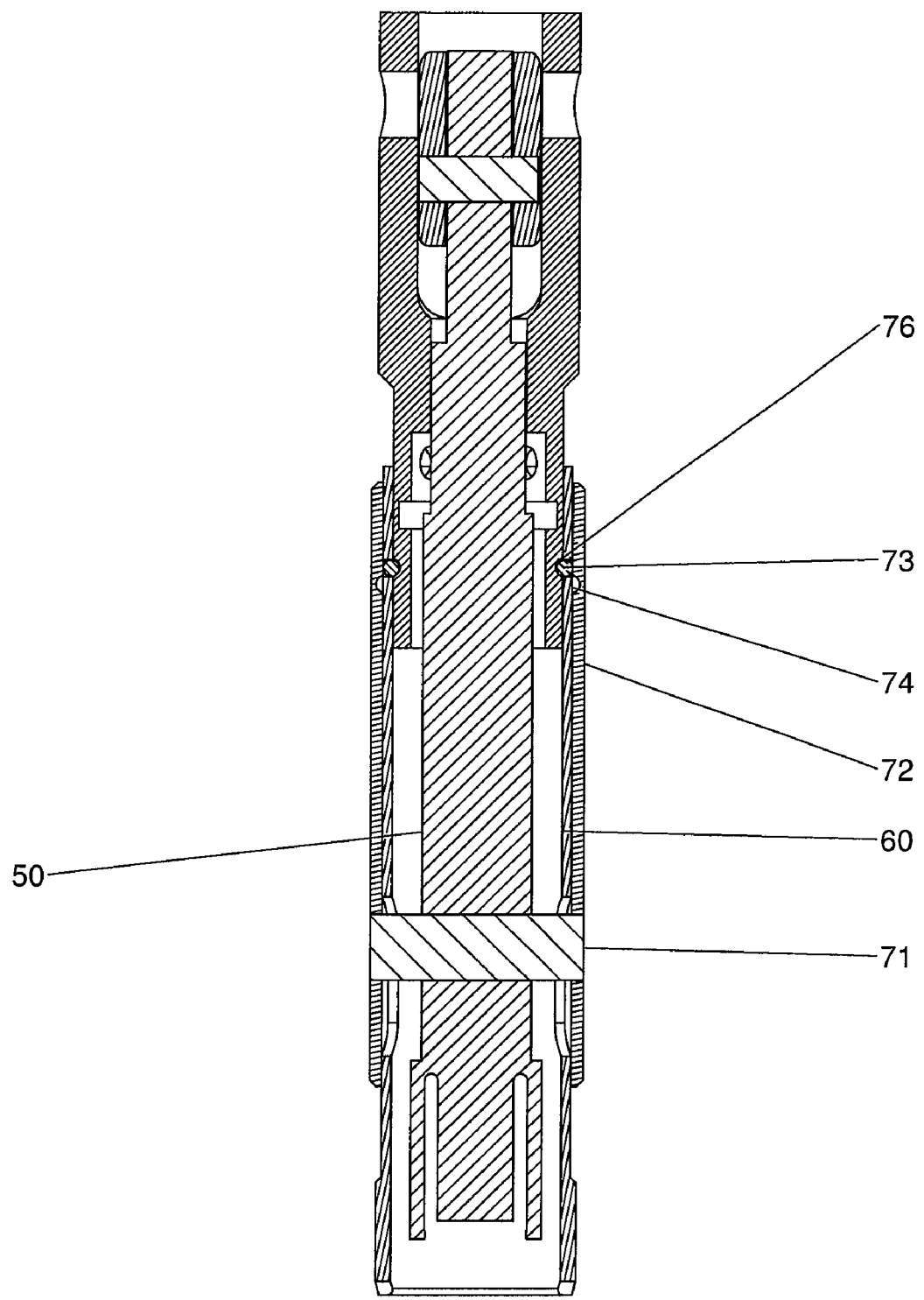
Figure 12:
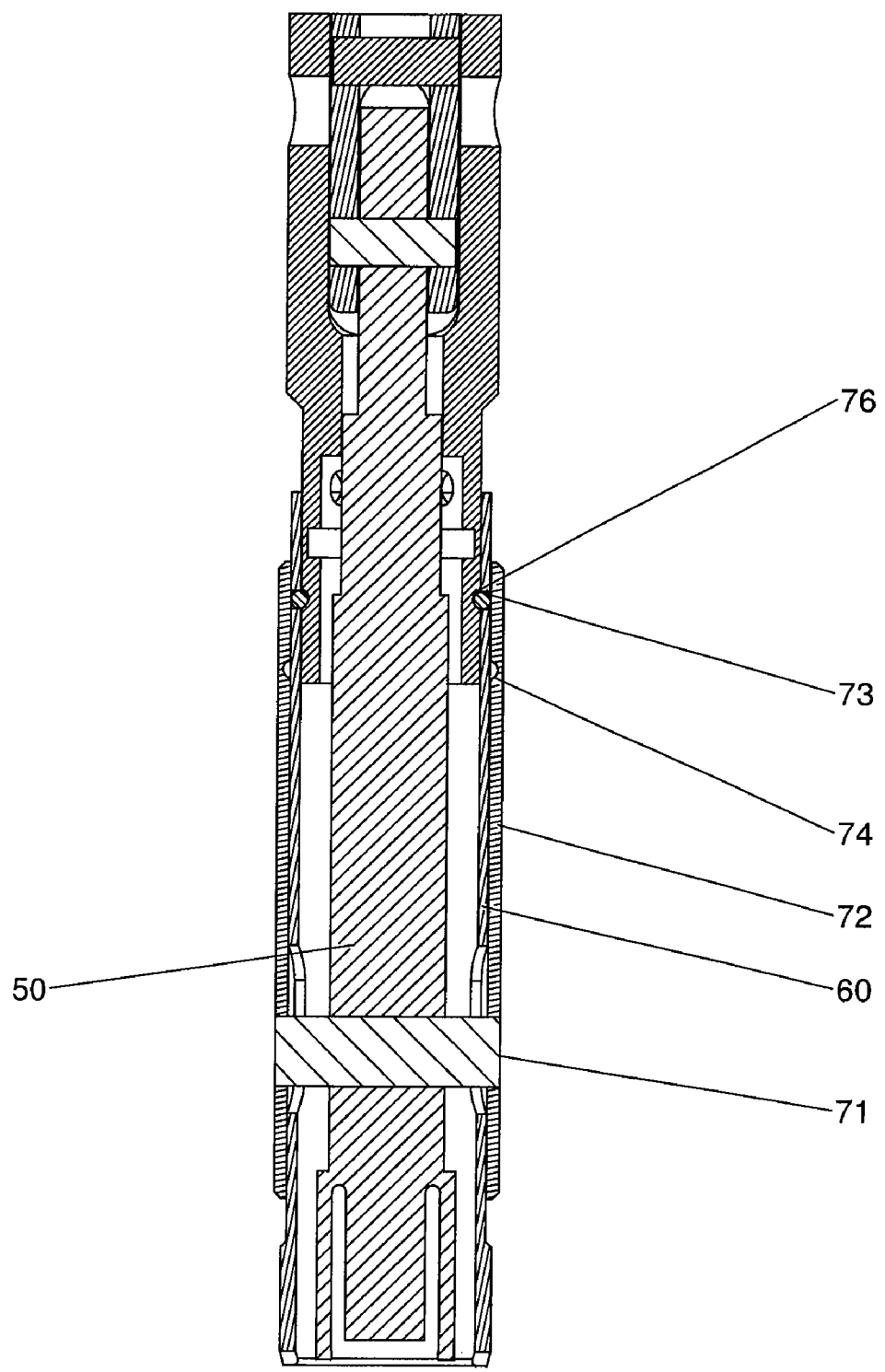

In order to shift the reducing sleeve 60 into contact with the spinal rod 160 and eventually reduce the rod into the coupling device 100, the reducing sleeve 60 may advantageously be operatively coupled to the drive member 50. In order to allow the drive member 50 to continue to shift after the reducing sleeve 60 has fully reduced the rod 160, the reducing sleeve 60 may be coupled indirectly to the drive member 50. In the illustrated embodiment, the reducing sleeve 60 is coupled to the drive member 50 via a coupling sleeve 72 and coupling pin 71, with the coupling sleeve releasably coupled to the reducing member 60 via a plurality of shifting elements 73. The shifting elements are partially housed in a plurality of apertures 75 spaced circumferentially about the proximal end of the reducing member 60. As the reducing member 60 and coupling sleeve 72 shift along the instrument axis, the apertures 75 in the reducing sleeve become aligned with an outer annular recess 76 in the instrument body 10 and/or an inner annular recess 74 in the inner surface of the coupling sleeve. The shifting elements 73 are always partially located in the reducing sleeve apertures 75, but are large enough to extend through the apertures 75 and into either of the coupling sleeve recess 74 or the annular body recess 76. When reducing sleeve 60 is in a proximal or starting position as in FIG. 12a, the shifting elements 73 abut an exterior surface portion 14 of the instrument body, forcing the shifting elements 73 into the reducing sleeve apertures 75 and the annular coupling member recess 74. In this position, where the shifting elements 73 are shared between the apertures 75 and the annular coupling sleeve recess 74, the reducing sleeve 60 is coupled to the coupling sleeve 72 and therefore shifts along with drive member 50. However, when the reducing member shifts toward the distal end of the instrument 1 and is at a position where the rod 160 is fully reduced in the insert 110 of the coupling assembly, the annular coupling sleeve recess 74, reducing sleeve apertures 75, and annular body recess 76 are all aligned, allowing the shifting elements 73 to shift into the instrument body annular recess 76, as shown in FIGS. 12b and 12c. The recess in the coupling sleeve 72 is configured to match the surface of the shifting elements 73 so that the shifting elements will be biased toward the body recess 76. When the shifting elements 73 shift from the annular coupling sleeve recess 74 to the annular recess 76 in the fixed instrument body 10, so that the shifting elements 73 are disposed in the reducing sleeve apertures 75 and body recess 76 (FIG. 12c) instead of in the reducing sleeve apertures 75 and coupling sleeve recess 74 (FIG. 12b), the reducing sleeve 60 becomes coupled to the fixed body portion 10 instead of the drive member 50. At this point, the drive member 50 is allowed to continue to shift downward without movement of the reducing sleeve 60. The elongate openings 78 in the reducing sleeve 60 allow the coupling pin 71 and the drive member 50 through which it extends to continue to advance without interference from the reducing sleeve 60, which at this point has fully reduced the rod 160 into the insert member 110 of the coupling assembly. The shifting elements 73 of the coupling device are decoupled from the body recess 76 when the drive member 50 retracts and the coupling pin 71 exerts upward force on the slot 78 in the reducing member 60, forcing the reducing member 60 upward and causing the shifting elements 73 to move radially outward and back into engagement with the coupling sleeve 72, once again coupling the reducing sleeve to the coupling sleeve and drive member.

Figure 13:
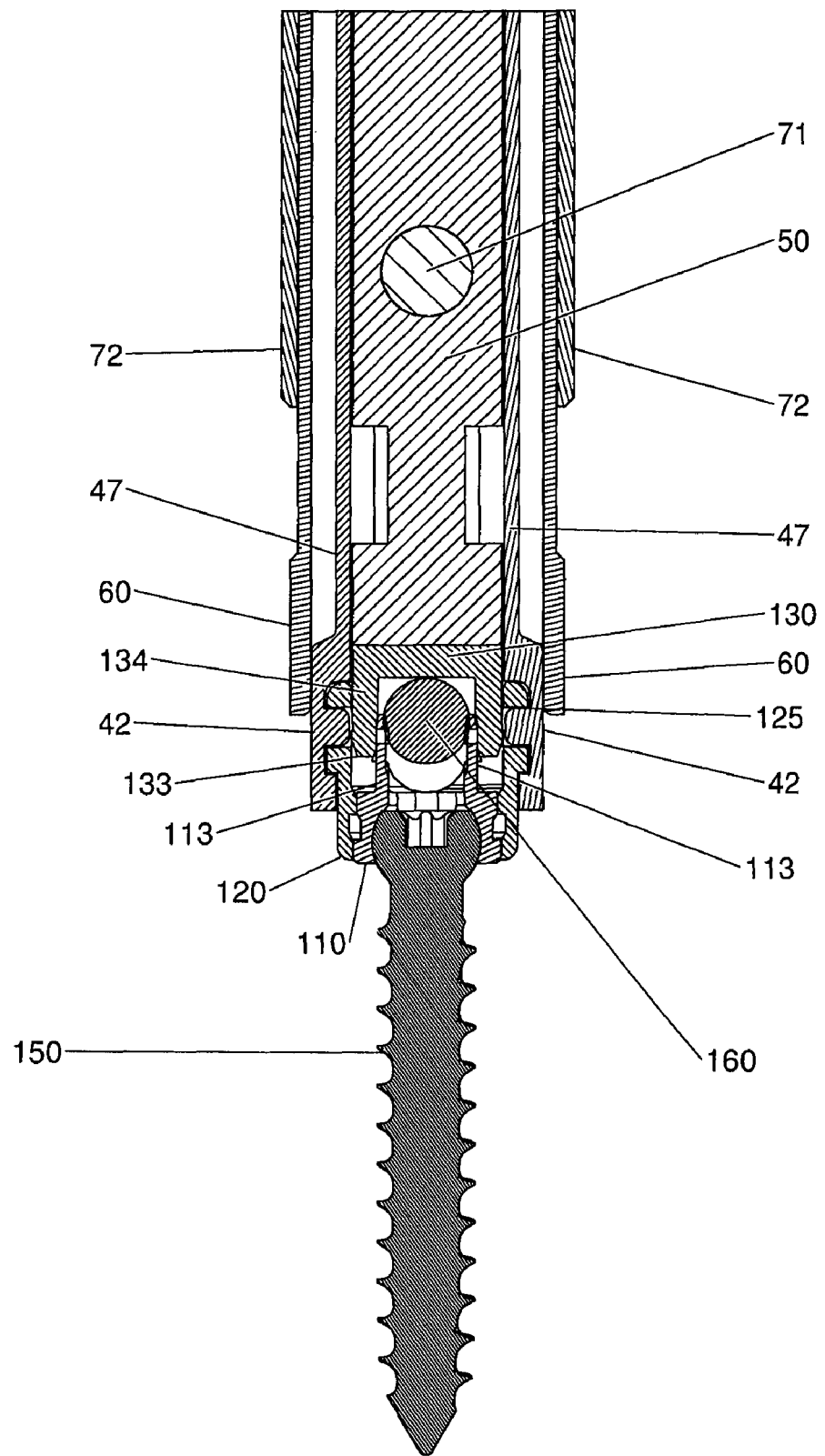
FIGS. 13a and 13b are sequential cross-sectional views demonstrating locking of a cap member to a coupling assembly already fully locked to an anchor member.
Figure 13:
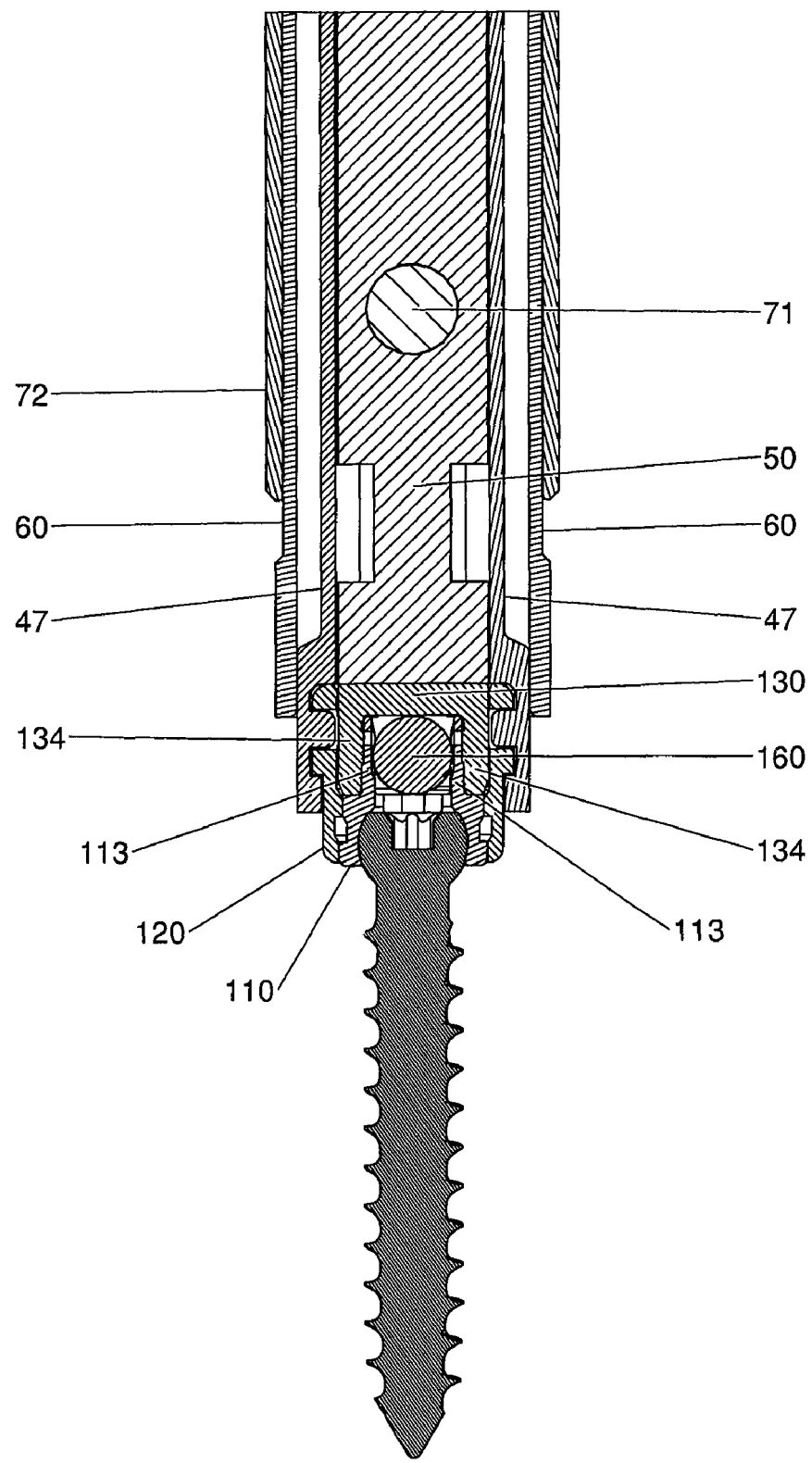
Figure 14:
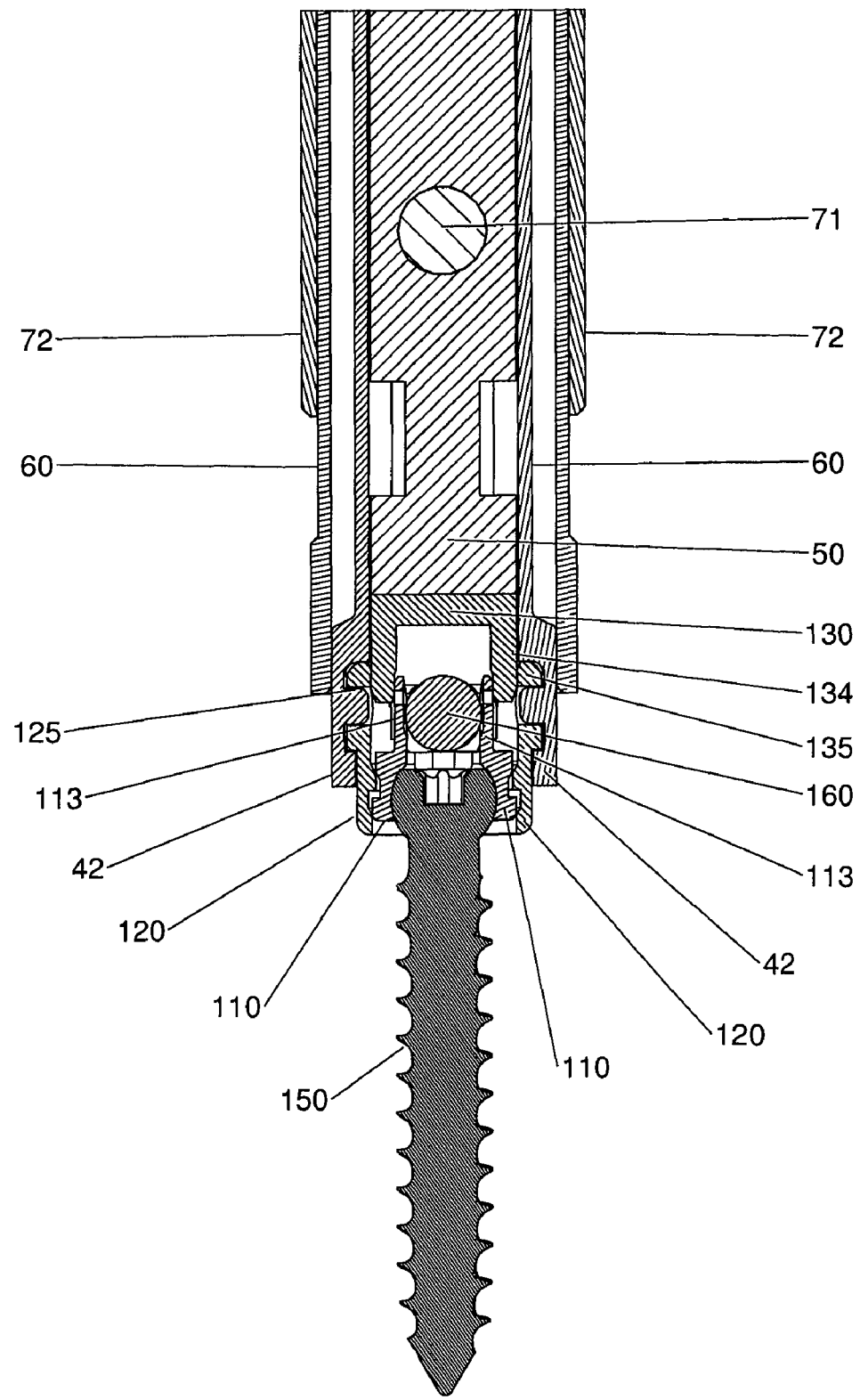
FIGS. 14a-14c are sequential cross-sectional views demonstrating locking of a cap member to a coupling assembly provisionally locked to an anchor member.
Figure 14:
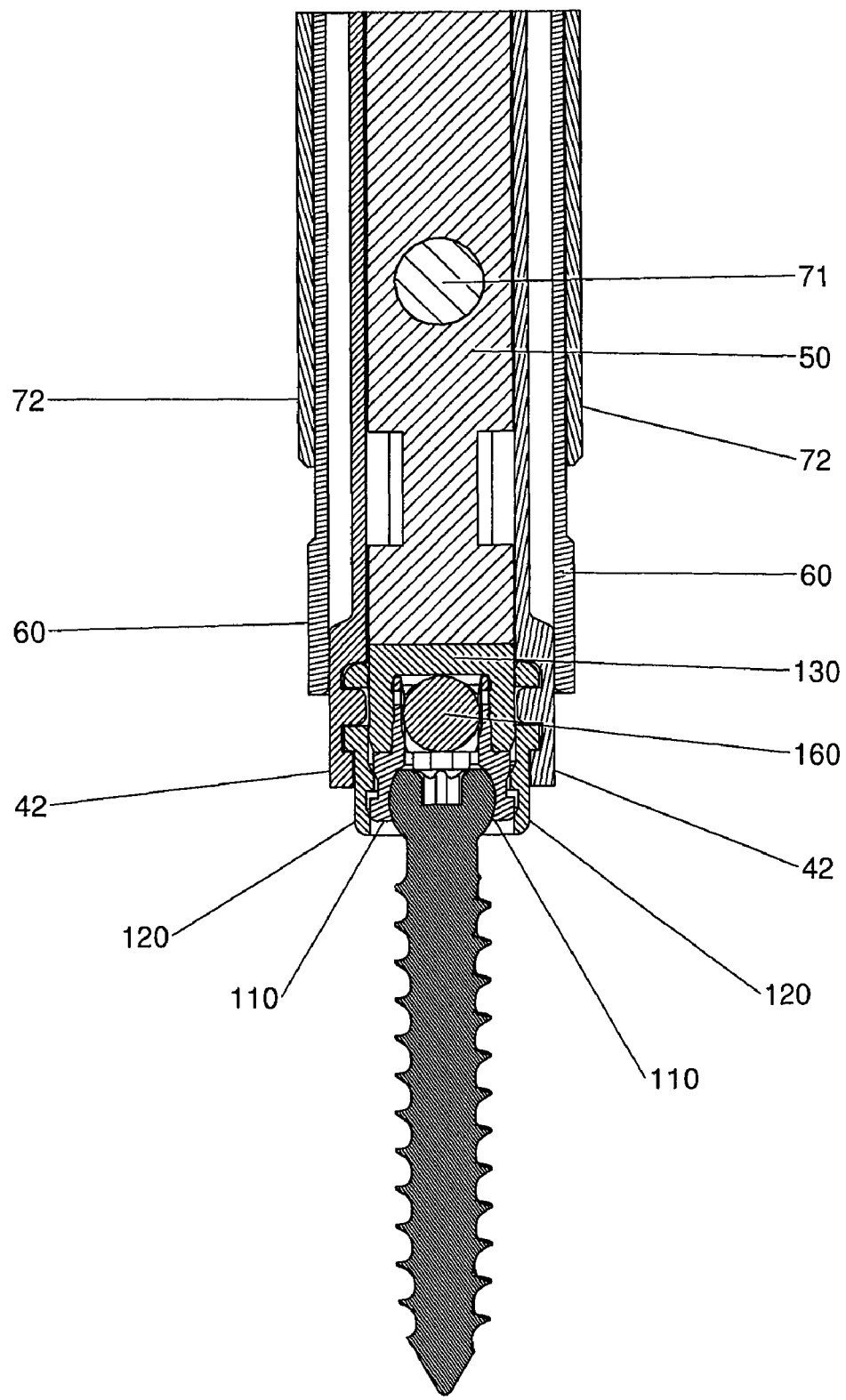
Figure 14:
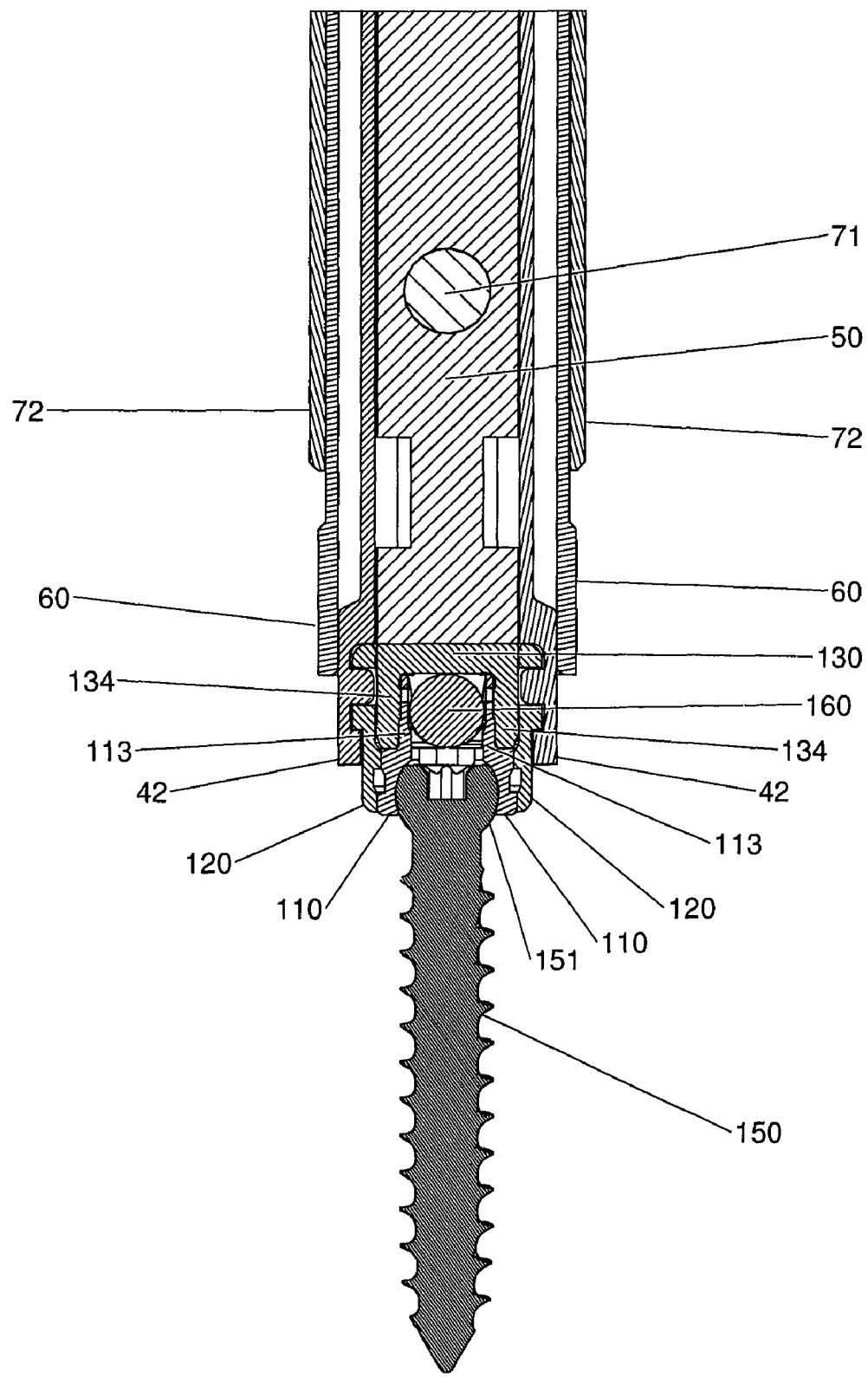

The aforementioned operation of the instrument may be used to lock the cap member 130 and rod 160 into a pedicle screw assembly already fully locked with respect to its anchor member (e.g. pedicle screw 150), or may be used to fully lock both the anchor member and cap member to the assembly. FIGS. 13a and 13b demonstrate securing a cap member 130 to a locked assembly, wherein the insert member 110 is fully seated in the outer tulip body 120 so that the lower portion 112 of the insert 110 is compressed about the screw head 151 so that the screw shank 152 extends from the coupling device 100 at a fixed angle. The cap member 130 is advanced linearly from the provisional locking position (FIG. 13a) to the full locking position (FIG. 13b). Alternatively, as shown in FIGS. 14a-c, the cap member 130 may be inserted into the coupling device 100 when the coupling assembly is in the provisional screw lock position. In the provisional screw lock position (FIGS. 14a and 14b), the insert member 110 is not fully seated and compressed within the outer tulip body 120, so that the screw head 151 is retained within the assembly 100 but may still pivot with respect thereto. As the cap is advanced into the assembly, the cap first reaches a position wherein the legs 132 of the cap are disposed between the arms of the coupling assembly insert member 110 and outer member 120. Subsequently, further advancement of the drive member 50 drives the cap member 130 against the insert member 110, forcing the insert member 110 further into the outer tulip body 120 and into a full screw locking position as previously described, wherein the radial protrusion on the inner surface of the tulip body 120 applies an inward compressive force upon the flexible lower portion 112 of the insert member, locking the screw head 151 disposed in the insert member lower portion 112 at a fixed angle with respect thereto (FIG. 14c). At this point, both the spinal rod and screw head are fully locked into position. If desired, the inhibitor switch 30 discussed above may be configured to provide discrete stopping points of the actuator corresponding to provisional rod lock with provisional screw lock (FIG. 14a), abutment of the insert member with the cap (FIG. 14b), and full rod lock with full screw lock (FIG. 14c).

Figure 15:
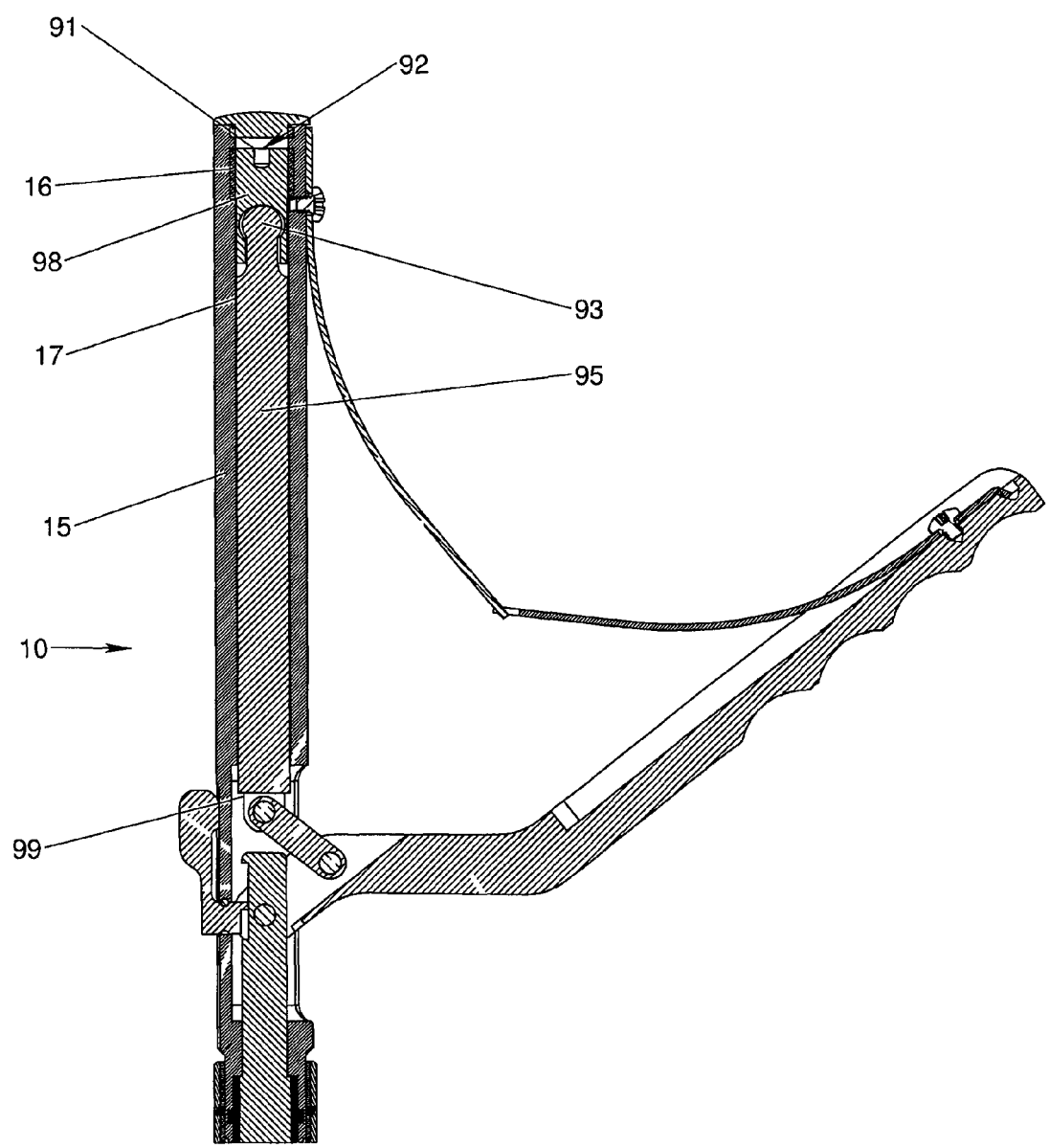
FIG. 15 is a magnified view of an adjustment device of an instrument.

In order to allow for adjustment of the starting and stopping positions of the drive member, an adjustment device may optionally be included in the instrument. One such adjustment device 90, disposed in the handle 15 of the instrument body 10, is shown in FIG. 15. The adjustment device 90 includes an interface member 91 for interfacing with a tool. The exemplary interface member 91 includes a slotted drive interface 92 for receiving a flat driver tool, although other configurations are possible. The interface member 91 also includes a threading 93 on its exterior matching interior threading 16 in a portion of the throughbore 17 of the handle 15. The interface member 91 is rotatably coupled to an adjustment shaft 95. A proximal spherical end 96 of the adjustment shaft 95 is received in a socket 94 of the interface member 91. The distal end 99 of the shaft 95 includes openings 198 to receive a pin 26 to secure the actuator subassembly pivot link 25 to the adjustment shaft 95. Rotation of the interface member 91 using an appropriate tool causes downward travel of the interface member 91 and adjustment shaft 95 through the throughbore 17 due to the threaded surfaces 93 and 16, which in turn shifts the actuator subassembly 20 downward, providing a new starting position for the moveable drive member 50 secured to the actuator subassembly 20. After adjustments are made, the throughbore 17 may be sealed by an end cap 98 in order to prevent accidental adjustment of the interface member 91.

Another exemplary instrument according to the invention herein is depicted in FIGS. 16-21. In many aspects this instrument is similar in design and operation to the instrument previously disclosed. However, certain differences are provided, as will be described herein below. Aspects of specific components of the instrument 201 could be adopted individually for use in the instrument 1 previously described if desired to provide one or more of the distinguishing features of the embodiment described below.

Figure 16:
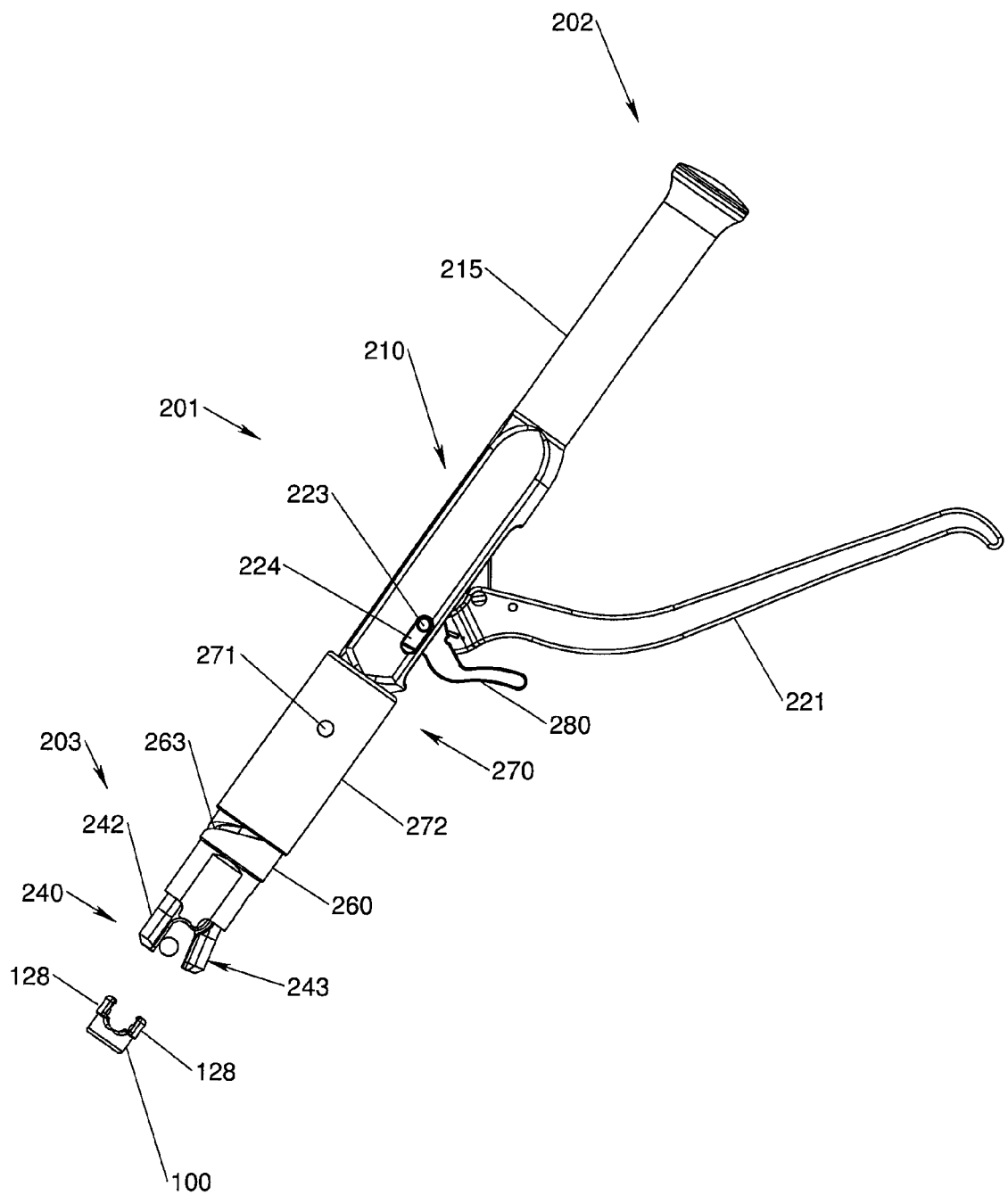
Figure 16:
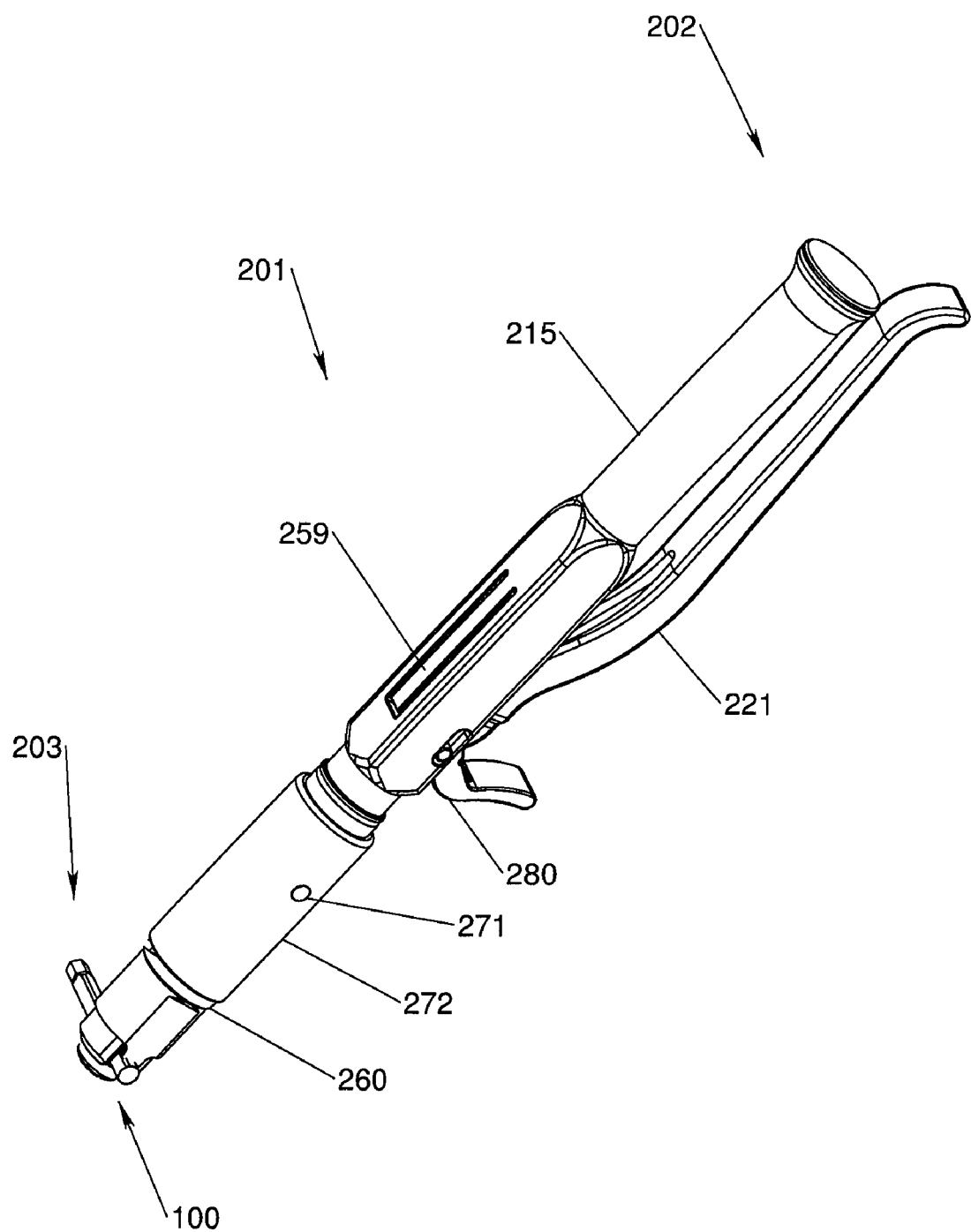
Figure 17:
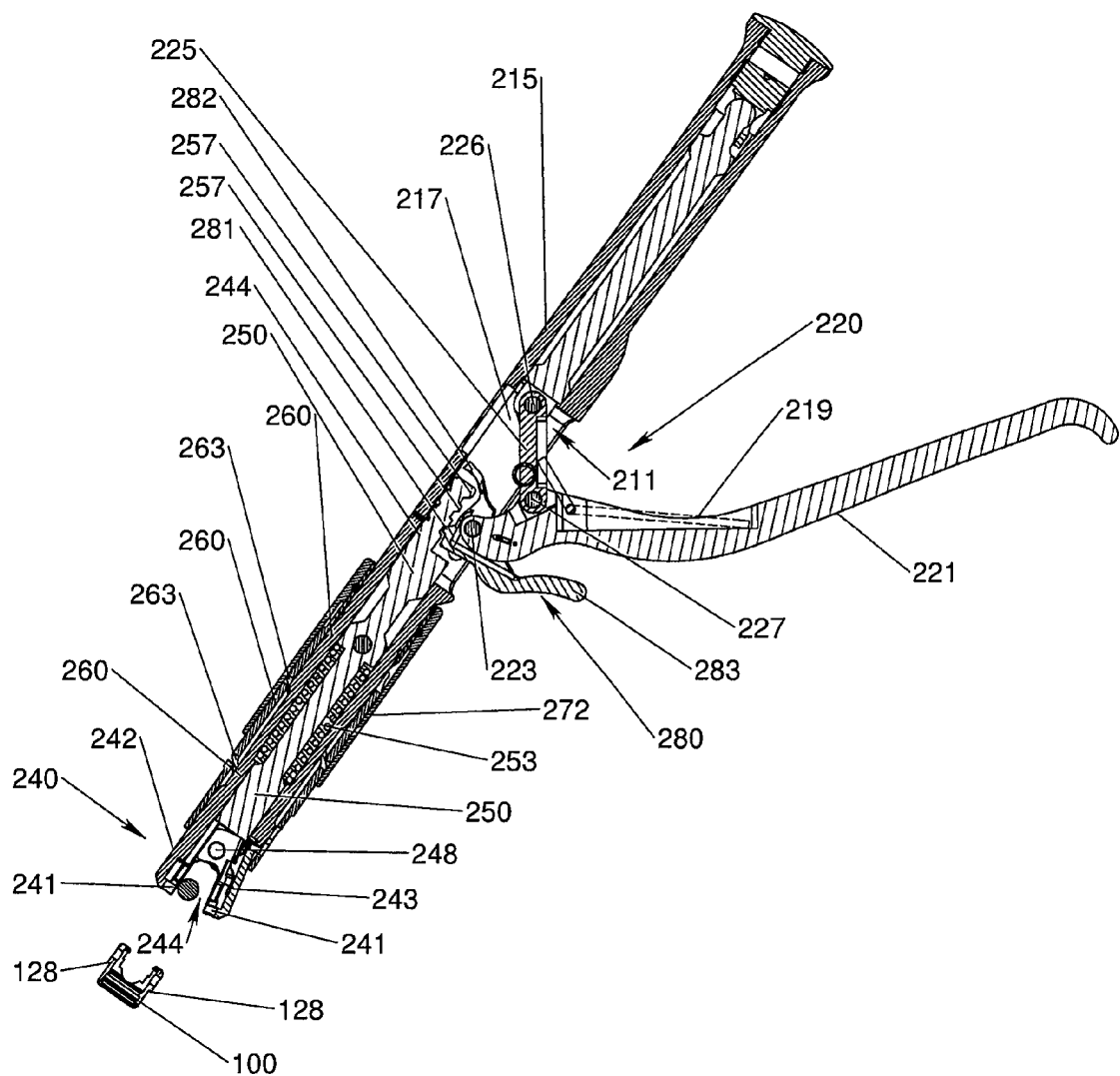
FIG. 17 is a front cross-sectional view of the instrument in FIG. 16.

Referring to FIGS. 16-17, the instrument 201 has an elongate structure with a proximal end 202 to be held by a surgeon and a distal end 203 for manipulating a coupling device with a linearly inserted locking cap, such as coupling device 100 described in more detail above. The instrument body 210 has a portion forming a handle 215 to be gripped by the surgeon, and includes an axial bore 217 running therethrough in which a drive member 250 is disposed. An actuator opening 211 on one side of the elongate instrument opens to the bore 217 and allows an actuator assembly 220 to connect to the drive rod 250 disposed within the bore 217. The exterior of the instrument is shown in FIGS. 16a-b, while internal components may be viewed in the cross-sectional view of FIG. 17. The instrument is shown partially disassembled in FIG. 18 in order to allow viewing of individual components.

A clamp device or grasping device 240 is provided at the distal end 203 of the instrument to secure the coupling device 100 to the instrument. In the illustrated embodiment, a first grasping member 242 is formed integral with the instrument body A second grasping member in the form of a pivotable jaw member 242 is also provided. Jaw member 242 is pivotably coupled to the body by a pair of swivel pins 248. The clamp device 240 receives the coupling device 100 when the jaw 243 is pivoted to an open position. Alternatively, a pair of pivotable jaw members may be provided instead of one fixed member and one pivotable member. Both the fixed grasping member 242 and pivotable jaw 243 have an inwardly-directed flange 241 configured to engage a lower surface of one of the shoulders 128 of the coupling device 100, thus securing the coupling device to the instrument (FIGS. 20a-d).

A moveable drive member 250 is disposed within the bore 217 of the instrument body 210 and the interior space 244 of the grasping device, as shown in FIG. 17. The drive member 250 includes a shaft 251 and a head portion 252 that is configured to abut against the cap member 130 of the coupling device 100. The drive member is capable of linearly advancing the cap member without rotation toward the clamp device 240 and into locking engagement with the outer member 120 and/or insert member 110 of the coupling device 100 when the coupling assembly is held in place by the clamp device 240.

Figure 18:
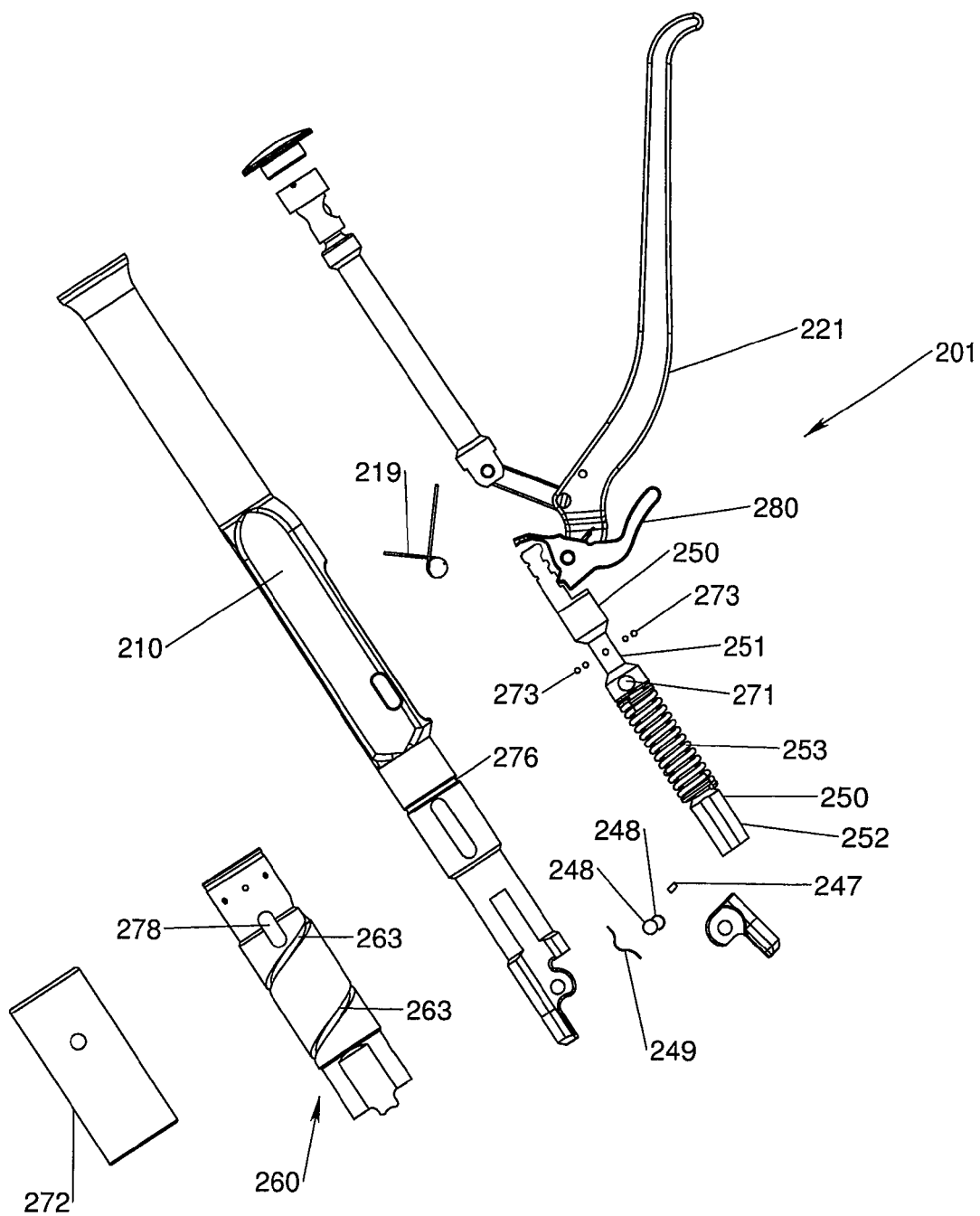
FIG. 18 illustrates the instrument of FIGS. 16-17 in a disassembled state.
Figure 19:
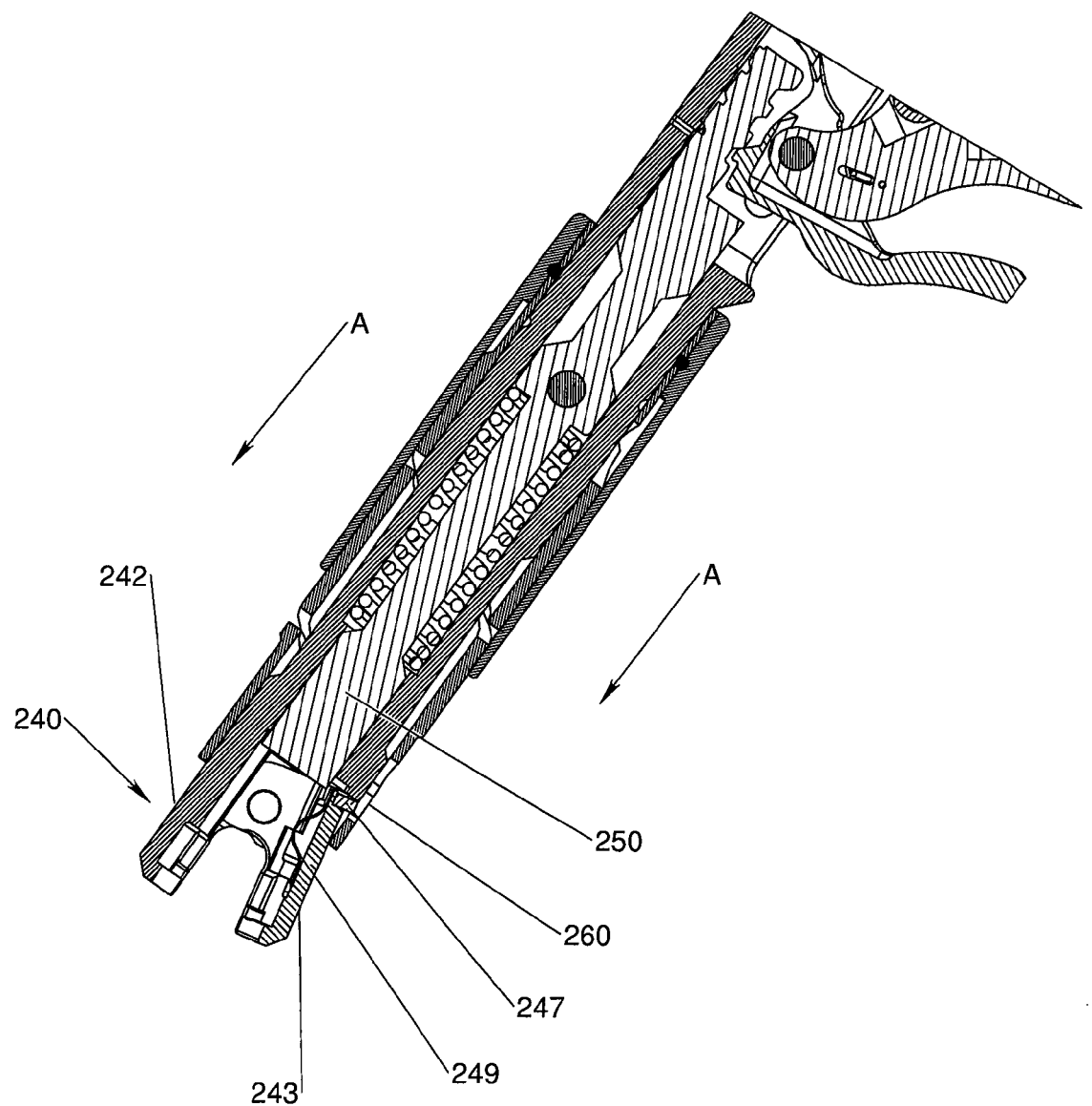
FIGS. 19a-d illustrate the opening and closing of the clamp device of FIGS. 16-18.
Figure 19:
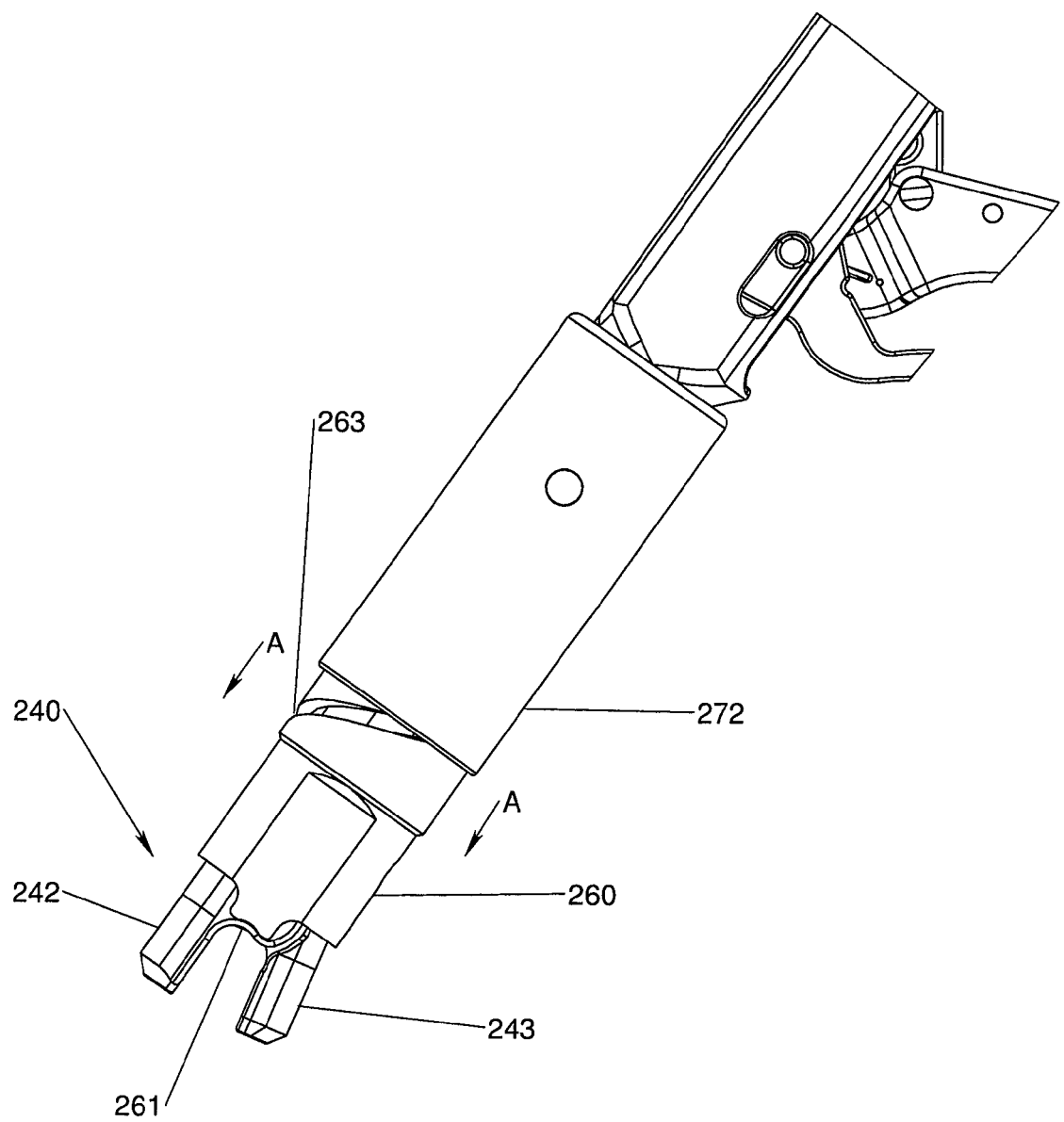
Figure 19:
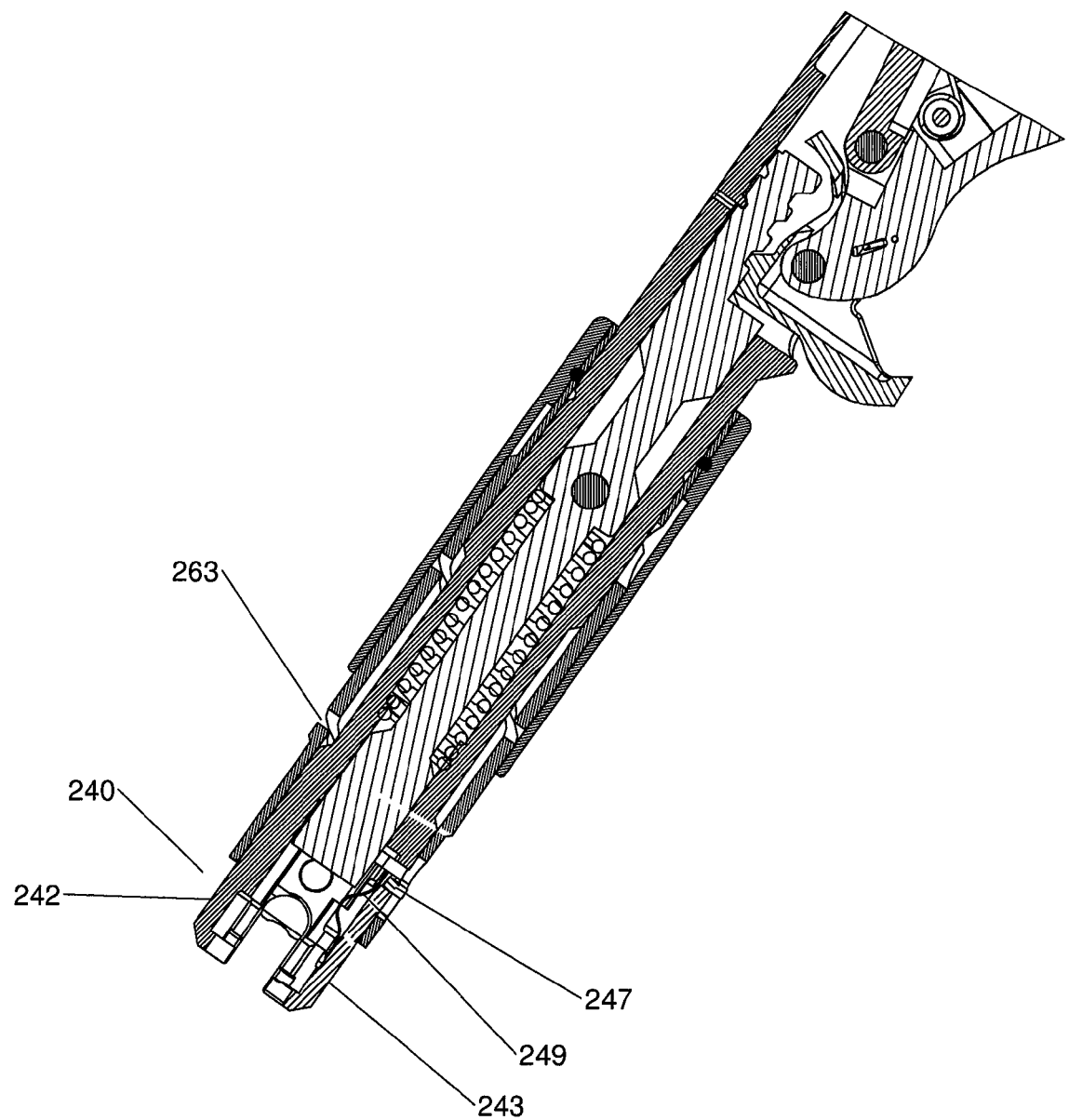
Figure 19:
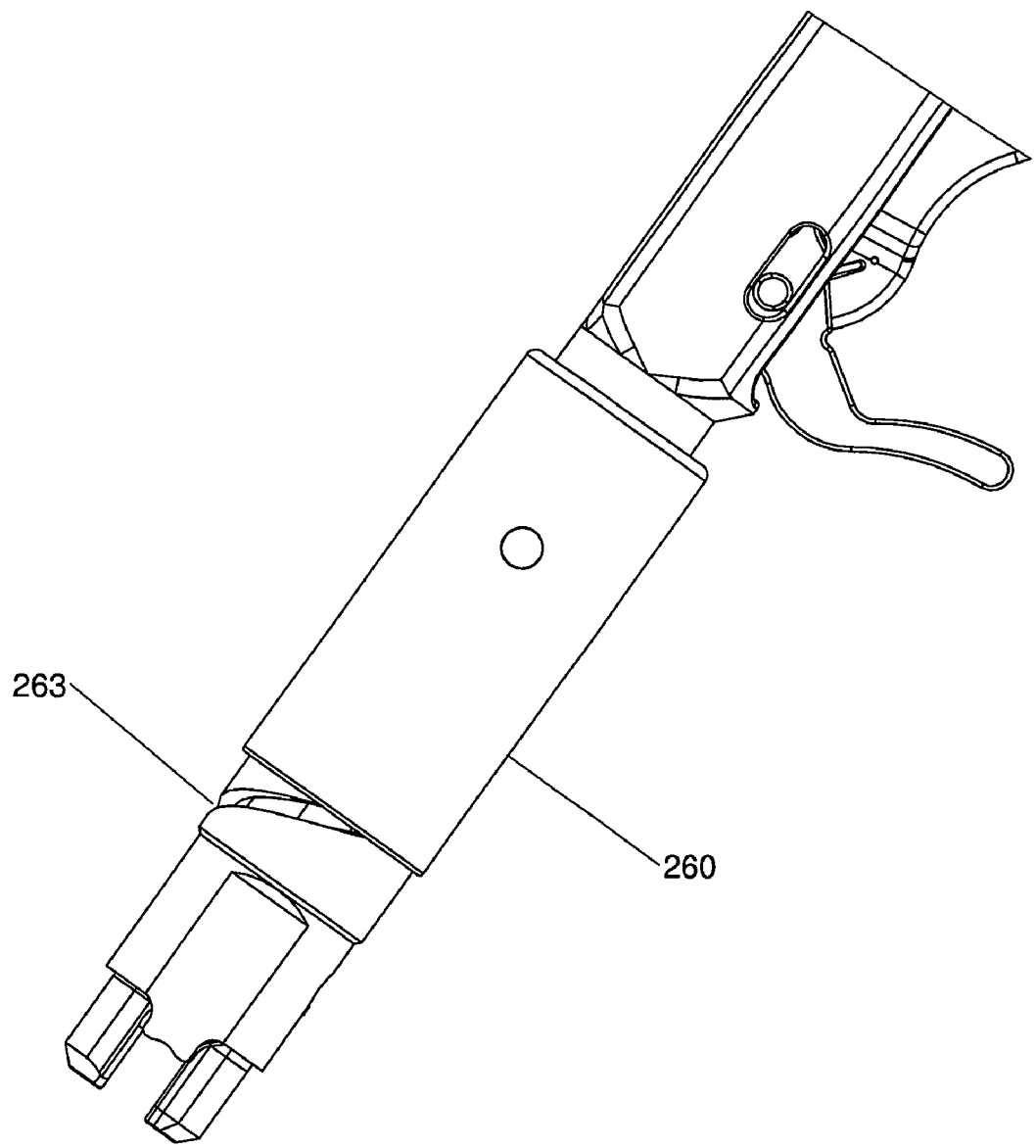
Figure 20:
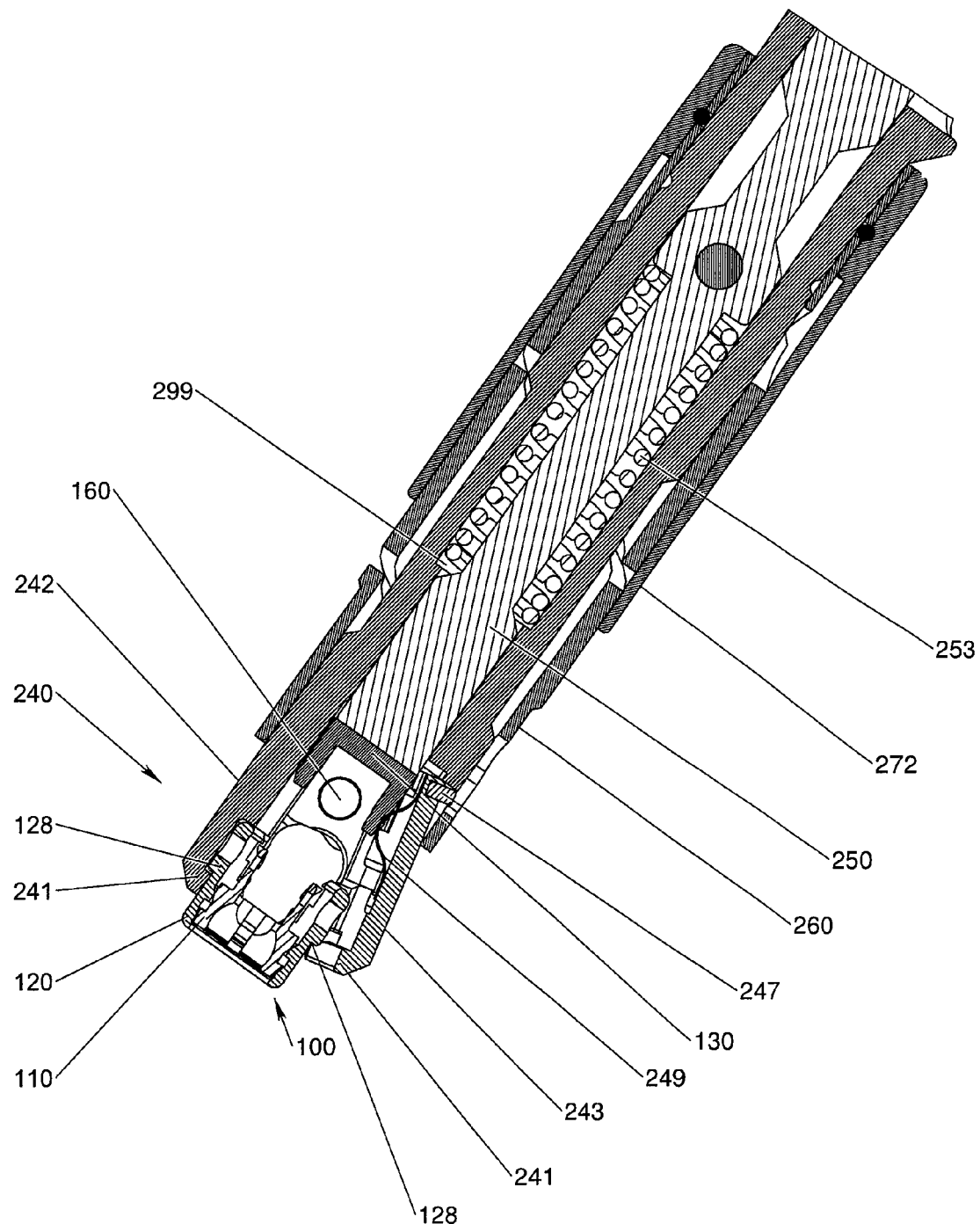
FIGS. 20a-d depict the distal end of the instrument shown in FIG. 16, and illustrates the securing of a coupling assembly within the instrument and sequentially advancing and locking a cap member to the coupling assembly to secure a spinal rod therein.
Figure 20:
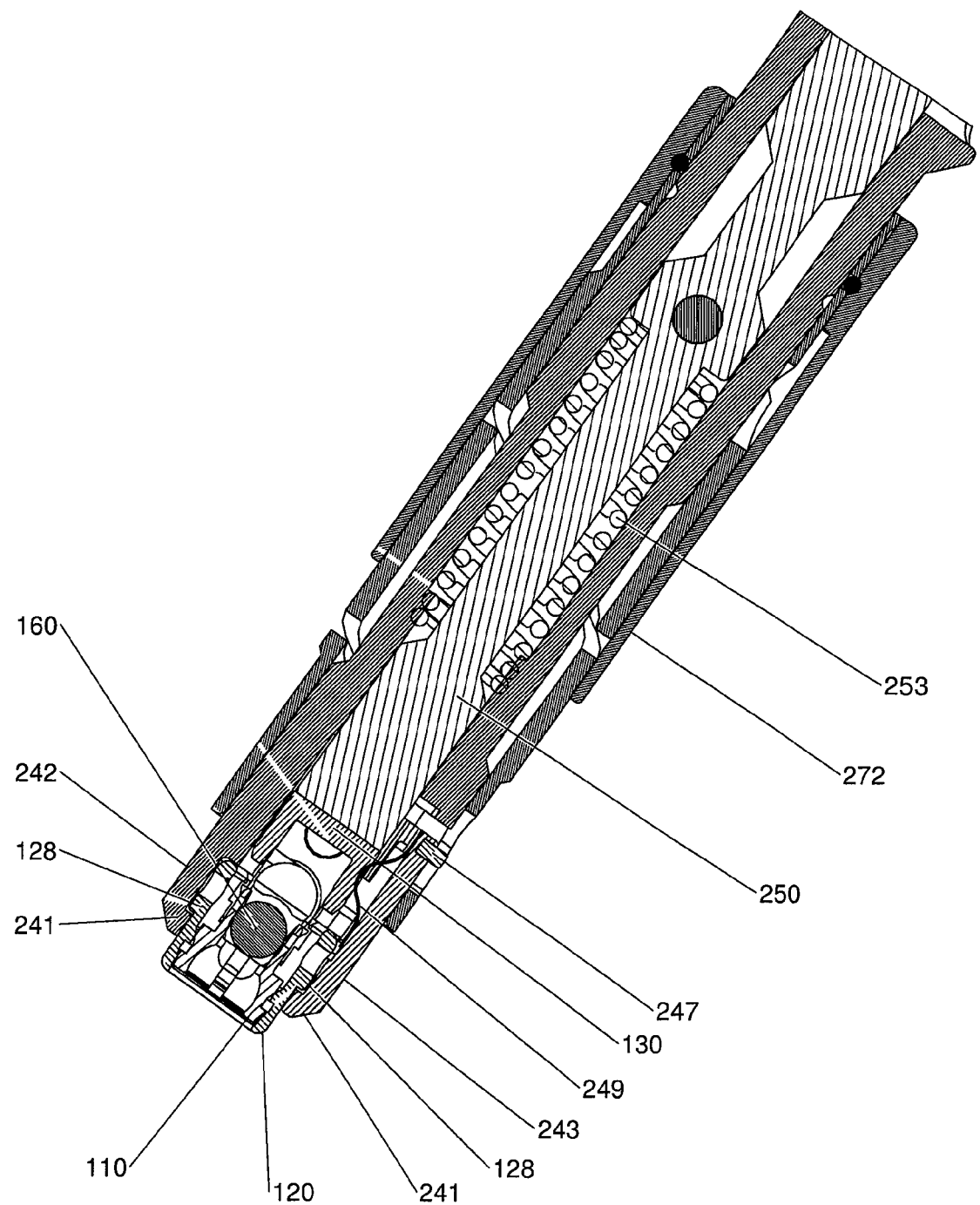
Figure 20:
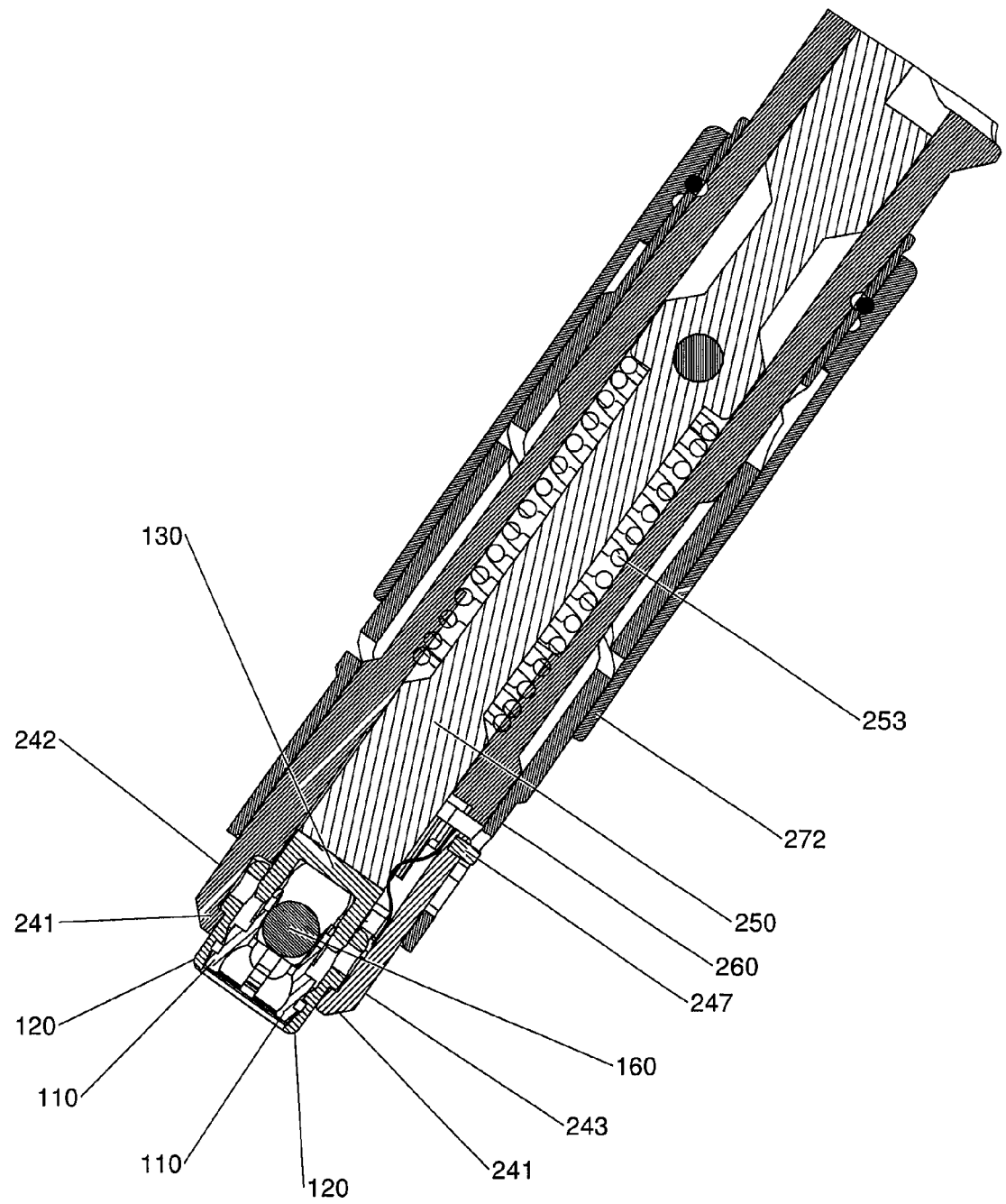
Figure 20:
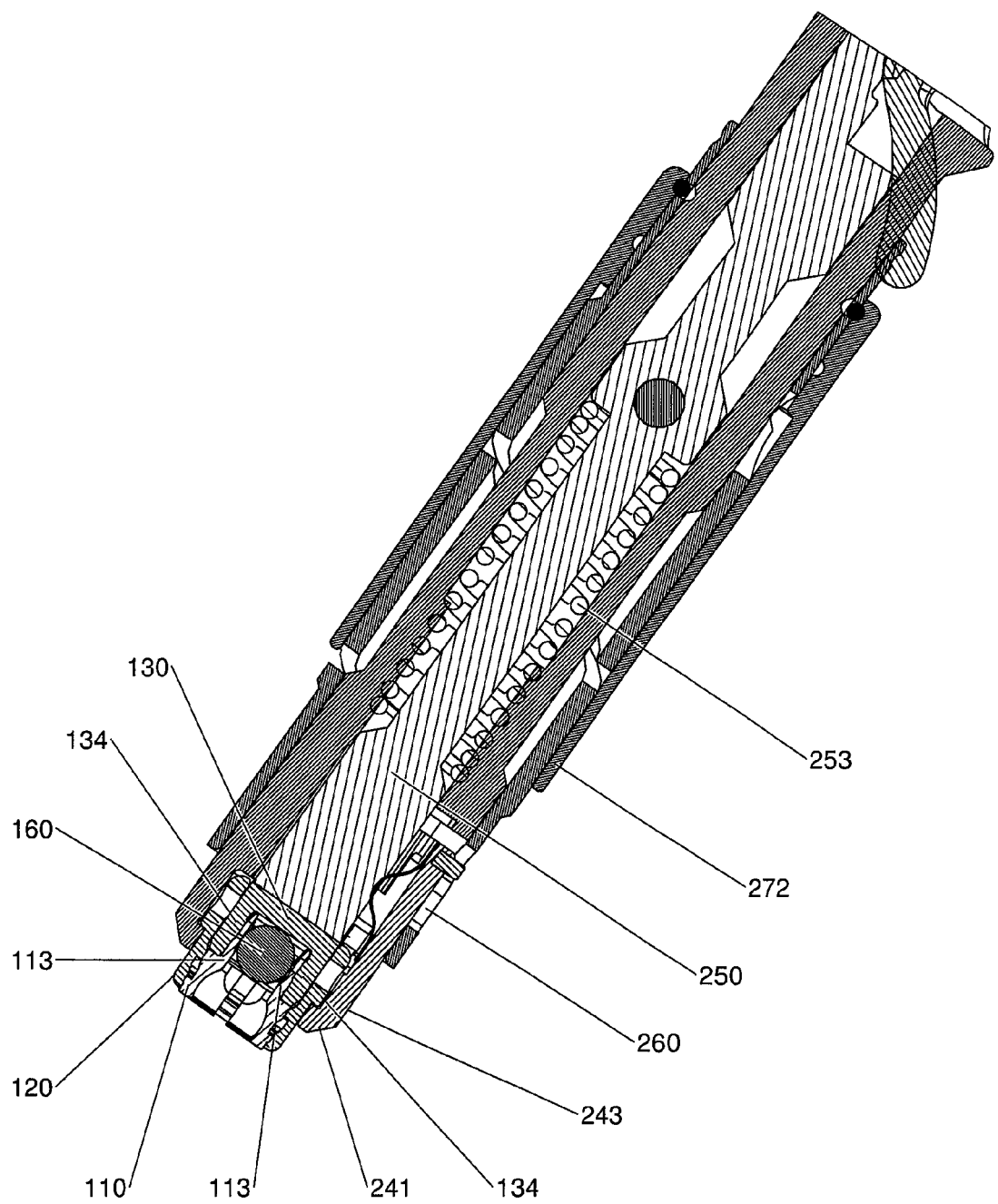
Figure 21:
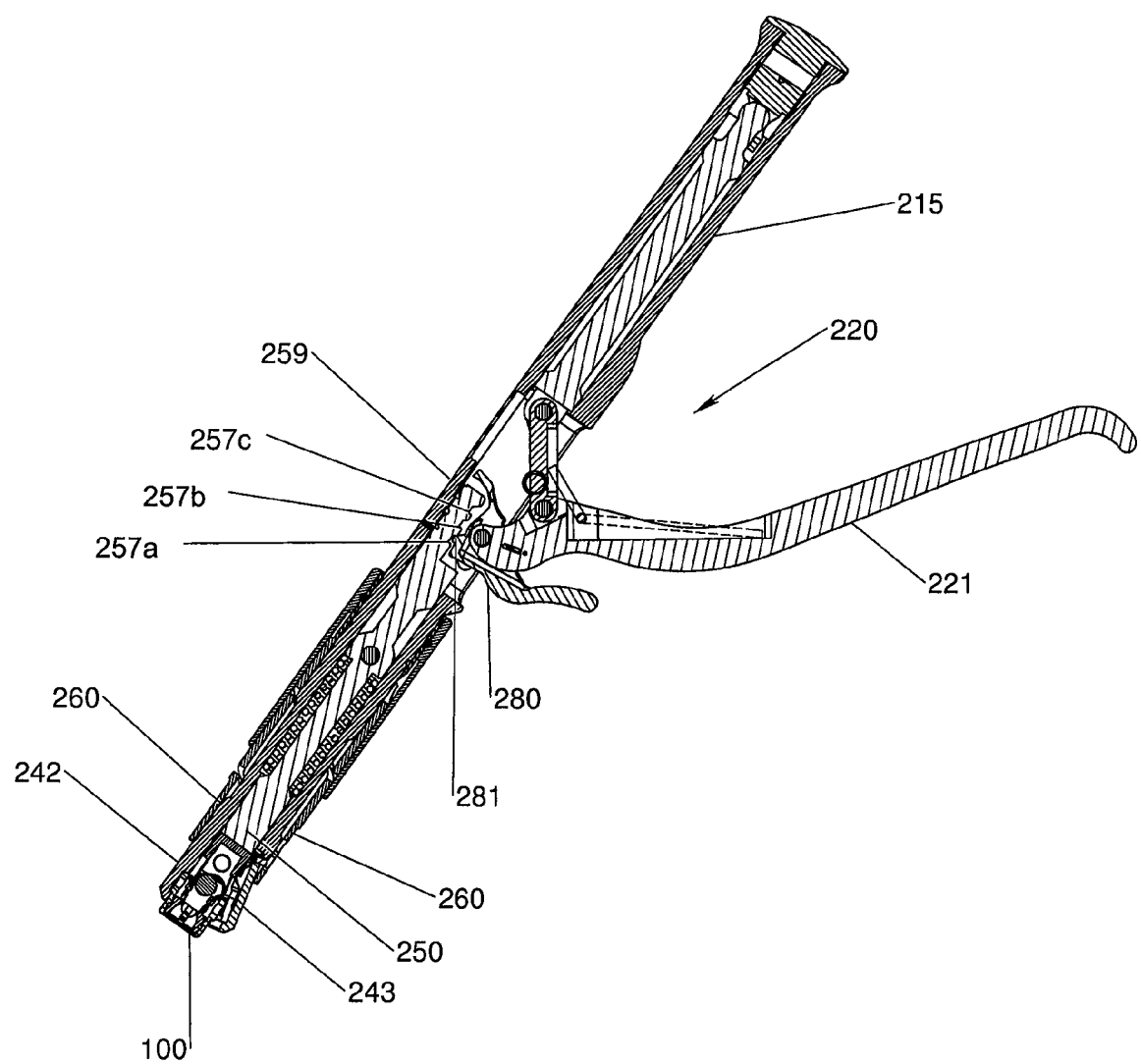
FIGS. 21a-g illustrate sequential activation of the instrument of FIG. 16 in order to ratchet a cap member into place within a coupling assembly.
Figure 21:
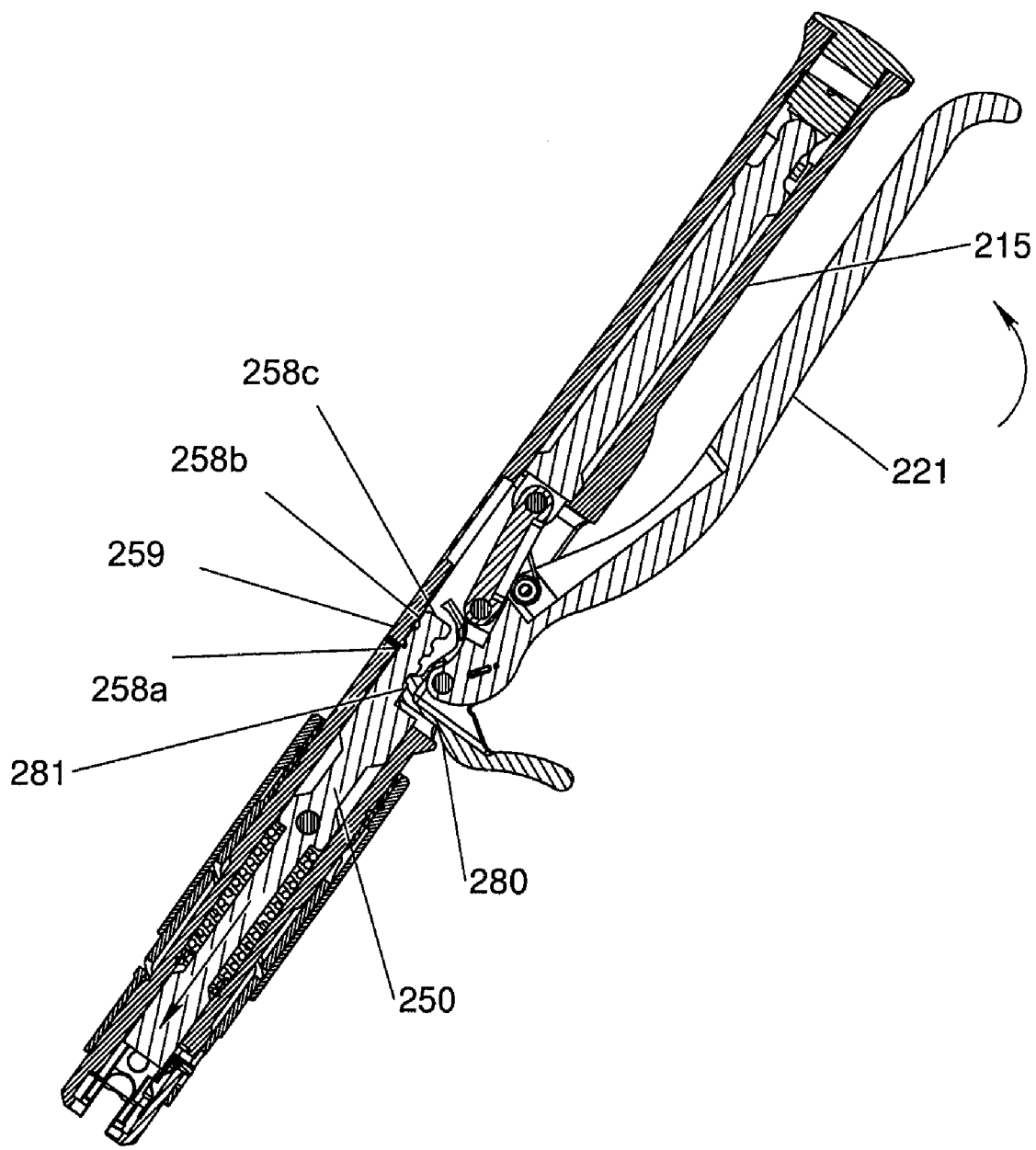
Figure 21:
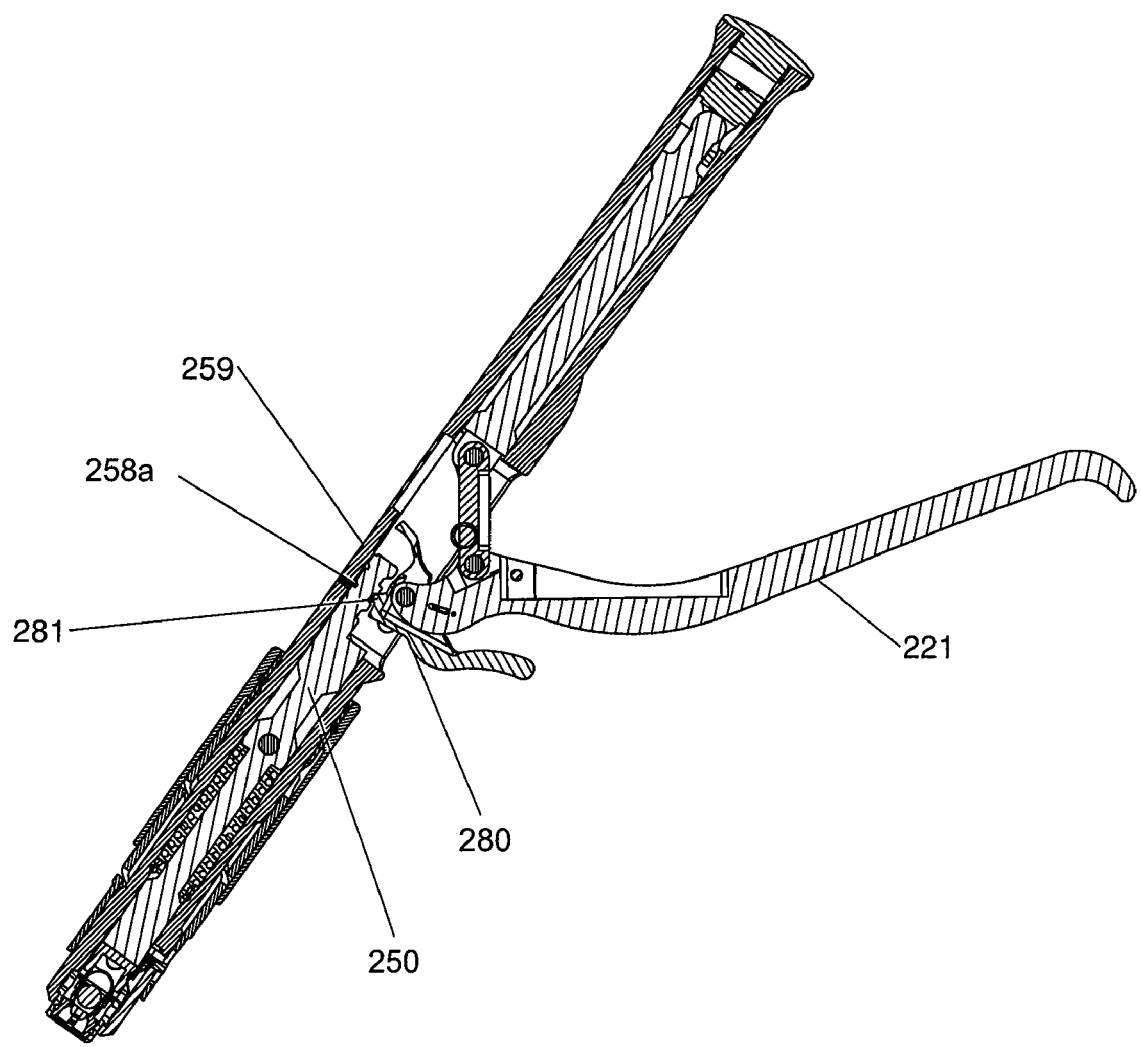
Figure 21:
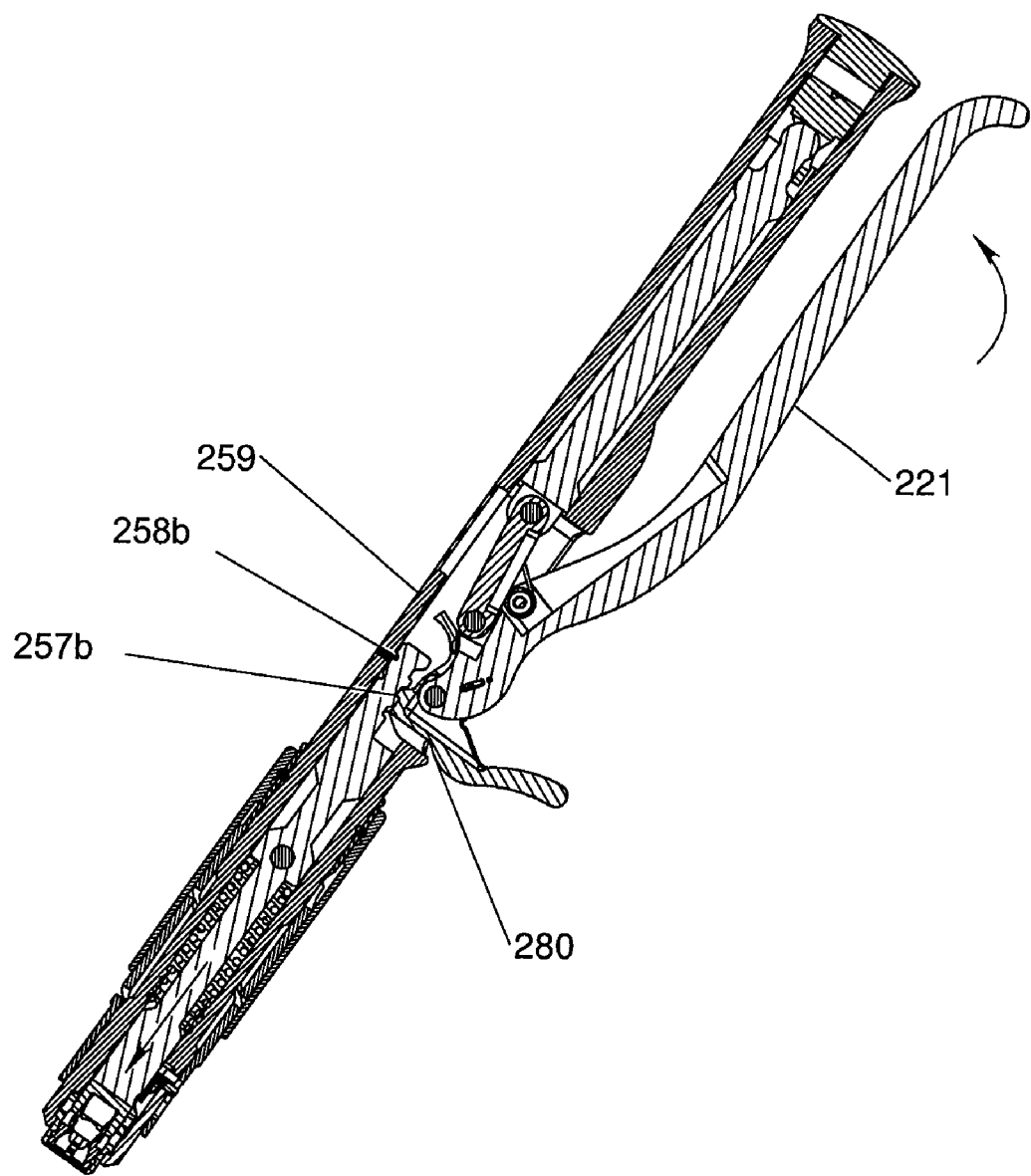
Figure 21:
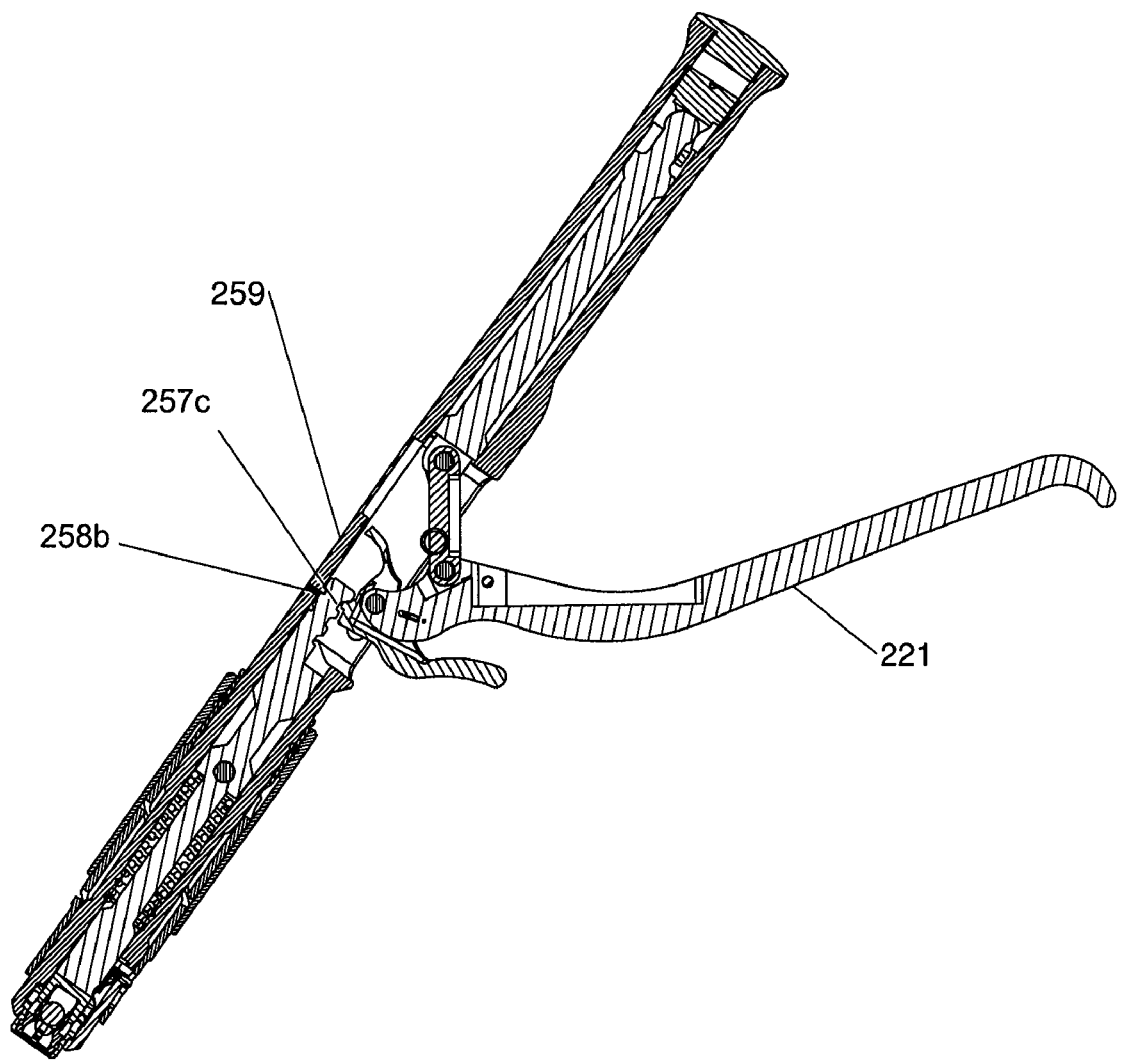
Figure 21:
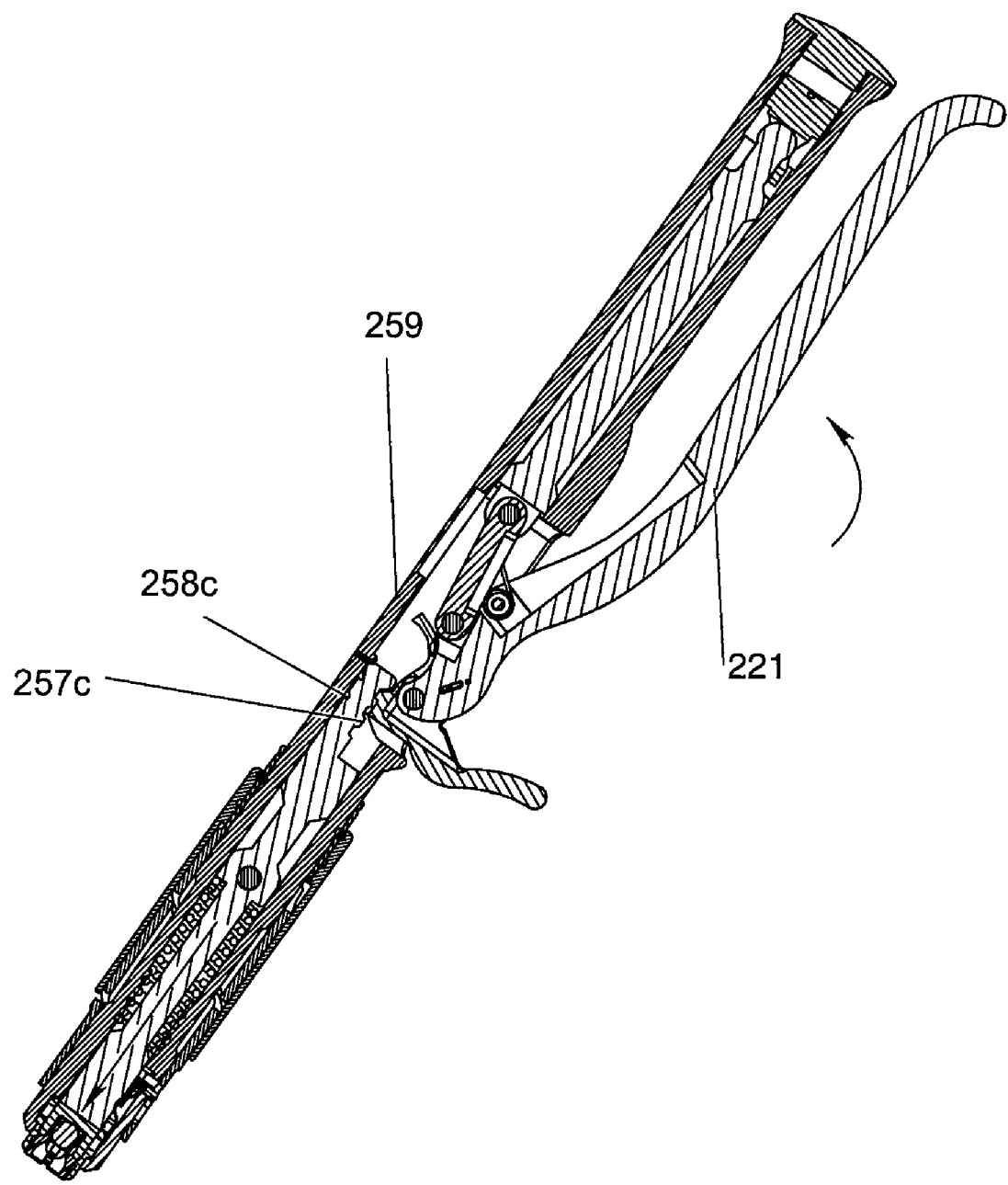
Figure 21:
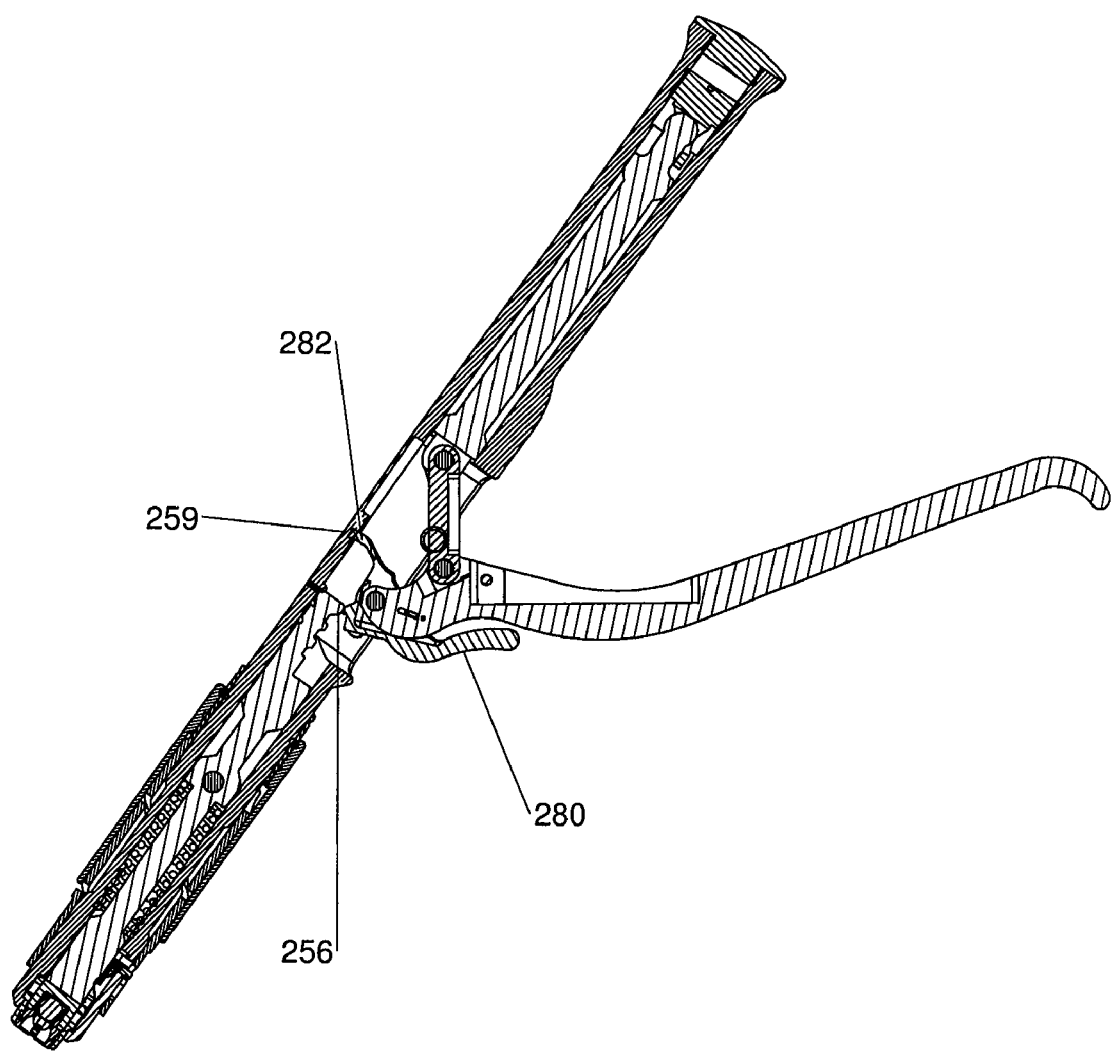

As further shown in FIGS. 16-18, an actuator assembly 220 is provided for shifting the drive member 250 toward and away from the clamp device 240. The actuator assembly 220 connects to the instrument body 210 and the drive member 250 to cause shifting of the drive member with respect to the instrument body. The illustrated form of actuator assembly 20 includes an actuator lever 221 extending from an actuator opening 211 in the instrument body 210. A pivot link 225 connects the lever 221 to the instrument body 210 through a first pivot pin 226 located at a fixed position within the instrument body 210 and a second pivot pin 227 coupled to the lever 221. The fixed length of the pivot link 225 holds the second pivot pin 227 disposed in the lever 221 at a fixed distance from the first pivot pin 226 in the body as the lever shifts toward the instrument handle 215.

A biasing member in the form of a wire spring 219 coupled to the lever 221 and instrument body 210 may be provided to bias the lever 221 away from the instrument body 210. This automatically allows the lever to return to its starting or "ready" position upon releasing the actuator lever.

The actuator lever 221 is also linked to a ratchet member 280 via a ratchet pin 223. The ratchet member 280 includes a ratchet tooth 281 that engages corresponding teeth 257 on the drive member 250. The ratchet member 280 also includes a disengagement member 282 disposed near the proximal end of the drive member 250. As the actuator lever 221 is shifted toward the instrument handle 215, the rigid pivot link 225 directs movement of the lever 221 and the ratchet member 280 coupled thereto toward the distal end of the instrument. The ratchet tooth 281 engages the drive member 250 when ratchet tooth 281 engages drive teeth 257a-c on a first side of the drive member 250, transmitting force to the drive member upon pivoting of the actuator and ratchet member, thereby shifting the drive member 250 axially through the instrument. When the actuator lever 221 is released, a pawl 259 engages notches 258a-c on a second side of the drive member (see FIGS. 21b-d) to prevent retrograde motion of the drive member. The pawl 259 is shown as a slightly flexible tab formed integrally with the instrument body and having a sloped foot portion to allow sliding of a notched surface of the drive member in a distal direction but preventing sliding in a proximal direction. The pawl could alternatively be any pivoting member or contoured surface designed to permit one-way movement of the drive member. Pulling on the actuator lever 221 once advances the drive member a first amount, driving the head 252 of the drive member toward the clamp device 240. Releasing and then pulling again on the actuator lever 221 shifts the drive member and reducing member to successive predetermined positions due to operation of the ratchet device. Operation of the actuator assembly and ratchet device is explained in greater detail in connection with FIGS. 21-23.

As also shown in FIGS. 16-18, the instrument includes a reducing sleeve 260 for exerting a downward force on the rod. The reducing sleeve 260 is releasably coupled to the drive member 250 via a coupling sleeve 272, a coupling pin 271 and a plurality of shifting elements 273 in a manner similar to that described above in connection with FIGS. 12a-d of the previous instrument. As the actuator 221 is first shifted, the drive shaft 250, reducing sleeve 260, and coupling sleeve 272 all shift axially toward the distal end of the instrument. Shifting elements 273 are provided to couple the coupling sleeve 272 to the reducing sleeve 260, with the coupling sleeve coupled to the drive member 250 via a coupling pin 271. As the reducing sleeve 260 shifts over the grasping device 240, the sleeve forces pivotable jaw 243 to pivot toward the fixed grasping member 242. At a predetermined position, the shifting elements 273 shift into an annular recess 276 of the instrument body, thereby coupling the reducing sleeve 260 to the instrument body 210 and releasing the coupling sleeve 272 (and the drive shaft 250 to which it is connected) from the reducing member. Thus, even though movement of the reducing sleeve 260 toward the distal end of the instrument ceases, the drive shaft 250 may continue to advance. An elongate opening 278 is provided in the reducing sleeve in order to allow the coupling pin 271 that couples the drive member 250 to the outer coupling sleeve 272 to shift therethrough once the coupling sleeve 272 and drive shaft 250 have been released from the reducing sleeve 260.

A limiting element, such as inhibitor switch 30 of FIGS. 9a-9c is not necessary when a ratchet device is provided, since the ratchet device will advance the drive member 250 by a predetermined amount with each pull of the actuator lever 221.

As shown in FIG. 18, the reducing sleeve may contain a helical compression slit 263 to allow the sleeve to compress slightly. Other configurations of slits may be used to achieve the same purpose. The compression slit 263 permits the instrument to be used with both fixed (integral) and polyaxial anchor members, allowing the reducing sleeve to be advanced into engagement with the spinal rod 160 regardless of whether or not there is an insert member 110 that must be further inserted into the outer member or yoke 120. In other words, if an anchor member is formed integral with a coupling member, or if the anchor member is already fully locked within an insert member 110 that is fully advanced within an outer member 120, as shown in FIG. 13, there is little compression of the reducing member 260. On the other hand, if the insert member 110 is only partially inserted in the outer member 120, as in FIG. 14a, the slit 263 in the reducing member 260 allows the reducing member to compress in an amount greater than the difference in the distance between the partially and fully inserted positions of insert member 110. As the slit reducing member 260 compresses, it functions as a resilient spring. The slit is preferably configured so that the axial force generated by the reducing member 260 as it functions as a resilient spring is great enough to overcome any friction between the spinal rod 160 and arms of the insert member 110 in order to fully seat the rod in the insert member. Furthermore, the axial spring force of the reducing member 160 should be great enough to overcome any forces exerted by the patient's anatomy that may bias the spinal rod 160 away from the seat of the insert member 160 (such as lateral or torsional forces exerted by misalignment of the vertebrae).

As with other embodiments, in order to secure the rod 160 in a coupling device 100, the rod is arranged in or above the rod-receiving channel 119 of the device. The instrument 201 is then clamped to the coupling device 100 with the rod 160 received therein so that the axis of the drive member 250 is aligned with the assembly 100 and rod 160. The drive member 250 and the clamp device 240 cooperate to secure the coupling device 100, advance the cap member 130 into the assembly, and lock the rod 160 in place within the assembly. By pulling the actuator lever 221, the drive member 250 is advanced and drives the cap member 130 linearly into the coupling device 100, locking the spinal rod 160 therein. The ratchet and corresponding teeth on the drive member 250 may be configured so that each pull of the actuator lever 221 advances the cap to a predetermined provisional lock or full lock position. Markings may be provided on the exterior of the instrument body in order to identify the position of the reducing member and/or drive member.

Operation of the grasping device or clamp 240 is depicted in FIGS. 19a-d. The pivotable jaw member 243 of the grasping device 240 is pivoted between an open position, as shown in FIGS. 19a-b, and a closed position, as shown in FIGS. 19c-d, by a pin 247 coupled to the reducing member 260. As illustrated, the pin 247 is fixed to the pivotable jaw 243 at one end, while the other end rides in a slightly elongate slot formed in the reducing member 260. Upon pulling the actuator toward the instrument handle, the drive member 250 is advanced in a direction A. The reducing member is initially coupled to the drive member 250, and therefore also advances in direction A. As the reducing member 260 advances, it shifts the position of pin 247, forcing the jaw member to pivot toward the fixed grasping member 242. The jaw member 243 is shown in a closed or clamped position in FIGS. 19c-d. In this closed position, the jaw 243 and fixed grasping member are configured to secure a coupling device therebetween.

The pivotable jaw also has a flat spring 249 coupled thereto in order to secure a cap member 130 in place within the grasping device. The cap member 130 is trapped between the spring and fixed grasping member 242. The spring is able to flex to allow the jaw member 243 to pivot to a closed position while maintaining positioning of the cap member. The spring 249 allows the cap to be held in place until it is abutted by the drive member 250, and allows the cap 130 to be held by the instrument when inserted between grasping members rather than secured to the drive member itself. Insertion of the cap member 130 into the coupling device 100 is illustrated in FIGS. 20a-d. The coupling device 100, shown including insert member 110 and outer member 120, is received within the grasping device 240 while the jaw member 243 of the grasping device is in the open position. The instrument is maneuvered so that a shoulder portion 128 of the coupling assembly outer member 120 is adjacent to a flange 240 of the fixed member 242, as shown in FIG. 20a.

Shifting of the actuator advances the drive member 250 and reducing member 260 so that the reducing member 260 forces the jaw member 243 to pivot inward as shown in FIG. 20b. As the jaw 243 pivots, the inwardly-directed flange 240 on the jaw shifts to a position below a second shoulder 128 of the coupling assembly outer member 120, securing the coupling member to the tool. At the same time, the drive member 250 advances the cap member 130 slightly toward the cap member.

Further shifting of the actuator advances the drive member 250 further, as shown in FIG. 20c, so that the cap 130 is driven into engagement with the coupling device 100 by the drive member. Simultaneously, the reducing member 20 continues to advance, engaging and reducing the spinal rod 160 into the coupling device 100.

Still further shifting of the actuator causes the drive member 250 to advance the cap member 130 fully into the coupling device 100, locking the spinal rod 160 within the coupling assembly as shown in FIG. 20d. At this point, the drive member has disengaged from the reducing member 260, so that the reducing member has not advanced compared to its position in FIG. 20c. This helps to avoid undesired bending of the rod and damage to the instrument.

Any number of predetermined positions for the various instrument components may be provided. The illustrated ratchet mechanism is included so that multiple pulls of the actuator lever 221 cause the instrument to perform different, sequential functions. However, there are alternative configurations for allowing the actuator to shift the instrument components into a plurality of predetermined positions. For instance, the instrument may be configured so that the above predetermined positions are reached by shifting the actuator a predetermined number of times, by selectively limiting motion of the actuator by a known amount at each stage, or by providing visual or audible cues from which the cap location or other positional relationships may be determined.

FIGS. 21a-g demonstrate how one illustrated actuator assembly 220 causes the drive member 250 and reducing member 260 to advance to the predetermined positions of FIGS. 20a-d. In FIG. 21a, the instrument is in a ready position, and has been positioned so that a coupling device 100 is received therein. The jaw 243 of the grasping device is at an open position. By shifting the actuator lever 221 toward the handle 215, as in FIG. 21b, the ratchet member 280 causes linear advancement of the drive member 250 as the ratchet tooth 281 engages teeth 257 on the drive member 250. By sequentially engaging and disengaging teeth on the drive member, the ratchet member advances the drive member to a plurality of predetermined positions. Pulling on the actuator lever 221 once advances the drive member a first amount (shown in FIG. 21b), driving the head 252 of the drive member toward the clamp device 240. When the actuator lever 221 is released (FIG. 21c), the sloped surface on the back end of the ratchet tooth 281 allows the ratchet tooth to slide to the next tooth position along the drive member 250 without forcing the drive member to shift back toward the proximal end of the instrument. Shifting the lever 221a second time will advance the drive member 250 a second amount to a second predetermined position (FIG. 21d), and thereafter releasing the lever 221 will allow the ratchet 281 to move to the next position on the drive member 250 (FIG. 21e). Shifting the lever a third time will advance the drive member a third amount to a third predetermined position, preferably fully inserting the locking cap into the coupling assembly (FIG. 21f).

In the form illustrated in FIGS. 21a-g, the end of the drive member is provided with a flange 256 that extending outward from the drive shaft and configured so that upon release of the actuator after the third pull, the ratchet member 280 is automatically pivoted slightly, forcing the disengagement portion 282 of the ratchet member to abut the pawl 259 to disengage the pawl from the notched surface 258 of the drive member. In this manner, actuating the device through a full cycle automatically releases the pawl 259 from the drive member, allowing a spring 253 or other similar mechanism to return the drive member to its initial position. Alternatively, pivoting the ratchet release switch 283 toward the actuator handle 221 at any time pivots the ratchet member slightly to disengage ratchet tooth 281 from the drive member 250 and simultaneously abut the flexible pawl 259 with the ratchet disengagement arm 282, temporarily flexing the pawl slightly away from the drive member and allowing the drive member to return to its initial (proximal) position due to bias provided by the drive return spring 253. As the drive member 250 returns to its original position, its proximal end abuts the disengagement member 282, pivoting the ratchet member 250 back to its initial position and allowing the pawl 259 to re-engage the drive member.

Figure 22:
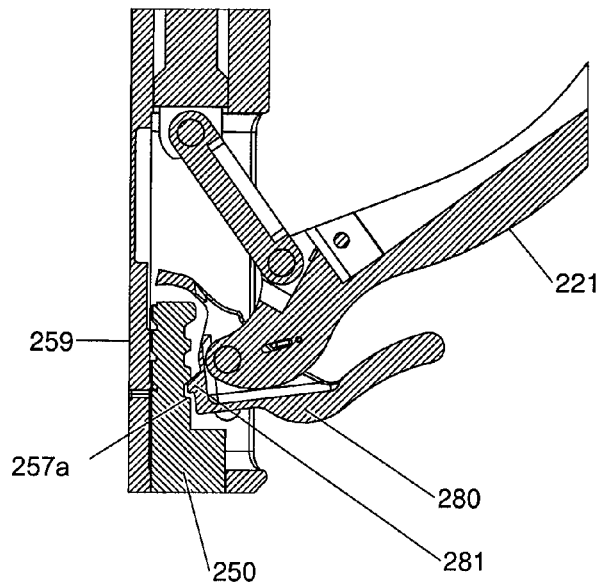
FIGS. 22a-h are sequential cross sections of the ratchet mechanism of the instrument of FIG. 16, illustrating the operation of the ratchet mechanism to shift the drive member of the instrument.
Figure 22:
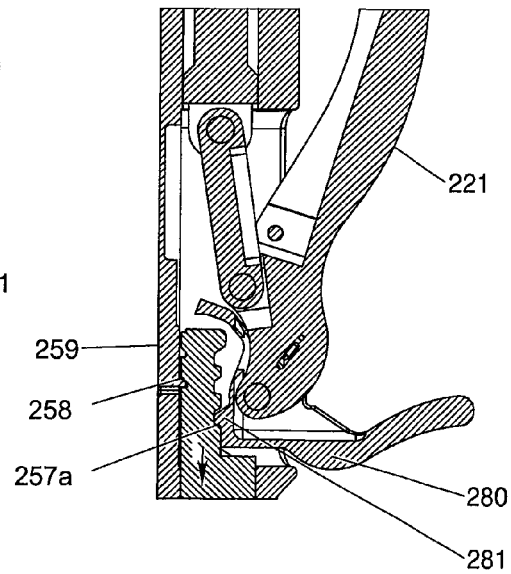
Figure 22:
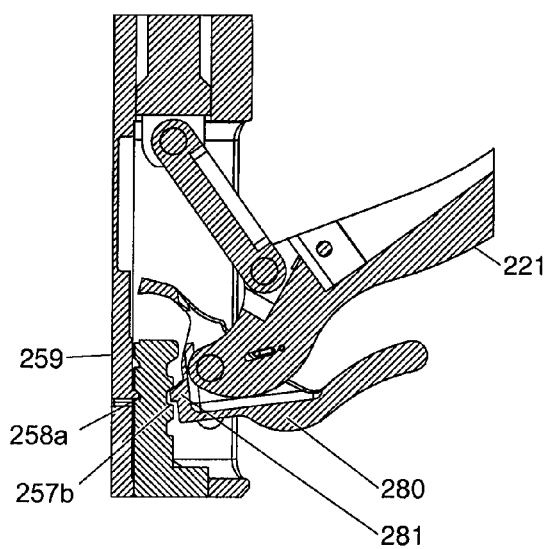
Figure 22:
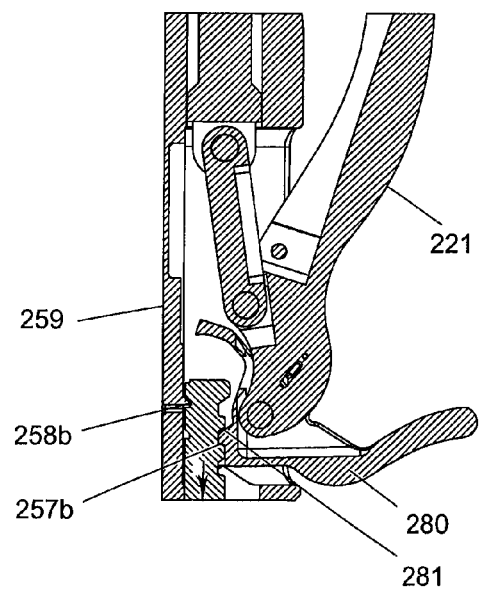
Figure 22:
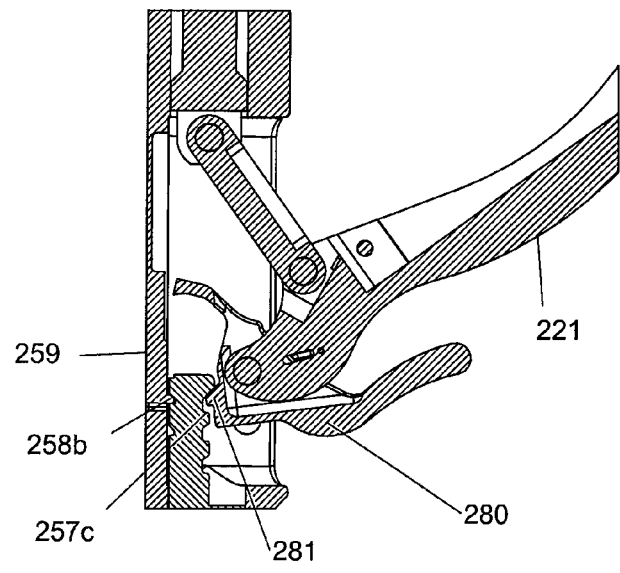
Figure 22:
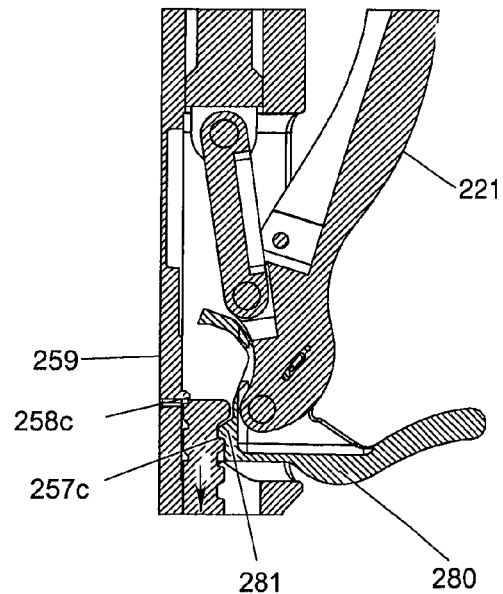
Figure 22:
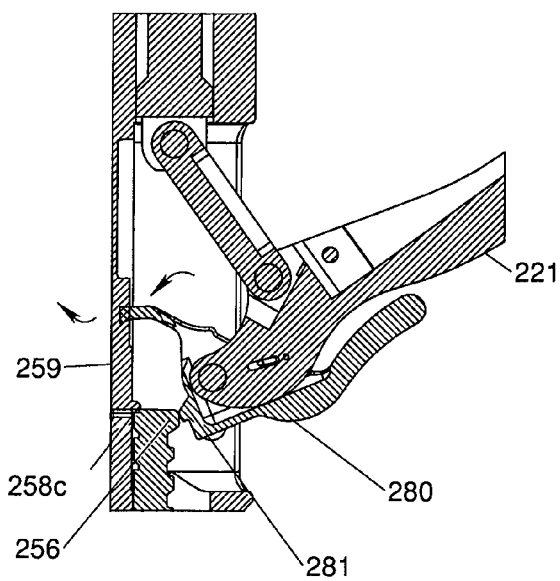
Figure 22:
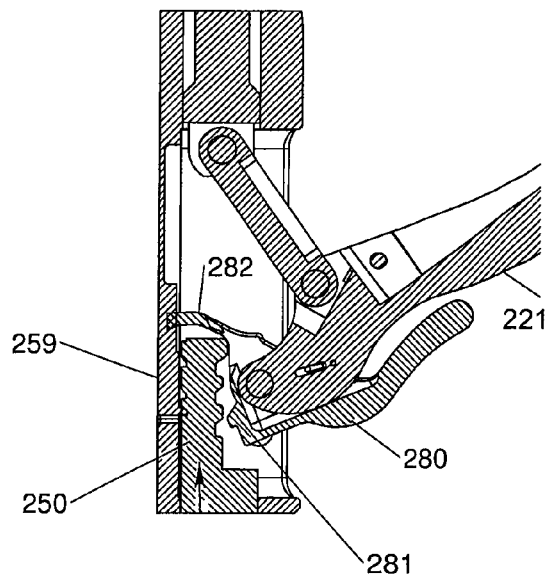
Figure 23:
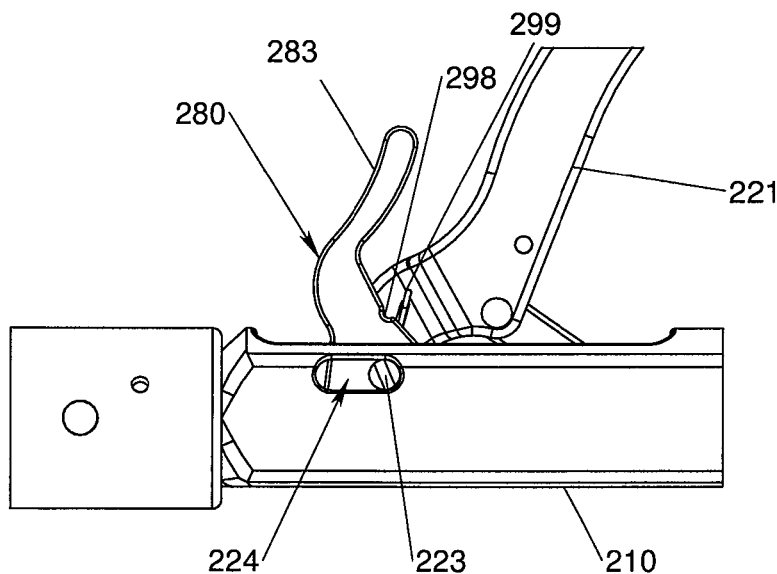
FIGS. 23a-c sequentially illustrate the operation of a spring member to position the ratchet member of the instrument of FIG. 16.
Figure 23:
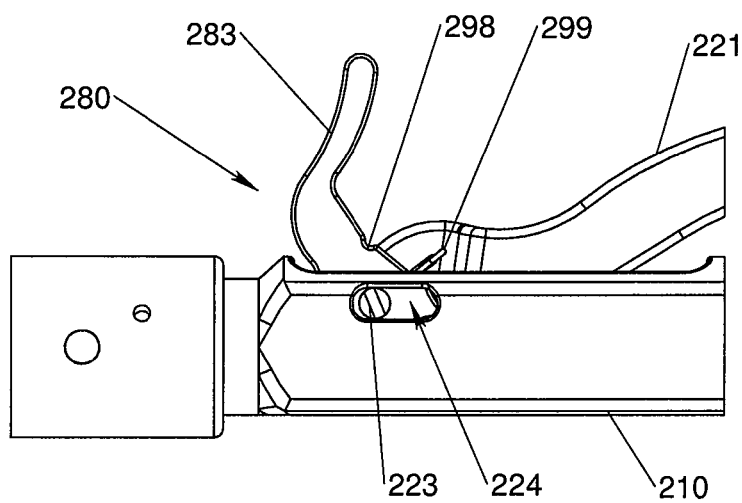
Figure 23:
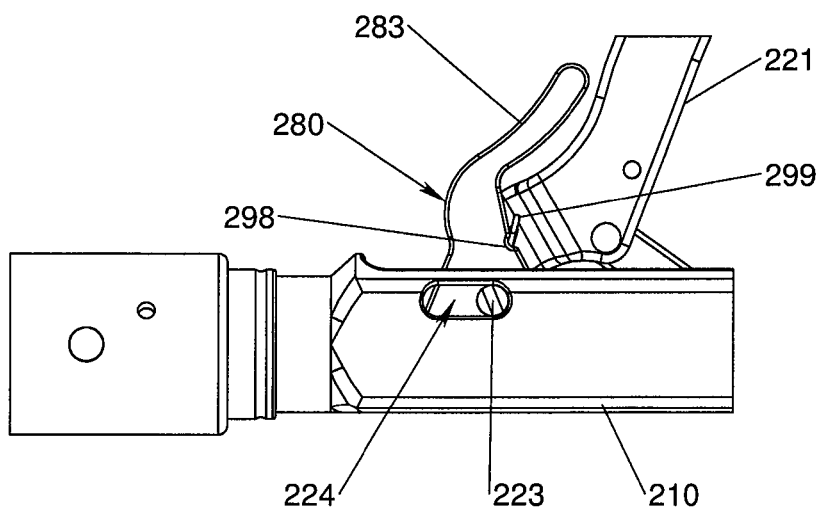
Figure 24:
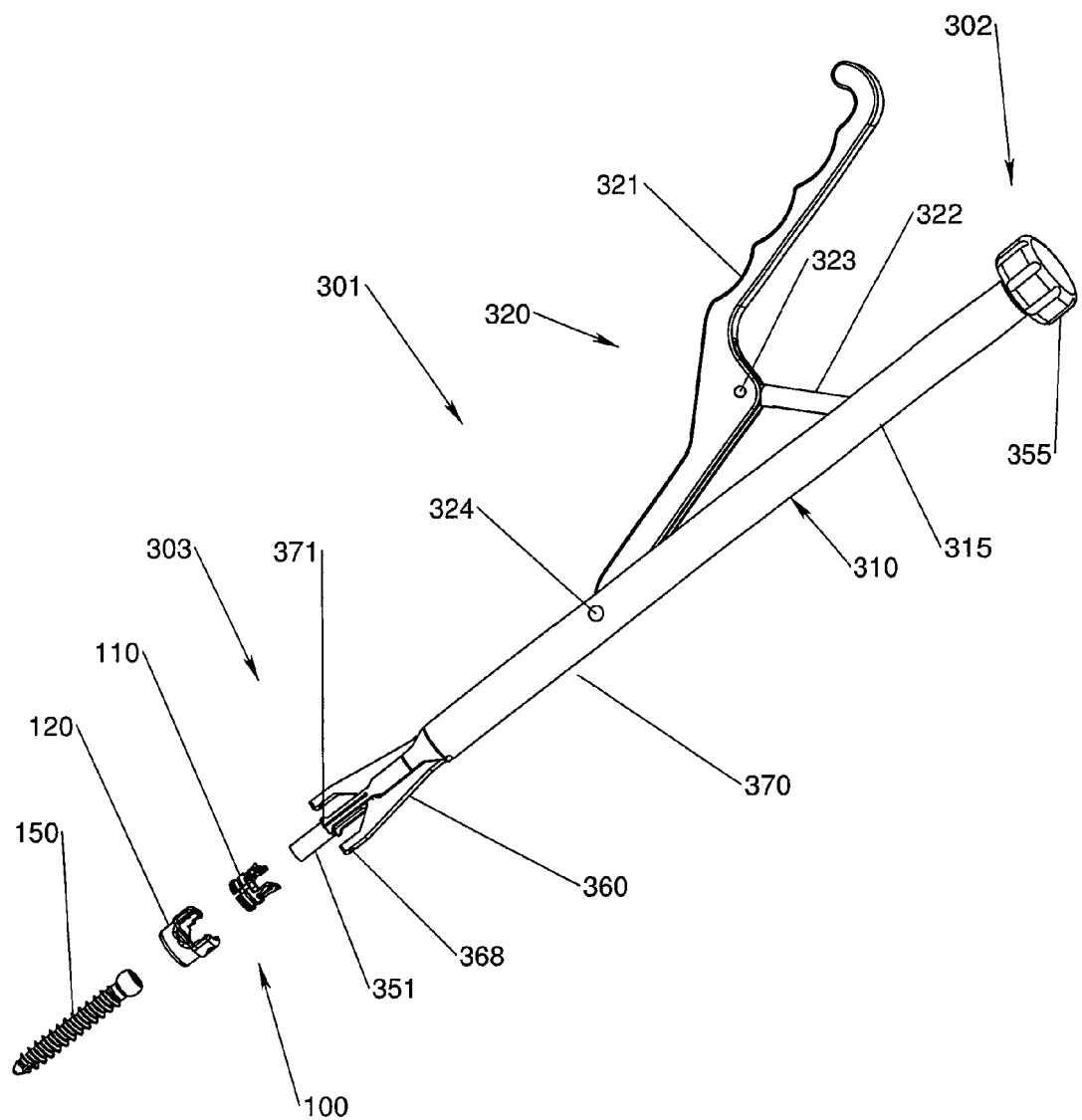
FIG. 24 is a front view of an instrument configured to secure the position of an anchor member within a coupling assembly.

Examining the components of the ratchet device in greater detail, it can be seen that the geometries of the ratchet components are configured to interact with one another and with the geometries of the actuator and drive member in order to automatically reset the actuator and/or ratchet device at predetermined points in order to facilitate use of the instrument. As seen in FIG. 22, the ratchet tooth 281 has an upper ramped surface and a lower flat surface, while the teeth 257a-c have lower ramped surfaces and upper flat surfaces. This allows one-way sliding of the ratchet tooth 281 along the drive member teeth 257a-c. When the actuator lever 221 is pivoted, the ratchet member 280 coupled to the lever is shifted downward. Similarly, the resiliently flexible pawl 259 has a foot with a sloped upward surface that engages notches 258a-c on another surface of the drive member to permit axial advancement of the drive member while inhibiting backward shifting of the drive member. Due to engagement between the ratchet tooth 281 and one of drive teeth 257a-c, this also causes shifting of the drive member 250 axially downward. In an initial position, the ratchet tooth 281 is positioned above a first drive tooth 257a (FIG. 22a). A first pull on the actuator lever 221 shifts the drive member 250 downward along the axis of the instrument by a predetermined amount (FIG. 22b). Releasing the actuator lever 221 allows the ratchet tooth 281 to slide above the next drive tooth 257b (as shown in FIG. 22c). The drive member 250 is prevented from shifting backward by engagement between flat surfaces of the pawl 259 and a first notch 258a. A second pull on the actuator lever 221 advances the drive member to a second predetermined position (FIG. 22d), and thereafter releasing the lever repositions the ratchet tooth 281 above the next drive tooth 257c while the pawl 259 prevents backward shifting of the drive member (FIG. 22e). A third pull on the actuator lever 221 advances the drive member to a third predetermined position (FIG. 22f). At this point, when the lever 221 is released, the drive tooth 281 abuts the flange 256 that is more prominent than the drive teeth 257a-c (FIG. 22g). The flange 256 forces the ratchet member 280 to pivot significantly, shifting release member 282 into abutment with the pawl 259, shifting the pawl away from the drive member. With the pawl 259 disengaged, the drive member 250 shifts backward along the instrument axis (FIG. 22h), eventually abutting and pivoting the ratchet release arm 282 and resetting the ratchet device. Of course, more or less predetermined positions of the drive member may be provided by varying the number of teeth and/or other surface features of the drive member.

As best seen in FIGS. 23a-c, a spring 299 may also be mounted in the actuator lever 221 to exert some force on the ratchet member 280 to facilitate engagement between the ratchet member and drive member as the lever pivots back to an open position. The spring 299 helps to orient to ratchet member 280 as the lever 221 pivots. The ratchet member 280 may also include a recess 298 for receiving the spring at a predetermined position. For instance, as the actuator lever 221 is pivoted from an open position (FIG. 23a) to a closed position (FIG. 23b), the spring 299 abuts the surface of the ratchet member 280. As the ratchet sequentially engages teeth on the drive member (see FIG. 22), the point at which the spring 299 abuts the drive member 280 becomes closer to the spring receiving recess 298. When the ratchet reaches a point where it abuts the drive member release flange 256 (as in FIG. 22g), the spring member 299 becomes lodged in the recess 298, as shown in FIG. 23c. Since the spring must be compressed to escape the recess 298, the ratchet member 280 will be held in the orientation shown in FIG. 23c until rearward shifting of the drive member as it returns to its initial position provides sufficient force to pivot the ratchet member 280 (as shown in FIG. 22h), returning the ratchet member to its initial position. In this manner, after the ratchet member arrives at the release flange, the spring 299 prevents the ratchet member from re-engaging the drive member until the drive member returns to its initial position.

The principles and structures described above may be used in order to provide other instruments having similar functions. For instance, in another form, an instrument may be provided to secure an anchor member to a coupling assembly prior to securing the rod therein.

For instance, an instrument 301 is illustrated in FIGS. 24-32 for engaging a pedicle screw or other anchor member 150 and locking an axially-assembled rod coupling device 100 of the type previously described herein to the screw 150. The anchor member 150 and coupling device 100 may be locked together using the instrument 301 before or after the anchor 150 is secured to a patient's spine. The illustrated anchor locking instrument 301 includes an instrument body 310 with a handle 315 at the proximal end 302 to be grasped by a surgeon.

The distal end 303 of the instrument 301 includes a grasping device 368 for grasping the outer member 120 of a coupling assembly and securing it to the instrument, an insert driver 371 for driving the insert member 110 of the coupling assembly into the outer member 120, and an anchor securement head 351 for securing an anchor member 150 and pulling it into the coupling device 100.

In use, the anchor securement head 351 secures an anchor member 150 and draws the anchor member proximally toward a coupling device 100 held by the grasping member 368. The coupling assembly outer member 120 is secured by the grasping member 368, with the insert member 110 partially inserted into the outer member 120. As previously described herein, a lower portion of the insert member 110 is configured to receive the head of the anchor member, and full insertion of the insert member 110 into the outer member 120 compresses the insert member lower portion to lock the anchor member head in position with frictional forces. The instrument 301 serves to draw the anchor member into the insert member 110 to snap lock the anchor member in the insert member, with the grasping member thereafter pulling the coupling assembly outer member 120 in the proximal direction to compress the insert 110, friction locking the anchor member 150 in place. Both of these functions are performed by pivoting a single actuator handle 321 toward the instrument handle 315, as will be described further below.

Figure 25:
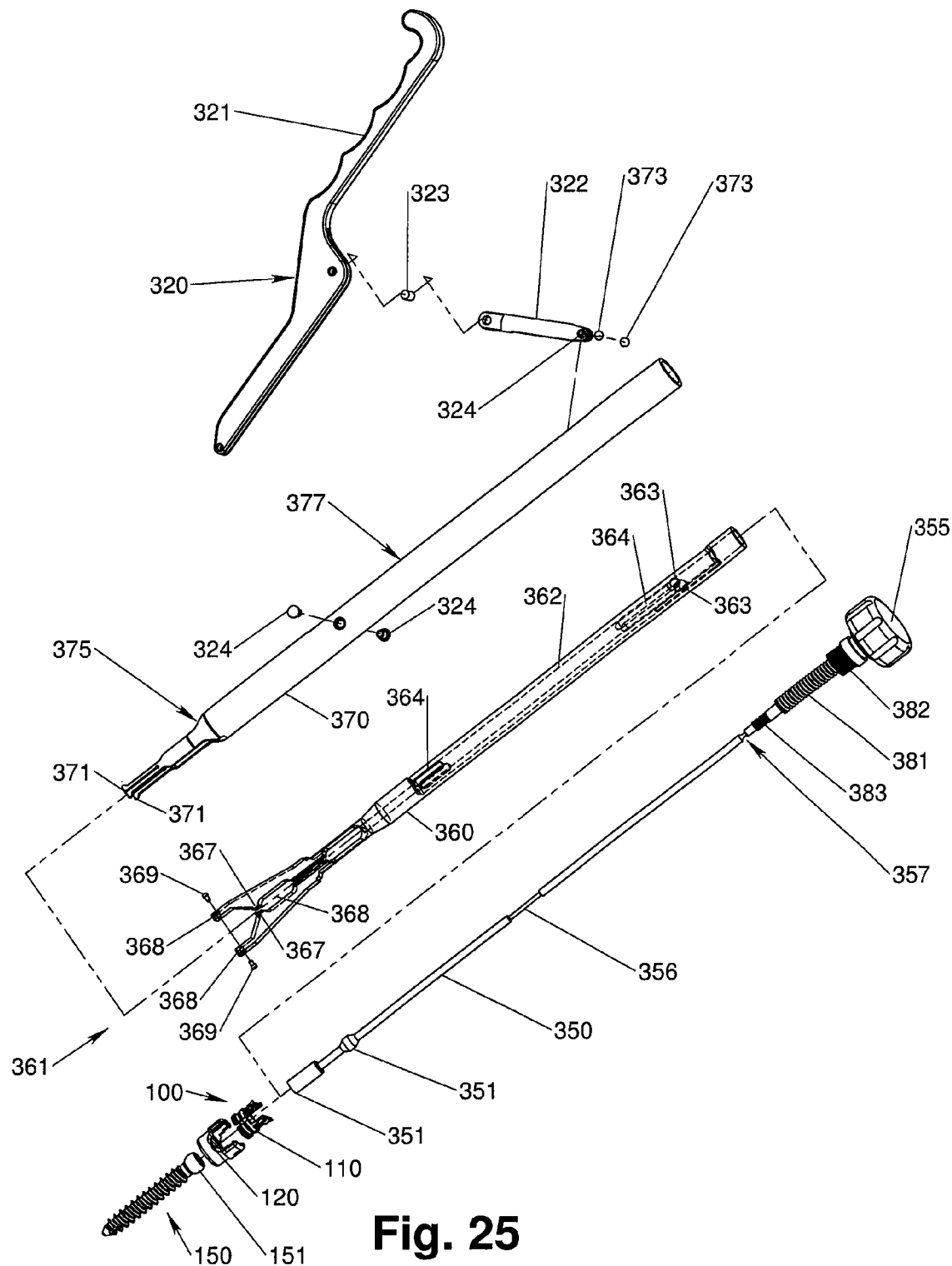
FIG. 25 is an exploded view of the instrument from FIG. 24.
Figure 27:
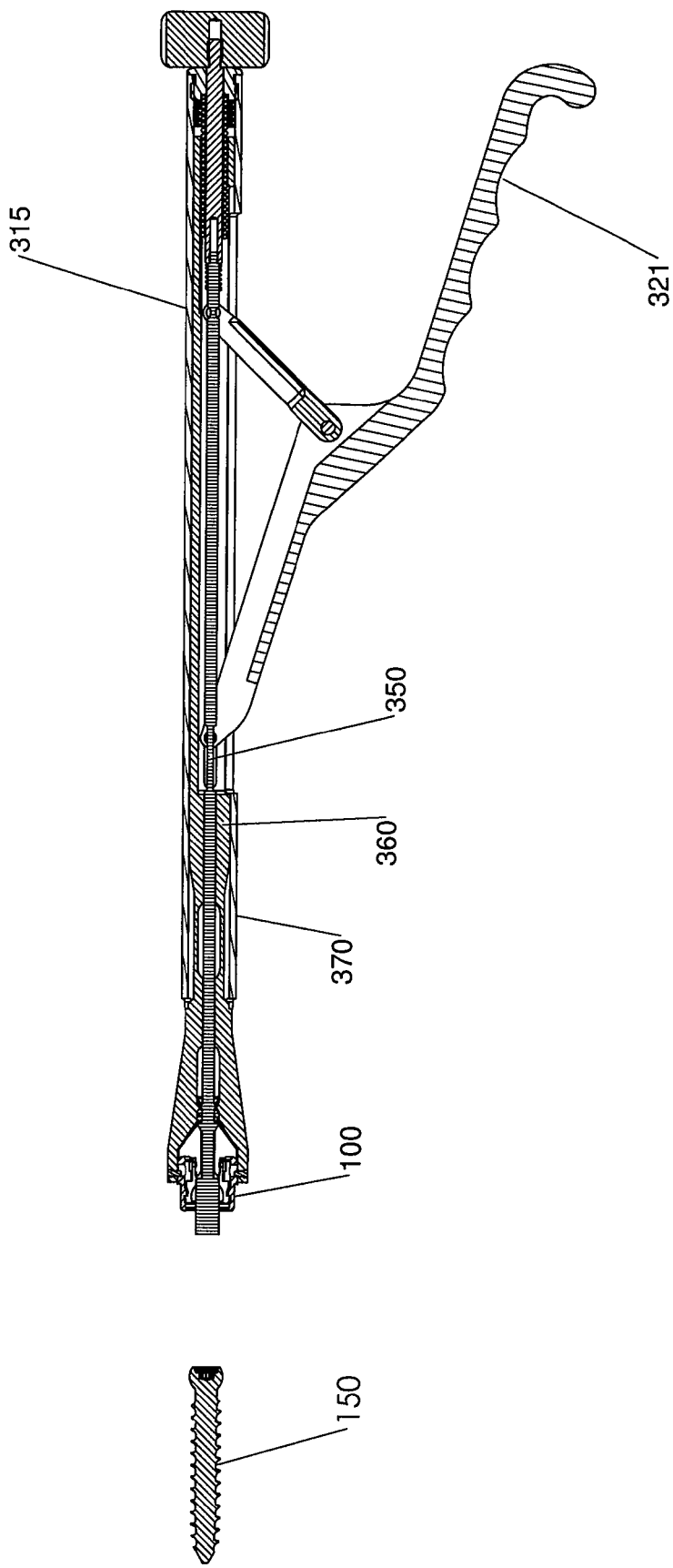
FIG. 27 is a cross-sectional view of the instrument from FIG. 24.

The instrument 301 includes three concentric shafts, as shown in the exploded view of FIG. 25 and the cross-sectional view of FIG. 27. An inner shaft 350 includes the anchor securement head 351. The inner shaft 350 also includes a knob 355 for rotating the shaft 350 about its axis. The inner shaft may optionally include a number of axially assembled components, or may be formed as a single unitary structure. An intermediate sleeve 360 is disposed about the inner shaft and includes grasping portions 368 with pegs 369 or other features adapted to grasp exterior features of the coupling assembly outer member 120. An outer sleeve 370 is disposed about the inner shaft and intermediate sleeve, and includes side openings 375 to permit the grasping member 368 to protrude therethrough. The outer sleeve 370 also includes an insert driver 371 extending therefrom configured to abut the top of the insert member 110 in order to drive the insert member into the outer member. An elongate opening 377 in the outer sleeve 370 and an elongate opening 362 in the intermediate sleeve 360 allow the instrument actuator 320 to be secured to the interior of the instrument. The actuator 320 includes an actuator lever 321 pivotably secured to the outer sleeve 370 at one end by rivets 324 or the like and a linkage 322 pivotably coupled to the lever 321 by a pin 323. The linkage 322 extends from the lever 321 to the interior of the instrument. The linkage 322 contains apertures 324 for receiving shiftable bearing members 373 for selectively coupling the linkage 322 to the inner shaft 350 and intermediate sleeve 360, as will be described further below.

The head 351 of the inner shaft 350 is configured to secure the head 151 of the anchor member 150. For instance, the shaft head 351 may include an exterior thread to match an interior thread in a drive recess in the top of the anchor head. Rotation of the knob 355 attached to the inner shaft 350 may be used to rotate the shaft 350, which is freely rotatable within the intermediate and outer sleeves, thereby threading the securement head 351 into the anchor head 151, firmly securing the anchor 150 to the inner shaft 350.

The inner shaft 350 also includes a boss 352 or other enlarged structure configured to force open the grasping members 368 of the intermediate sleeve as the inner shaft travels axially. For instance, when the inner shaft is fully extended to engage anchor member 150, the boss 352 abuts protrusions 367 extending inwardly into a passage of the intermediate sleeve 360, deflecting the resiliently flexible grasping member 368 of the intermediate sleeve to an open position. As the inner shaft 350 is retracted in order to pull the anchor member 150 into a coupling assembly, the boss 352 shifts to an enlarged portion 368 of the intermediate sleeve passage, allowing the grasping members 368 to shift to a closed or clamped position, firmly grasping the outer member 120 of the coupling assembly.

A narrow portion 356 of the inner shaft may be provided to interact with structures, such as bolts 324 on the outer sleeve 370, in order to limit travel of the inner shaft 350. To allow the bolts 324 to reach the inner shaft, the intermediate sleeve 370 is provided with elongate slots 364 through which the bolts may pass. The elongate slots 364 allow the intermediate sleeve 360 to shift axially without interference from the bolts 324 extending from the outer sleeve toward the narrow portion 356 of the inner shaft.

An annular recess 357 at the proximal end of the inner shaft 350 is configured to receive shiftable bearing elements 373, as will be described below. Apertures 363 in the intermediate shaft 360 are also configured to receive the shiftable bearing elements 373, allowing the shiftable bearing elements 373, which are partially located in apertures 324 of the actuator linkage 322, to selectively couple and decouple the actuator with the inner shaft and intermediate sleeve, as will be described further below. Elongate tracks 364 on the interior surface of the intermediate sleeve 360 guide the shiftable bearing elements toward the apertures 363.

The rear or proximal portion of the shaft 350 is larger than the front part to provide a surface for springs 381 and 382 to rest upon. These springs return the components of the instrument 301 to their initial positions once the actuator lever 321 is released. The wave-spring 382 rests inside the outer sleeve 370 and acts on the intermediate sleeve 360 to bias it forward (toward the distal instrument end). The long spring 381 resides inside the intermediate sleeve 360 and biases the actuator linkage 322, and the lever 321 to which the linkage is coupled, back to its original position when the lever is released. Springs 381 and 382 bias the inner shaft and intermediate sleeve forward (distally), so that prior to depressing the actuator lever 321 the anchor securement head 351 is fully extended and the grasping members 368 are in an open position (deflected apart by boss 352 on the inner shaft 350). An additional spring 383 may also be provided to bias the shiftable bearing members 373 to their initial positions.

In use, after the instrument receives a coupling device and an anchor member is secured to the securement head 351, the actuator lever 321 is pivoted to shift the inner shaft 350 and intermediate sleeve 360 rearward (proximally) relative to the stationary outer sleeve 370.

Figure 26:
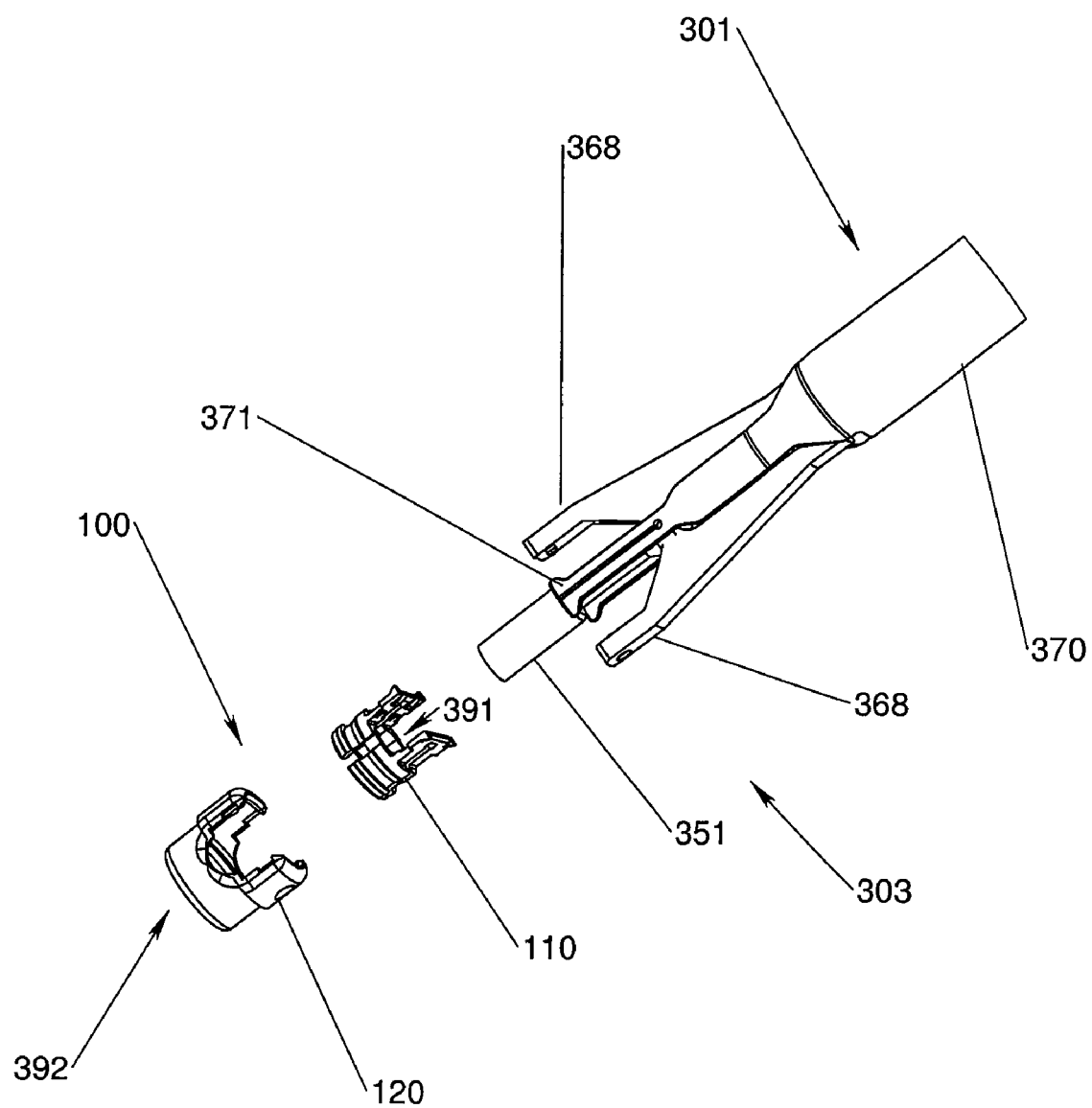
FIG. 26 is a magnified view of the distal end of the instrument from FIG. 24.

The coupling device 100 is received by the distal end 303 of the instrument 301 as shown in FIGS. 26-27. The insert member 110 and outer member 120 of the coupling device 100 are loaded onto the anchor locking instrument 301 by inserting the anchor securement head 351 through axial passages 391 and 392 of the coupling assembly components. The outer member 120 is secured by grasping members 368, which clamp around the outer member 120. The insert member 110 abuts the insert driver portion 371 of the outer sleeve 370. The anchor securement head 351 is secured to the head of an anchor member 150.

Figure 28:
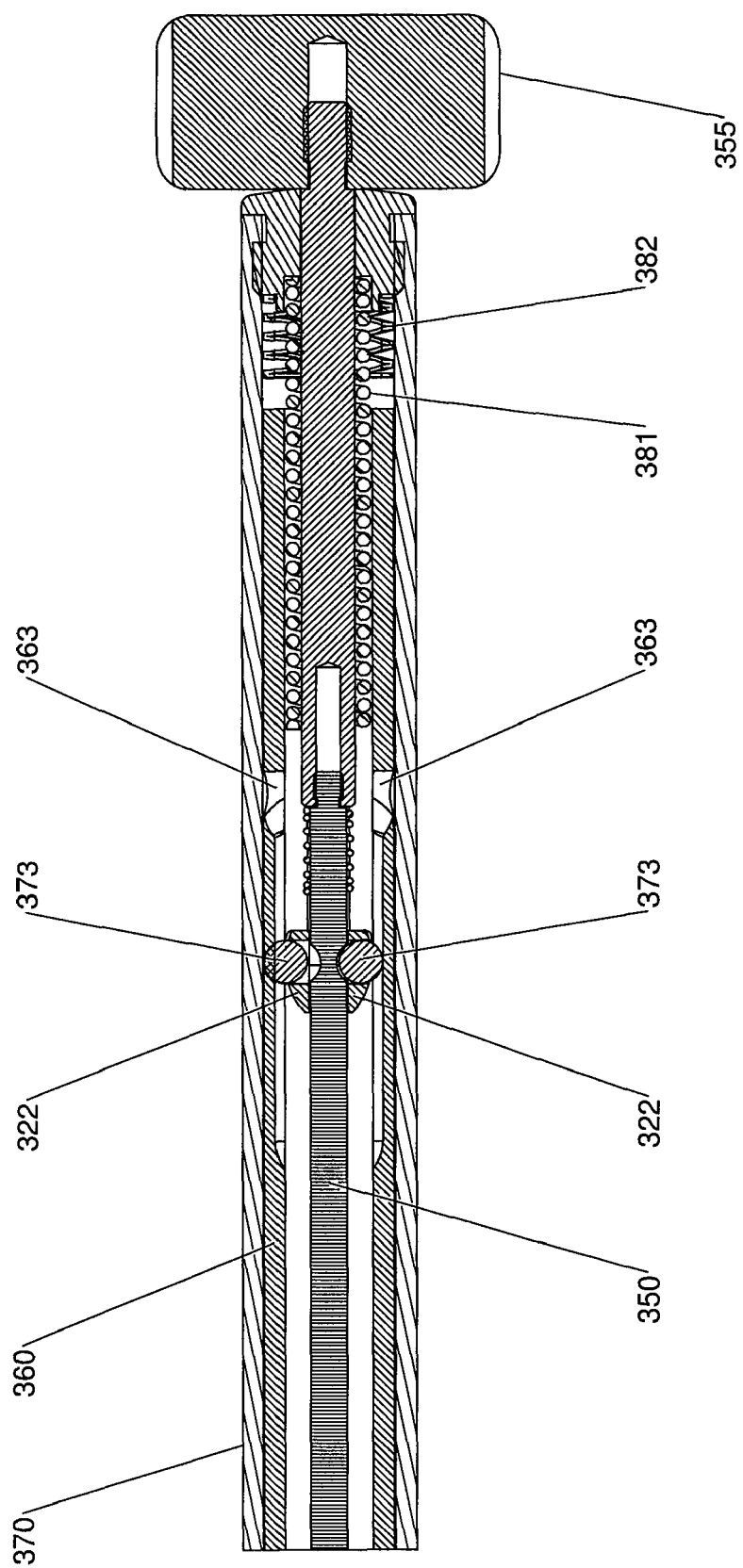
FIG. 28 is a cross-sectional view of the proximal end of the instrument from FIG. 24 illustrating a switching mechanism in its initial position.
Figure 29:
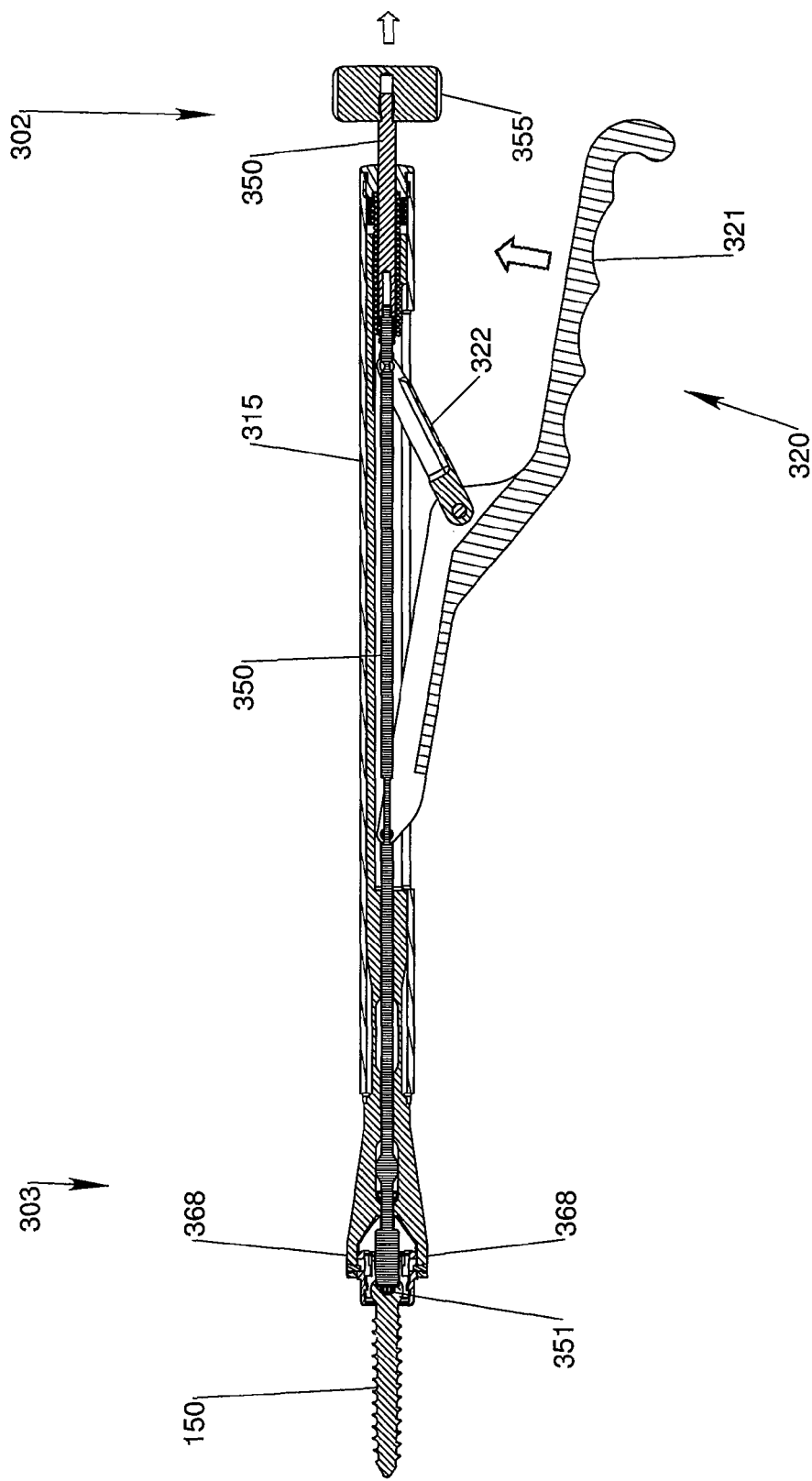
FIG. 29 is a cross-sectional view of the instrument from FIG. 24 as the actuator is shifted.
Figure 30:
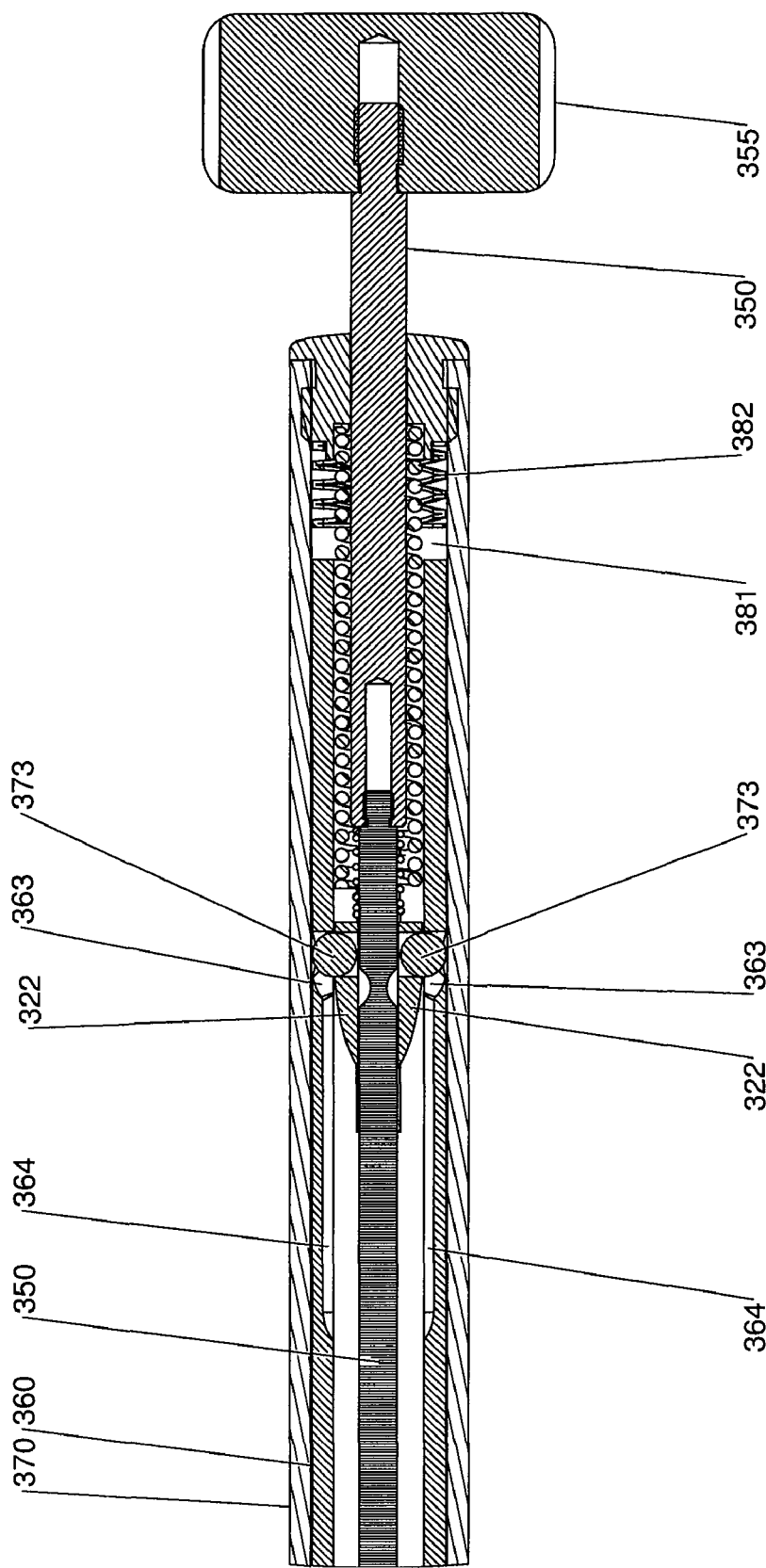
FIGS. 30 and 31 are cross-sectional views of the proximal end of the instrument from FIG. 24 illustrating the operation of the switching mechanism as the instrument actuator is shifted.
Figure 31:
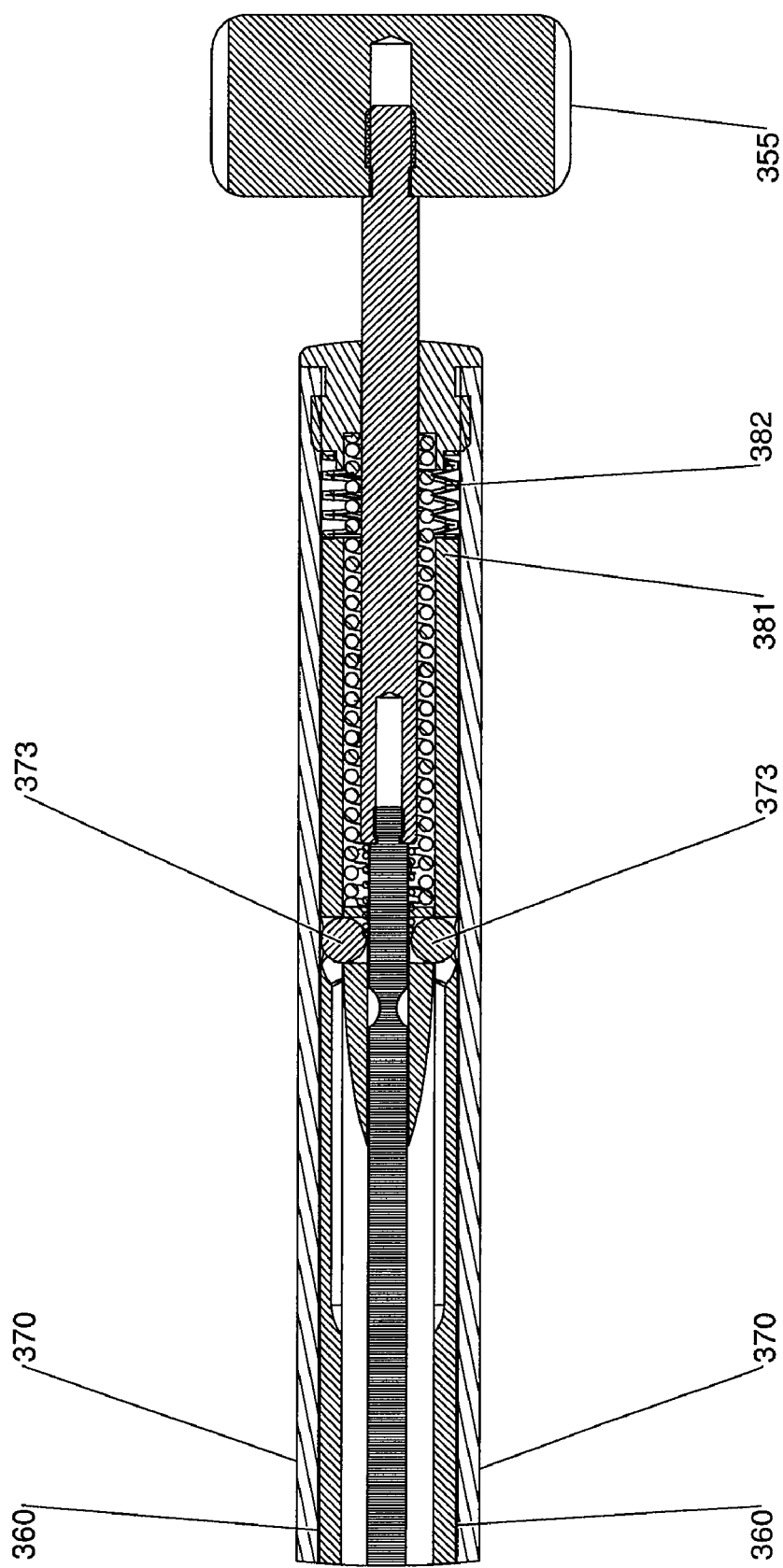
Figure 32:
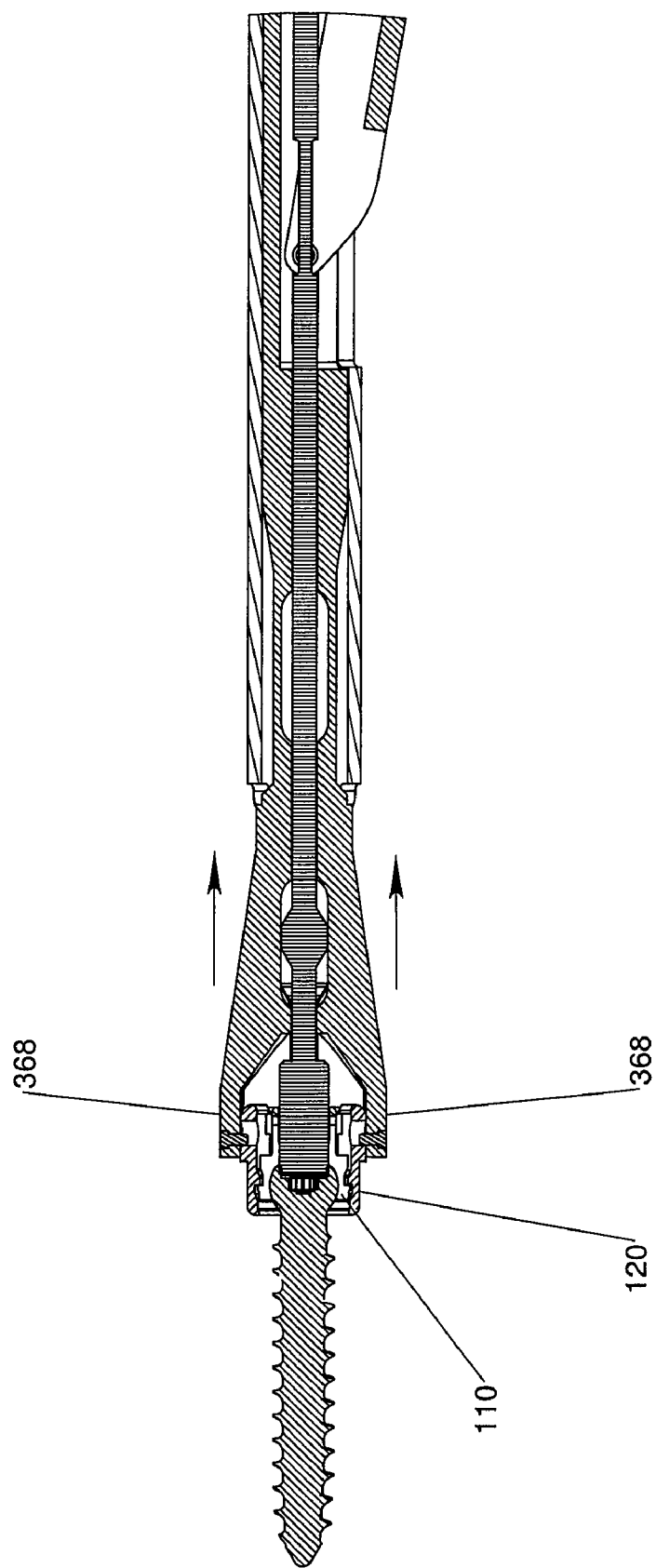
FIG. 32 is a cross-sectional view of the distal end of the instrument of FIG. 24 as it operates to secure an anchor member in a coupling assembly.

As seen in the partial cross section of FIG. 28, when the actuator is in the initial position shiftable bearing elements located partially within the actuator linkage 322 bear against an annular recess in the inner shaft member 350. As the actuator lever 321 is pivoted toward the instrument handle 315, as shown in the cross-section of FIG. 29, the actuator linkage 322 is shifted rearward toward the proximal end 302 of the instrument, axially shifting the inner shaft member 350 along the instrument axis in the same direction due to coupling of the inner shaft 350 and linkage 322 by the shiftable bearing elements 373. As the actuator linkage 322 is shifted rearward, long spring 381 is compressed. As shown in FIG. 30, the inner shaft is sized and configured so that when the inner shaft member 350 is shifted to a predetermined axial position, at which point the anchor member 150 secured to the inner shaft has been snap locked into the coupling assembly insert member 110, the shiftable bearing elements 373 reach apertures 363 in the intermediate sleeve 360, allowing the shiftable bearing elements 373 to shift into the apertures 363 and away from the inner shaft member 350. The surface of the inner shaft may be configured to bias the shiftable bearing elements 373 toward the intermediate sleeve apertures. This decouples the actuator linkage 322 from the inner shaft member 350 and instead couples the actuator linkage 322 to the intermediate sleeve 360. Further shifting of the actuator lever shifts the actuator linkage 322 and intermediate sleeve 360 rearward as in FIG. 31, compressing spring 382. By shifting the intermediate sleeve 360 rearward relative to the outer sleeve 370, the intermediate sleeve grasping members 368 shift the coupling assembly outer member 120 over the insert 110 as the insert is held stationary on the inner shaft 350, as shown in FIG. 32. The insert driver 371 of the stationary outer member 370 assists in inhibiting movement of the coupling assembly insert member 110, so that the insert is inserted in and compressed by the outer member 120. The anchor member 150 is thereby locked within the coupling device 100 so that friction prevents further pivoting of the anchor head with respect to the coupling assembly.

Upon release of the actuator lever 321, spring 382 shifts the intermediate sleeve 360 back to its initial position, and long spring 381 shifts the actuator linkage 322 back into its initial position. As the actuator linkage 322 moves back to its initial position, the geometry of intermediate sleeve apertures 363 cause shiftable bearing elements 373 to shift away from the intermediate sleeve apertures and into engagement with the annular recess 357, decoupling the linkage 322 and intermediate sleeve 360 and re-coupling linkage 322 to the inner shaft 350. The long spring 381 then returns the inner shaft member 350 to its initial position.

Figure 33:
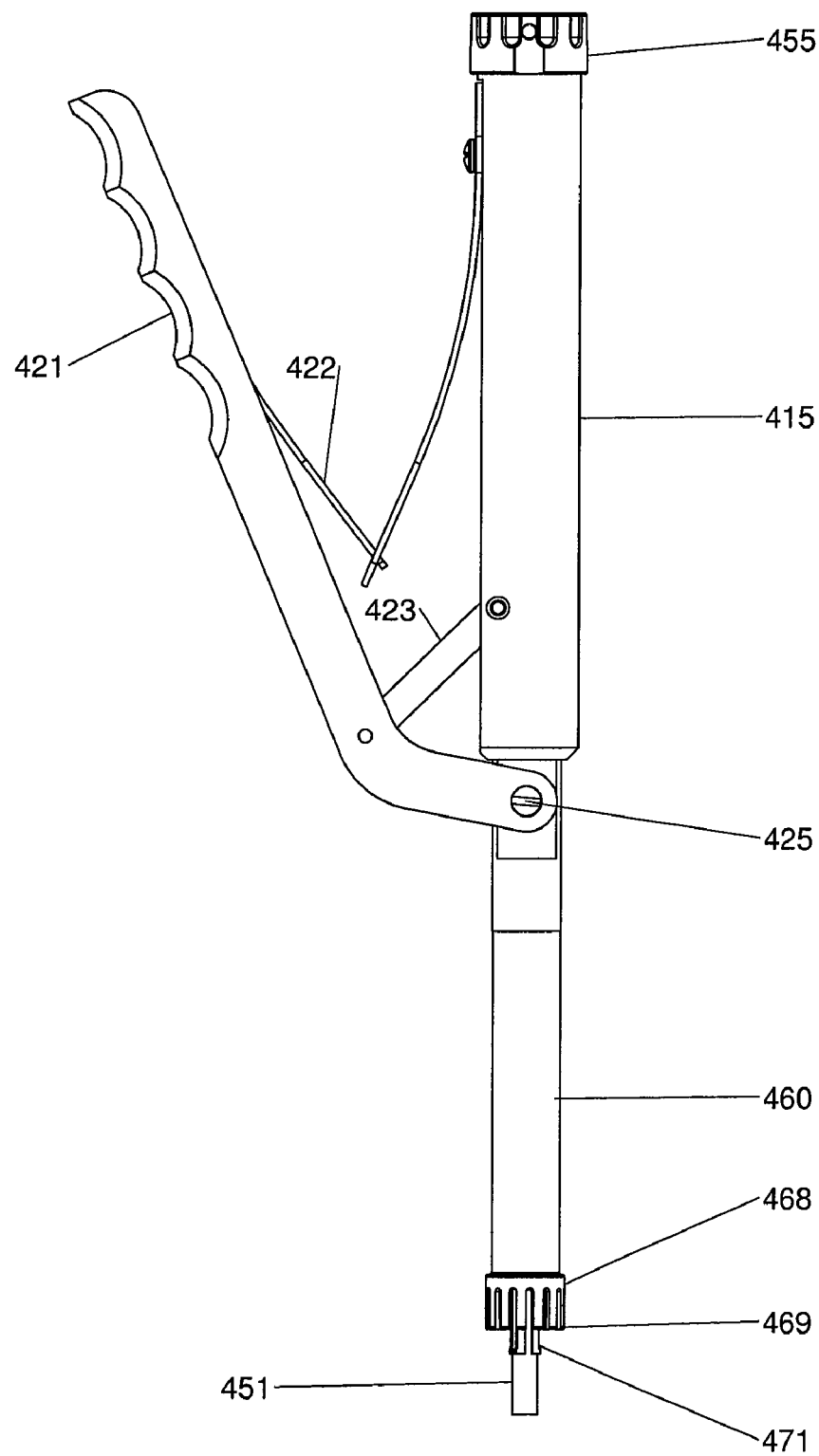
FIG. 33 is a front view of another form of instrument configured to secure the position of an anchor member within a coupling assembly.
Figure 34:
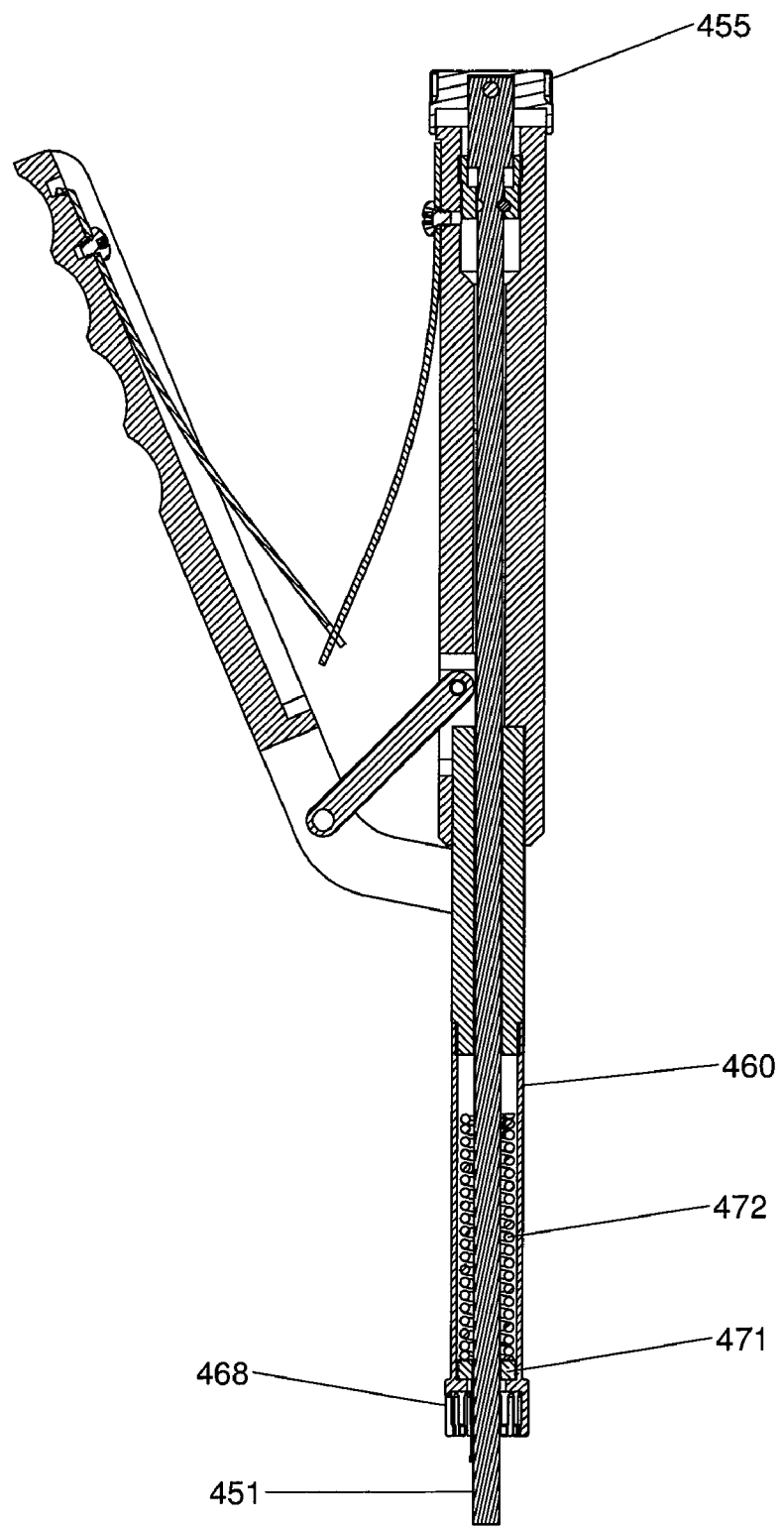
FIG. 34 is a cross-sectional view of the instrument of FIG. 33.

Yet another instrument for the manipulation of the rod coupling device 100 is disclosed in FIGS. 33-37. As with the instrument 301 of FIGS. 24-33, instrument 401 is designed to lock the coupling device to an anchor member prior to disposing a spinal rod in the coupling assembly. As shown in FIG. 33, the elongate anchor locking instrument 401 includes a cylindrical handle 415, a manipulator member 460 extending axially from the handle, and an actuator lever 421 pivotably connected to both the handle and the manipulator member. The actuator lever 421 is biased away from the handle by a wishbone spring 422, and pivoting the lever 421 toward the instrument handle 415 drives the manipulator member 460 axially away from the handle along the elongate instrument's axis. A spring-loaded insert driver 471 is disposed inside the hollow manipulator member 460, and an anchor securement shaft 451 is disposed within the insert driver. The manipulator member 460 includes a grasping head 468 having a plurality of resiliently deflectable fingers 469. The cross-sectional view of FIG. 34 illustrates the placement of the handle 415, actuator lever 421, and the actuator linkage 422. The actuator linkage 422 links the actuator lever to the handle. The instrument further includes a manipulator member 460, an insert driver 471 with insert driver spring 472, and anchor securement shaft 451, all of which are also seen in FIG. 34. The anchor securement shaft 450 passes through the length of the instrument and is freely rotatable therein, so that by rotating the cap 455 at the top of the instrument, threading at the end of the anchor securement shaft 451 may be threaded into corresponding threads on the interior of the anchor head to secure the anchor to the securement shaft 451.

Figure 35:
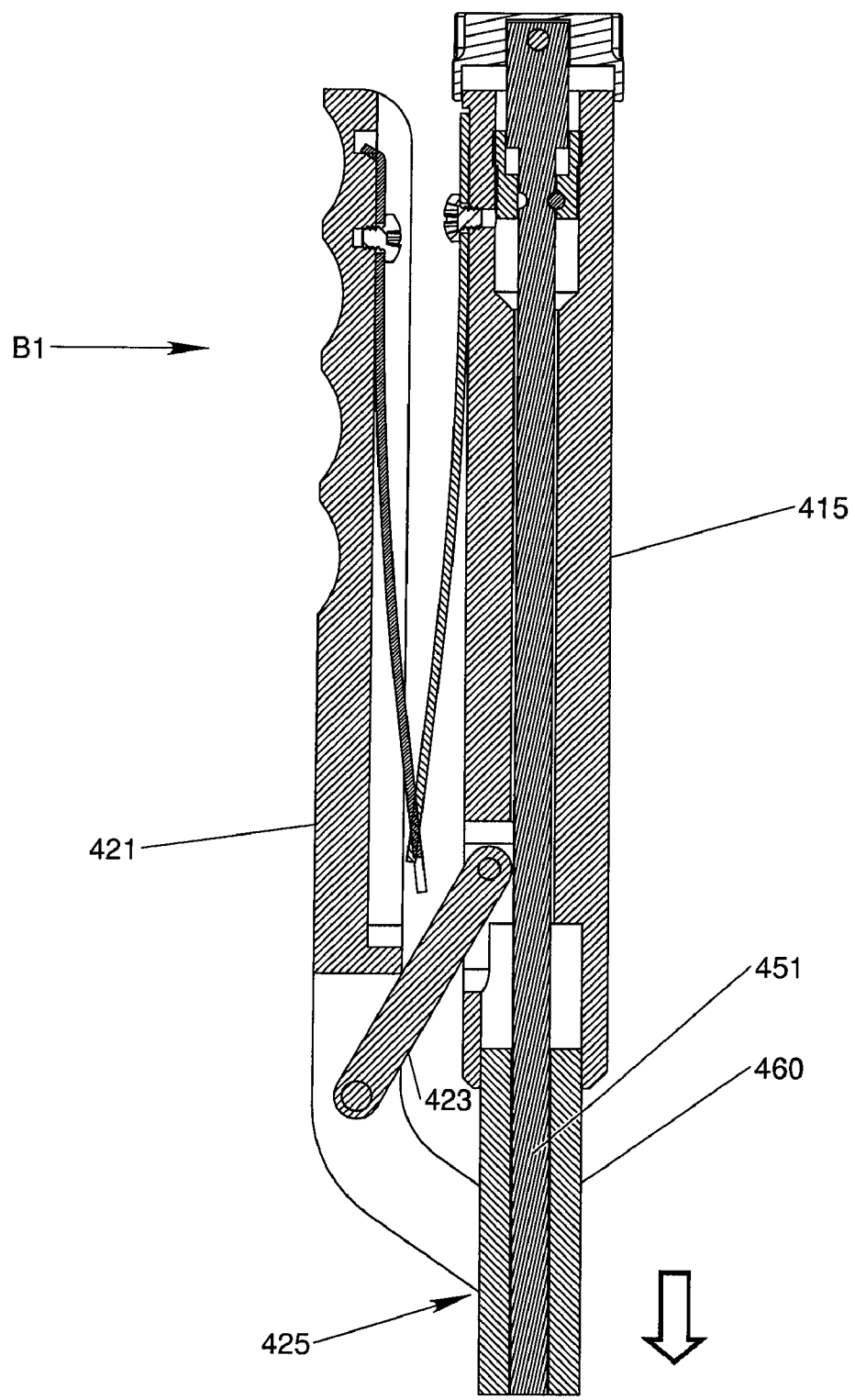
FIG. 35 demonstrating the movement of components as the actuator lever is pivoted toward the instrument handle.

By pivoting the actuator lever 421 toward the handle 415 as shown in FIG. 35, actuator linkage 423 forces the pivot point 425 of the actuator lever 421 linearly along the instrument's axis. Since the pivot point 425 couples the actuator lever 421 to the manipulator member 460, the manipulator member 460 is advanced along the instrument axis.

Figure 36:
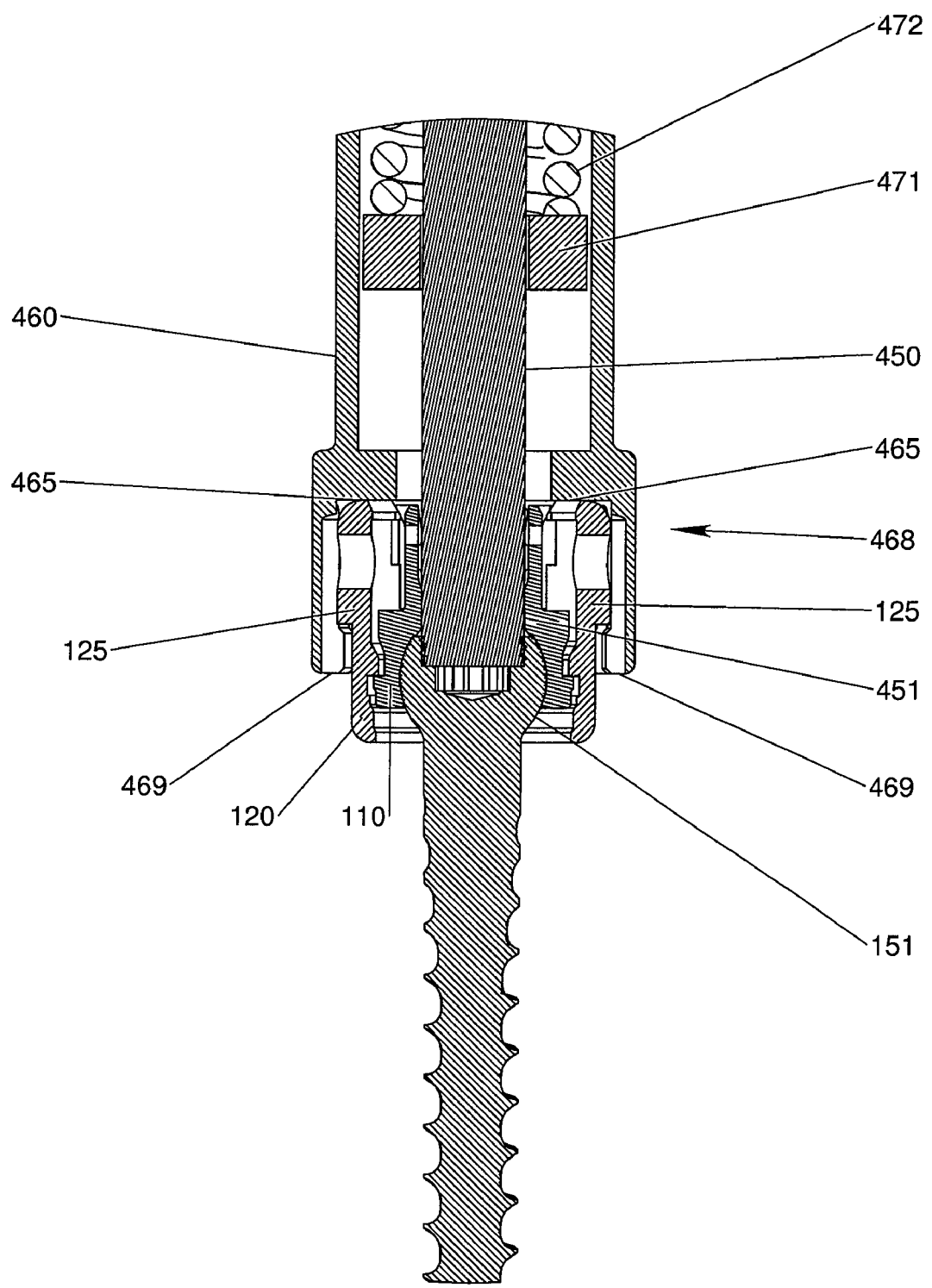
FIG. 36 is a front cross-section of the distal end of the instrument of FIG. 33 as it secures an anchor member within a coupling assembly.
Figure 37:
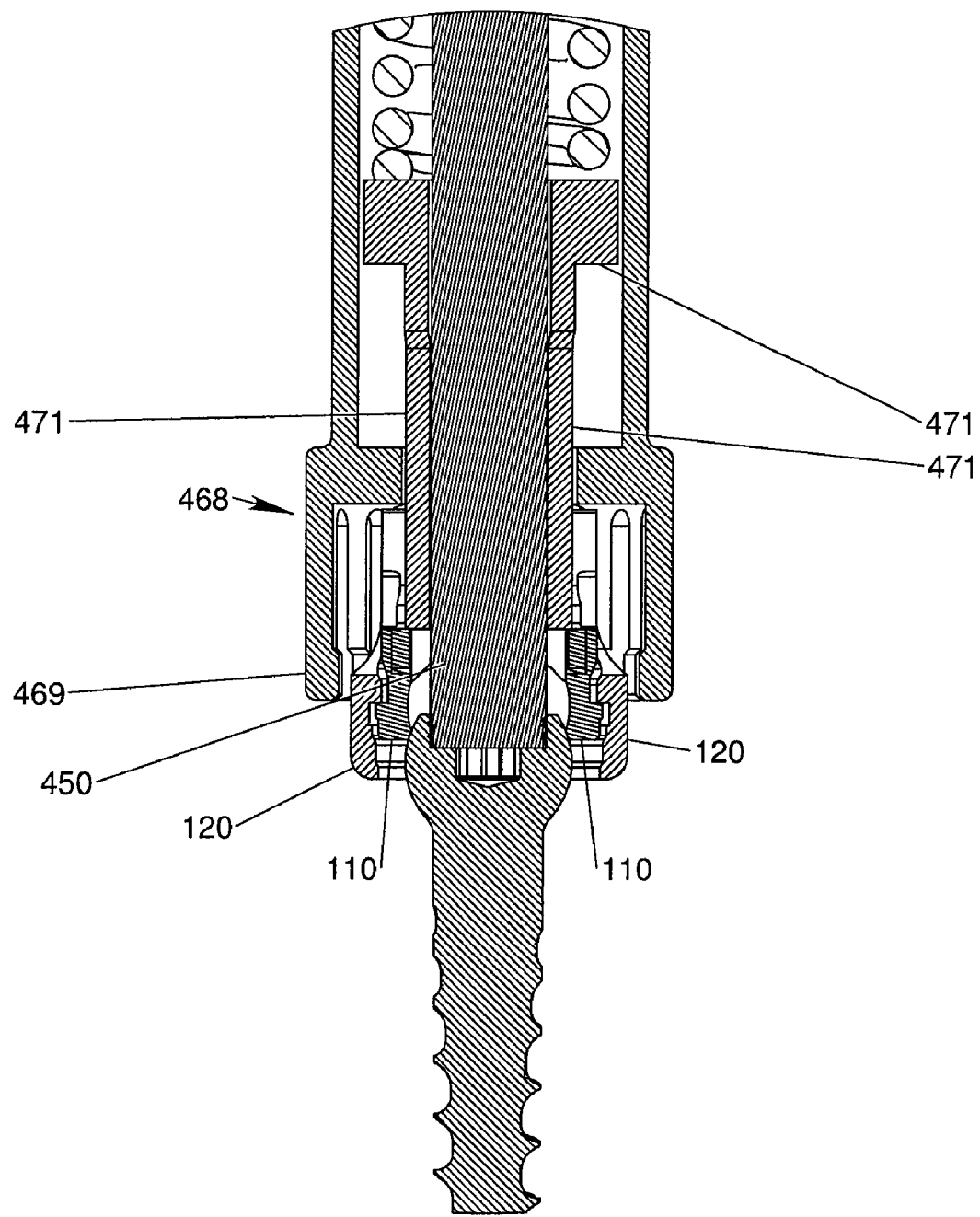
FIG. 37 is a side cross-section of the distal end of the instrument of FIG. 33 as it secures an anchor member within a coupling assembly.

As shown in the front cross section of FIG. 36, advancement of the manipulator member 460 causes abutment surfaces 465 on the interior of the manipulator head 468 to abut the coupling assembly, forcing the outer member 120 and insert member 110 of the coupling assembly onto the anchor head 151 secured to the end of the securement shaft 451. Insert driver spring 472 causes insert driver 471 to exert force downward onto the insert member 110 to maintain the insert member within the outer member 120 (as best shown in the side cross section of FIG. 37). However, since insert member 110 is only partially inserted into the coupling assembly outer member 120, the anchor head 151 is snap-locked into the insert member 110 but is not frictionally locked into a fixed position. As the manipulator head 468 is driven onto the coupling assembly, resiliently flexible fingers 469 snap lock around shoulder portions 125 of the coupling assembly outer member 120.

Upon release of the actuator lever, the manipulator member 460 is drawn back toward the handle along the instrument axis. The manipulator head 468, which is snap locked to the coupling assembly outer member 120, pulls up on the outer member, thereby compressing the insert member 110 around the anchor head 151 and locking the anchor at a fixed orientation with respect to the coupling assembly. The spring loaded insert driver 471 exerts force downward onto the insert member 110 to facilitate locking of the coupling assembly. Preferably, the flexible fingers 469 of the manipulator head 468 are configured so that the force retracting the manipulator member 460 automatically overcomes the snap lock between the manipulator head and coupling assembly outer member, disengaging the manipulator head. However, the manipulator head may also be manually disengaged from the assembly. Once the manipulator head is disengaged, the securement shaft 450 is rotated to unthread the end 451 from the anchor 150, disengaging the instrument.

Although the invention has been described herein with reference to particular embodiments and/or structures, these embodiments and structures are meant to be exemplary and are not meant to limit the scope of the invention in any way.

What is claimed is:

1. An instrument for locking a spinal rod to a rod coupling device, the instrument comprising: an elongate instrument body having an axis; at least one grasping member for securing the coupling device in a fixed position with respect to the instrument body; a drive member for advancing a cap member in an axial direction toward the coupling device secured by the grasping member; a shiftable reducing member for engaging the spinal rod and driving the spinal rod in the axial direction into engagement with the coupling device; and a drive coupler for coupling the reducing member to the drive member so that the reducing member advances in the axial direction simultaneously with the drive member, the drive coupler having at least one portion that disengages from the reducing member with the reducing member advanced to a predetermined axial position with respect to the drive member so that the drive member is free to advance in the axial direction without further advancement of the reducing member in the axial direction.

2. The instrument of claim 1, wherein the drive coupler comprises a pin member coupling a coupling sleeve member to the drive member and a shifting element configured to shift away from the coupling sleeve member to disengage the reducing member from the drive member.

3. The instrument of claim 1, further comprising an inhibitor switch that is shifted to a first position to limit axial advancement of the drive member by a first amount, and shifted to a second position to permit advancement by a second amount, the second amount being greater than the first amount.

4. The instrument of claim 1, further comprising a ratchet device for allowing sequential advancement of the drive member through a plurality of predetermined positions.

5. The instrument of claim 1, wherein the reducing member is an elongate hollow cylinder disposed about the drive member.

6. The instrument of claim 5, wherein the reducing member includes at least one slit to allow axial compression of the reducing member in an axial direction.

7. The instrument of claim 5, wherein the at least one slit is helical.

8. An instrument for locking a spinal rod to a rod coupling device, the instrument comprising: an elongate instrument body having an axis; at least one grasping member for securing the coupling device in a fixed position with respect to the instrument body; a drive member for advancing a cap member in an axial direction toward the coupling device secured by the grasping member; a shiftable reducing member for engaging the spinal rod and driving the spinal rod in the axial direction into engagement with the coupling device, the reducing member forming an elongate hollow cylinder disposed about the drive member and including at least one slit to allow axial compression of the reducing member in an axial direction; and a drive coupler for coupling the reducing member to the drive member so that the reducing member advances in the axial direction simultaneously with the drive member, the drive coupler having at least one portion that disengages from the reducing member with the reducing member advanced to a predetermined axial position with respect to the drive member so that the drive member is free to advance in the axial direction without further advancement of the reducing member in the axial direction.

9. The instrument of claim 8, wherein the drive coupler comprises a pin member coupling a coupling sleeve member to the drive member and a shifting element configured to shift away from the coupling sleeve member to disengage the reducing member from the drive member.

10. The instrument of claim 8, further comprising a ratchet device for allowing sequential advancement of the drive member through a plurality of predetermined positions.

11. The instrument of claim 8, wherein the at least one slit is helical.

12. An instrument for locking a spinal rod to a rod coupling device, the instrument comprising: an elongate instrument body having an axis; at least one grasping member for securing the coupling device in a fixed position with respect to the instrument body; a drive member for advancing a cap member in an axial direction toward the coupling device secured by the grasping member; a shiftable reducing member for engaging the spinal rod and driving the spinal rod in the axial direction into engagement with the coupling device; a ratchet device for allowing sequential advancement of the drive member to a plurality of predetermined positions; and a drive coupler for releasably coupling the reducing member to the drive member, the drive coupler comprising a pin member coupling a coupling sleeve member to the drive member and a shifting element configured to shift away from the coupling sleeve member to disengage the reducing member from the drive member when the drive member and reducing member arrive at a predetermined disengagement position.

13. The instrument of claim 12, wherein the reducing member is an elongate hollow cylinder disposed about the drive member.

14. An instrument for locking a spinal rod to a rod coupling device, the instrument comprising: an elongate instrument body having an axis; at least one grasping member for securing the coupling device in a fixed position with respect to the instrument body; a drive member for advancing a cap member in an axial direction toward the coupling device secured by the grasping member; a shiftable reducing member for engaging the spinal rod and driving the spinal rod in the axial direction into engagement with the coupling device; a ratchet device for allowing sequential advancement of the drive member to a plurality of predetermined positions; the reducing member including at least one slit to allow axial compression of the reducing member in the axial direction.

* * * * *